United States Patent
Bondensgaard et al.

(10) Patent No.: US 9,005,921 B2
(45) Date of Patent: *Apr. 14, 2015

(54) POLYNUCLEOTIDES ENCODING IL-31 MONOCLONAL ANTIBODIES

(71) Applicants: ZymoGenetics, Inc., Princeton, NJ (US); Merck Serono S/A, Coinsins (CH)

(72) Inventors: Kent Bondensgaard, Vaerlose (DK); Roland Beckmann, Vienna (AU)

(73) Assignees: ZymoGenetics, Inc., Princeton, NJ (US); Merck Serono S/A, Coinsins (CH)

( * ) Notice: Subject to any disclaimer, the term of this patent is extended or adjusted under 35 U.S.C. 154(b) by 0 days.

This patent is subject to a terminal disclaimer.

(21) Appl. No.: 14/174,870

(22) Filed: Feb. 7, 2014

(65) Prior Publication Data

US 2014/0186891 A1    Jul. 3, 2014

Related U.S. Application Data

(60) Continuation of application No. 13/908,436, filed on Jun. 3, 2013, now Pat. No. 8,685,669, which is a division of application No. 12/329,820, filed on Dec. 8, 2008, now Pat. No. 8,470,979.

(60) Provisional application No. 61/012,362, filed on Dec. 7, 2007.

(51) Int. Cl.
| | |
|---|---|
| C12N 5/10 | (2006.01) |
| C12N 15/63 | (2006.01) |
| C07K 16/24 | (2006.01) |
| A61K 39/00 | (2006.01) |

(52) U.S. Cl.
CPC ......... *C07K 16/244* (2013.01); *A61K 2039/505* (2013.01); *C07K 2317/24* (2013.01); *C07K 2317/52* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 4,054,646 | A | 10/1977 | Giaever |
| 5,078,997 | A | 1/1992 | Hora et al. |
| 5,116,964 | A | 5/1992 | Capon et al. |
| 5,492,841 | A | 2/1996 | Craig |
| 5,530,101 | A | 6/1996 | Queen et al. |
| 5,891,997 | A | 4/1999 | Mosley et al. |
| 5,925,735 | A | 7/1999 | Baumgartner et al. |
| 6,043,344 | A | 3/2000 | Jacobs et al. |
| 6,086,874 | A | 7/2000 | Yoshida et al. |
| 7,064,186 | B2 | 6/2006 | Sprecher et al. |
| 7,157,559 | B2 | 1/2007 | Brady et al. |
| 7,303,896 | B2 | 12/2007 | Ghilardi et al. |
| 7,425,325 | B2 | 9/2008 | Sprecher et al. |
| 7,427,494 | B2 | 9/2008 | Sprecher et al. |
| 7,459,293 | B2 | 12/2008 | Sprecher et al. |
| 7,468,423 | B2 | 12/2008 | Brady et al. |
| 7,479,542 | B2 | 1/2009 | Brady et al. |
| 7,485,701 | B2 | 2/2009 | Brady et al. |
| 7,485,702 | B2 | 2/2009 | Brady et al. |
| 7,494,804 | B2 | 2/2009 | Sprecher et al. |
| 7,495,077 | B2 | 2/2009 | Brady et al. |
| 7,495,078 | B2 | 2/2009 | Brady et al. |
| 7,495,079 | B2 | 2/2009 | Brady et al. |
| 7,495,080 | B2 | 2/2009 | Sprecher et al. |
| 7,507,795 | B2 | 3/2009 | Sprecher et al. |
| 7,514,077 | B2 | 4/2009 | Yao et al. |
| 7,514,536 | B2 | 4/2009 | Brady et al. |
| 7,517,961 | B2 | 4/2009 | Brady et al. |
| 7,521,537 | B2 | 4/2009 | Sprecher et al. |
| 7,531,636 | B2 | 5/2009 | Sprecher et al. |
| 7,531,637 | B2 | 5/2009 | Siadak et al. |
| 7,544,779 | B2 | 6/2009 | Brady et al. |
| 7,582,450 | B2 | 9/2009 | Brady et al. |
| 7,588,918 | B2 | 9/2009 | Brady et al. |
| 7,588,919 | B2 | 9/2009 | Brady et al. |
| 7,595,174 | B2 | 9/2009 | Brady et al. |
| 7,608,427 | B2 | 10/2009 | Brady et al. |
| 7,608,428 | B2 | 10/2009 | Brady et al. |
| 7,629,148 | B2 | 12/2009 | Brady et al. |
| 7,629,149 | B2 | 12/2009 | Brady et al. |
| 7,638,126 | B2 | 12/2009 | Yao et al. |
| 7,638,305 | B2 | 12/2009 | Brady et al. |
| 7,662,589 | B2 | 2/2010 | Brady et al. |
| 7,662,590 | B2 | 2/2010 | Brady et al. |
| 7,723,048 | B2 | 5/2010 | Bilsborough et al. |
| 7,727,518 | B2 | 6/2010 | Brady et al. |
| 7,740,834 | B2 | 6/2010 | Sprecher et al. |
| 7,799,323 | B2 | 9/2010 | Bilsborough et al. |

(Continued)

FOREIGN PATENT DOCUMENTS

| | | |
|---|---|---|
| EP | 1188830 | 3/2002 |
| JP | 10-501131 | 2/1998 |

(Continued)

OTHER PUBLICATIONS

Abstract from The American Society of Human Genetics Meeting, Nov. 7, 2003 on Gene Structure and Function.
Aioi, A. et al., Br J. Dermatol 144(1):12-18, 2001.
Akdis, C.A. et al., J. Invest. Dermatol. 113(4) 628-34, 1999.
Aleksza, M. et al., Br. J. Dermatol. 147(6):1135-41, 2002.
Antunez, C. et al., Clin. Exp. Allergy 34(4) 559-66, 2004.
Asadullah, K. et al., Arch. Dermatol 138(9):1189-96, 2002.
Askenase, P.W., Chem. Immunol. 78:112-23, 2000.
Bando et al., "Complete overlap of interleukin-31 receptor A and oncostatin M receptor beta in the adult dorsal root ganglia with distinct developmental expression patterns," Neuroscience 142(4): 1263-1271, 2006.
Barnes, K.C. et al., Genomics 37(1):41-50, 1996.
Bazan, "Structural design and molecular evolution of a cytokine receptor superfamily," Proc. Natl. Acad. Sci. USA, 87: 6934-6938 (Sep. 1990).

(Continued)

*Primary Examiner* — Elizabeth C Kemmerer
(74) *Attorney, Agent, or Firm* — Brian J. Walsh

(57) ABSTRACT

The invention provides humanized mouse anti-human IL-31 antibodies and antibody fragments that are capable of binding IL-31 and thereby neutralizing, inhibiting, limiting, or reducing the proinflammatory or pro-pruritic effects of IL-31.

30 Claims, 3 Drawing Sheets

(56) References Cited

U.S. PATENT DOCUMENTS

| | | |
|---|---|---|
| 7,871,618 B2 | 1/2011 | Bilsborough |
| 7,939,068 B2 | 5/2011 | Yao et al. |
| 7,943,132 B2 | 5/2011 | Yao et al. |
| 7,947,474 B2 | 5/2011 | Sprecher et al. |
| 8,013,124 B2 | 9/2011 | Sprecher et al. |
| 8,017,122 B2 | 9/2011 | Siadak et al. |
| 8,029,775 B2 | 10/2011 | Bilsborough et al. |
| 8,101,183 B2 | 1/2012 | Siadak et al. |
| 8,105,590 B2 | 1/2012 | Yao et al. |
| 8,105,591 B2 | 1/2012 | Yao et al. |
| 8,124,378 B2 | 2/2012 | Sprecher et al. |
| 8,377,438 B2 | 2/2013 | Yao et al. |
| 8,388,964 B2 | 3/2013 | Leung et al. |
| 8,409,571 B2 | 4/2013 | Yao et al. |
| 8,435,745 B2 | 5/2013 | Bilsborough et al. |
| 8,466,262 B2 | 6/2013 | Siadak et al. |
| 8,568,723 B2 | 10/2013 | Siadak et al. |
| 8,637,015 B2 | 1/2014 | Yao et al. |
| 8,685,395 B2 | 4/2014 | Yao et al. |
| 2003/0096339 A1 | 5/2003 | Sprecher et al. |
| 2004/0142422 A1 | 7/2004 | Sprecher et al. |
| 2004/0152161 A1 | 8/2004 | Cosman et al. |
| 2005/0214801 A1 | 9/2005 | Sprecher et al. |
| 2006/0182743 A1 | 8/2006 | Bilsborough |
| 2006/0188499 A1 | 8/2006 | Leung et al. |
| 2006/0188500 A1 | 8/2006 | Leung et al. |
| 2006/0228329 A1 | 10/2006 | Brady et al. |
| 2007/0048222 A1 | 3/2007 | Sprecher et al. |
| 2007/0048223 A1 | 3/2007 | Sprecher et al. |
| 2007/0048303 A1 | 3/2007 | Sprecher et al. |
| 2007/0048308 A1 | 3/2007 | Sprecher et al. |
| 2007/0048831 A1 | 3/2007 | Sprecher et al. |
| 2007/0048832 A1 | 3/2007 | Sprecher et al. |
| 2007/0048833 A1 | 3/2007 | Sprecher et al. |
| 2007/0048834 A1 | 3/2007 | Sprecher et al. |
| 2007/0048835 A1 | 3/2007 | Sprecher et al. |
| 2007/0049530 A1 | 3/2007 | Sprecher et al. |
| 2007/0105777 A1 | 5/2007 | Sprecher et al. |
| 2007/0140963 A1 | 6/2007 | Sprecher et al. |
| 2007/0140964 A1 | 6/2007 | Sprecher et al. |
| 2007/0141051 A1 | 6/2007 | Sprecher et al. |
| 2008/0026402 A1 | 1/2008 | Cosman et al. |
| 2009/0252732 A1* | 10/2009 | Siadak et al. ............. 424/139.1 |
| 2009/0274694 A1 | 11/2009 | Sprecher et al. |
| 2009/0274700 A1 | 11/2009 | Presnell et al. |
| 2009/0280121 A1 | 11/2009 | Bilsborough et al. |
| 2010/0008909 A1 | 1/2010 | Siadak et al. |
| 2010/0055101 A1 | 3/2010 | Sprecher et al. |
| 2010/0297065 A1 | 11/2010 | Brady et al. |
| 2011/0293514 A1 | 12/2011 | Siadak et al. |
| 2013/0266562 A1 | 10/2013 | Siadak et al. |
| 2014/0080181 A1 | 3/2014 | Siadak et al. |
| 2014/0127206 A1 | 5/2014 | Yao et al. |
| 2014/0186346 A1 | 7/2014 | Yao et al. |

FOREIGN PATENT DOCUMENTS

| | | |
|---|---|---|
| WO | 92/22653 | 12/1992 |
| WO | 96/04388 | 2/1996 |
| WO | WO 00/75314 | 12/2000 |
| WO | WO 01/93983 | 12/2001 |
| WO | WO 02/00690 | 1/2002 |
| WO | WO 02/00721 | 1/2002 |
| WO | WO 02/08288 | 1/2002 |
| WO | WO 02/29060 | 4/2002 |
| WO | WO 02/077230 | 10/2002 |
| WO | 03/048321 A2 | 6/2003 |
| WO | WO 03/060090 | 7/2003 |
| WO | WO 03/072740 | 9/2003 |
| WO | WO 2004/003140 | 1/2004 |
| WO | WO 2005/023862 | 3/2005 |
| WO | WO 2006/081573 | 8/2006 |
| WO | WO 2006/088955 | 8/2006 |
| WO | WO 2006/088956 | 8/2006 |
| WO | WO 2006/122079 | 11/2006 |
| WO | WO 2007/143231 | 12/2007 |
| WO | WO 2008/028192 | 3/2008 |
| WO | WO 2008/086505 | 7/2008 |
| WO | WO 2009/071696 | 6/2009 |

OTHER PUBLICATIONS

Berger, C.L. et al., Blood 105(4):1640-7, 2005.
Bilsborough, "IL-31 is Associated with CLA+ Skin Homing T cells in Patients with Atopic Dermatitis," Cytokine Symposium, Vienna, Austria, Aug. 2006.
Bilsborough et al., "IL-31 is associated with cutaneous lymphocyte antigen-positive skin homing T-cells in patients with atopic dermatitis", Journal of Allergy and Clinical Immunology, Mosby—Yearly Book, Inc., US 117(2): 418-425, Feb. 7, 2006.
Boder et al., "Directed evolution of antibody fragments with monovalent femtomolar antigen-binding affinity," Proceedings of the National Academy of Sciences of USA 97(20): 10701-10705, Sep. 26, 2000.
Boguniewics et al., "Atopic dermititis", J Allergy Clin Immunol, 117(2): S475-S480, Feb. 2006.
Bonecchi, R. et al., J. Exp. Med. 187(1):129-34, 1998.
Brune et al., Hautarzt 55: 1130-1136, 2004.
Burgess, W.H. et al., "Possible Dissociation of the Heparin-binding and Mitogenic Activities of Heparin-binding (Acidic Fibroblast) Growth Factor-1 from Its Receptor-Binding Activities by Site-directed Mutagenesis of a Single Lysine Residue", The Journal of Cell Biology, vol. 111, pp. 2129-2138 (1990).
Casset, F. et al., "A peptide mimetic of an anti-CD4 monoclonal antibody by rational design", Biochemical and Biophysical Research Communications, vol. 307, pp. 198-205 (2003).
Castellani et al., "Interleukin-31: A new cytokine involved in inflammation of the skin", International Journal of Immunopathology and Pharmacology, 19(1): 1-4, Jan. 13, 2006.
Chen, Y. et al., "Selection and Analysis of an Optimized Anti-VEGF Antibody: Crystal Structure of an Affinity-matured Fab in Complex with Antigen", J. Mol. Biol., vol. 293, pp. 865-881 (1999).
Claudy, Pathologic et Biologie, L'Expansion Scientifique Francaise, Paris, FR 44(10): 888-894, 1996.
Connors et al., "Hematology", pp. 263-268, Am Soc Hamatol Educ Program, 2002.
Conti et al., "Modulation of autoimmunity by the latest interleukins (with special emphasis on IL-32)" Autoimmunity Reviews 6(3): 131-137, 2007.
Dambacher et al., "Orphan class I cytokine receptor Zcytor17 is upregulated in activated monocytes and T cells," (W-2-4), Gut, Apr. 20, 2007; PMID: 17449633 Publisher: Gut.
Daniel et al., "Mapping of linear antigenic sites on the S Glycoprotein of a neurotroic murine coronavirus with synthetic peptides,"Virology 202: 540-549, 1994.
De Pascalis, R. et al., "Grafting of "Abbreviated" Complementarity-Determining Regions Containing Specificity-Determining Residues Essential for Ligand Contact to Engineer a Less Immunogenic Humanized Monoclonal Antibody", The Journal of Immunology, vol. 169, pp. 3076-3084 (2002).
Definition of "lichenification" in Stedman's Medical Dictionary, 27th Ed. (2000 Lippincott Williams & Wilkins).
Dillon et al., Entrez Database Accession No. AY499341, Jul. 10, 2004.
Dillon et al., "Interleukin 31, a cytokine produced by activated T cells, induces dermatitis in mice," Nature Immunology 5(7):752-760, Jul. 2004.
Dillon et al., "Transgenic mice overexpressing a novel cytokine (IL-31) develop a severe pruritic skin phenotype resembling atopic dermatitis," European Cytokine Network 14(3): 81, 2003.
Dillon, S.R. et al., Nat. Immunol. 6(1):114, 2005.
Diveu, C. et al., Eur. Cytokine Netw. 15(4):291-302, 2004.
Diveu, C. et al., J. Biol. Chem. 278(50):49850-49859, 2003.
Dreuw, A. et al., Immunobiology 210(6-8), 454, 2005.
Dreuw, A. et al., J. Biol. Chem. 279(34):36112-20, 2004.
Dreuw, A. et al., Keystone Symposia "Cytokines, Disease and Therapeutic Intervention," Feb. 12-17, 2005.

(56) References Cited

OTHER PUBLICATIONS

EMBL Accession No. AA381907, Apr. 1997.
EMBL Accession No. AC048338, Apr. 2000.
EMBL Accession No. AK005939, Feb. 8, 2001.
ExPASy Feature Aligner, Q8N17 (IL-31RA) human (accessed Nov. 11, 2007).
Fang, D. et al., Nat. Immunol. 3(3):281-7, 2002.
Felderhoff-Muesser et al., "IL-18: a key player in neuroinflammation and neurodegeneration," TRENDS in Neurosciences 28(9): 487-493, 2005.
Fritsch et al., "Drug-induced Stevens-Johnson symdrom/toxic epidermal necrolysis," Am J Clin Dermatol. 1(6): 349-360, Nov.-Dec. 2000, Abstract Only.
GenBank Accession No. AI123586, 1997.
GenBank Accession No. AI123586, Sep. 3, 1998.
GenBank Accession No. AI799583, 1997.
GenBank Accession No. AI799583, Jul. 6, 1999.
Ghilardi, N. et al., J. Biol. Chem. 277(19):16831-16836, 2002.
Grimstad et al., "Anti-interleukin-31-antibodies ameliorate scratching behavior in NC/Nga mice: a model of atopic dermatitis," Exp Dermatol. 18(1): 35-43, Jan. 2009. (Epub Oct. 24, 2008).
Gutermuth, J. et al., Int. Arch. Allergy Immunol. 135(3):262-76, 2004.
Harlow et al., Ed. Antibodies, A Laboratory Manual. Cold Spring Harbor Press. 1998, pp. 23-26.
Hashimoto, Y. et al., J. Dermatol. Sci. 35(2):143-50, 2004.
Hashimoto, Y. et al., Life Sci. 76(7):783-94, 2004.
Heng et al., "Alpha-1 antitrypsin deficiency in a patient with widespread prurigo nodularis," Australas J Dermatol 32(3): 151-157, 1991, Abstract Only.
Hermanns, H.M. et al., Experimental Dermatology 15(N3):219-20, 2006.
Hijnen, D. et al., J. Allergy Clin. Immunol. 113(2):334-40, 2004.
Holm, P. et al., "Functional mapping and single chain construction of the anti-cytokeratin 8 monoclonal antibody TS1", Molecular Immunology, vol. 44, pp. 1075-1084 (2007).
Hwang, S.T., Adv. Dermatol. 17:211-41, 2001.
Ip et al., "Interleukin-31 induces cytokine and chemokine production from human bronchial epithelial cells through activation of mitogen-activated protein kinase signalling pathways: implications for the allergic response," Immunology, Jul. 11, 2007; PMID: 17449633 Publisher: Gut.
Kaushansky et al., "The molecular and cellular biology of thrombopoietin: the primary regulator of platelet production," Oncogene 21: 3359-3367, 2002.
Lazar, E. et al., "Transforming Growth Factor α: Mutation of Aspartic Acid 47 and Leucine 48 Results in Different Biological Activities", Molecular and Cellular Biology, vol. 8, No. 3, pp. 1247-1252 (1988).
Lederman et al., "A single amino acid substitution in a common african allele of the CD4 molecule ablates binding of the monoclonal antibody, OKT4," Molecular Immunology 28(11): 1171-1181, 1991.
Leung et al., "IL-31 in Atopic Dermatitis," Grand Rounds Lecture, National Jewish Medical Center, Denver, CO, Dec. 14, 2005.
Leung et al., "IL-31 in Atopic Dermatitis," Grand Rounds, Mt. Sinai Medical Centre, New York, Jan. 5, 2006.
Leung et al., "New insights into atopic dermititis", Journal of Clinical Investigation 113(5): 651-657, Mar. 2004.
Leung, D.Y. et al., Lancet 361(9352): 151-60, 2003.
Lewis et al., "Comparison of the ability of wild type and stabilized human IgG4 to undergo Fab arm exchange with endogenous IgG4 in vitro and in vivo," Molecular Immunology, 1-7, 2009.
Lin, L. et al., J. Med. Dent. Sci. 50(1):27-33, 2003.
MacCallum, R.M. et al., "Antibody-antigen Interactions: Contact Analysis and Binding Site Topography", J. Mol. Biol., vol. 262, pp. 732-745 (1996).
Matsuda, H. et al., Int. Immunol. 9(3):461-6, 1997.
Matsushima, H. et al., J. Dermatol. Sci. 32(3):223-30, 2003.
Miller, G., "Breaking down barriers," Science 297: 1116-1118, 2002.

"Monoclonal Anti-human IL-31 Antibody", R&D Systems, Inc., Apr. 18, 2006.
Nagao, M. et al., J. Allergy Clin. Immunol. 15(2):s272, 2005.
National Cancer Institute, 1997, (GenBank Acc. No. BF152807).
National Institutes of Health, 1999, (GenBank Acc. No. CA464033).
Neis et al., "Enhanced expression levels of IL-31 correlate with IL-4 and IL-13 in atopic and allergic contact dermatitis," Journal of Allergy and Clinical Immunology, 118(4):930-937, Oct. 1, 2006.
Nobbe et al., "IL-31 expression by inflammatory cell is unique to atopic dermatitis," Abstract. Submitted to 39th Annual European Society for Dermatological Research (ESDR) Meeting (Budapest, Hungary), Sep. 9, 2009.
Nobbe et al., "IL-31 expression by inflammatory cell is unique to atopic dermatitis," Abstract. Submitted to 91st Annual Meeting of the Swiss Society of Dermatology & Venereology (Basel, Switzerland), Aug. 4, 2009.
Oostingh et al., "Autoreactive T cell response in pemphigus and pemphigoid," Autoimmun Rev. 1(5): 267-272, 2002.
Parrish-Novak, J.E. et al., Interleukin 31 is a novel four-helical-bundle cytokine that signals through a heterodimeric receptor complex expressed in epithelial cells of lung and skin, (1023) Annual Meeting of the American Society of Human Genetics, 2003.
Perrigoue et al., "IL-31-IL-31R interactions negatively regulate type 2 inflammation in the lung," Journal of Experimental Medicine 204(3): 481-487, Mar. 19, 2007.
Perrigoue et al., "IL-31-IL-31R interactions negatively regulate type 2 inflammation in the lung," J. Exp. Med. 204(3): 481-7, Mar. 19, 2007. Epub Mar. 12, 2007; PMID: 17353366 Publisher: J Exp Med.
Pettit et al., "The development of site-specific drug-delivery systems for protein and peptide biopharmaceuticals," Trends in Biotechnology 16: 343-349, 1998.
Presta et al., "Engineering of therapeutic antibodies to minimize immunogenicity and optimize function," Advanced Drug Delivery Reviews 58(5-6): 640-656, 2006.
Riken, 1999, (GenBank Acc. No. AV040649).
Riken, 1999, (GenBank Acc. No. AV044404).
Riken, 1999, (GenBank Acc. No. AV268991)8.
Riken, 1999, (GenBank Acc. No. AV280874).
Riken, 2001, (GenBank Acc. No. BB610257).
Riken, 2002, (GenBank Acc. No. BY706076).
Riken, Accession No. AK005939, 1999.
Riken, Accession No. AK005939, Jul. 5, 2001.
Robert, C. et al., N. Engl. J. Med. 341(24):1817-28, 1999.
Rudikoff, S. et al., "Single amino acid substitution altering antigen-binding specificity", Proc. Natl. Acad. Sci. USA, vol. 79, pp. 1979-1983 (1982).
Rufli et al., "T-cell subsets in acne rosacea lesions and the possible role of Demodex folliculorum," Dermatologica. 169(1): 1-5, 1984, Abstract Only.
RZPD Deutsches Ressourcenzentrum fuer Genomforschung GmbH, 2003, (GenBank Acc. No. BX639332).
Sanger Center, Mouse Public Genomic Sequence TDB 1021719, Jan. 4, 2001.
Sanger Center, Mouse Public Genomic Sequence TDB 40505897, Aug. 31, 2001.
Schulz et al., "A common haplotype of the IL-31 gene influencing gene expression is associated with nonatopic eczema," Journal of Allergy and Clinical Immunology 120(5): 1097-1102, Nov. 1, 2007.
Shimada, Y. et al., J. Dermatol. Sci. 34(3):201-8, 2004.
Singh et al., "IFN-γ-Inducible Chemokines Enhance Adaptive Immunity and Colitis," Journal of Interferon & Cytokine Research 23: 591-600, 2003.
Skolnick, J. et al., "From genes to protein structure and function: novel applications of computational approaches in the genomic era", Trends in Biotechnology, vol. 18, pp. 34-39 (2000).
SMART Domain Annotation—FN3 domain (accessed Nov. 11, 2007).
Song, T. et al., J. Allergy Clin. Immunol. 15(2):s100, 2005.
Sonkoly et al., "IL-31: A new link between t-cells and pruritus in atopic skin inflammation", Journal of Allergy and Clinical Immunology, Mosby—Yearly Book, Inc., US 117(2): 411-417, Feb. 2006.
Sprecher et al., U.S. Appl. No. 12/431,623, filed Apr. 28, 2009.
Sprecher et al., U.S. Appl. No. 12/432,286, filed Apr. 29, 2009.

(56) References Cited

OTHER PUBLICATIONS

Stander et al., "Treatment of prurigo nodularis with topical capsaicin," J Am Acad Dermatol. 44(3): 471-478, Mar. 2001, Abstract Only.
Ständer et al., Hautarzt 54: 413-417, 2003.
Steinhoff et al., "Modern aspects of cutaneous neurogenic inflammation," Archives of Dermatology 139(11): 1479-1488, Nov. 2003.
Takano, N. et al., Eur. J. Pharmacol. 471(3):223-8, 2003.
Takano, N. et al., Eur. J. Pharmacol. 495(2-3):159-65, 2004.
Takaoka, A., Eur. J. Pharmacol. PMID:15925362, 2005.
Takaoka et al., "Involvement of IL-31 on scratching behavior in NC/Nga mice with atopic-like dermatitis", Experimental Dermatology, 15 (3): 161-167, Mar. 2006.
Tamura et al., "Expression of oncostatin M receptor beta in a specific subset of nociceptive sensory neurons," European Journal of Neuroscience 14(11): 2287-2298, Jun. 2003.
Vajdos, F.F. et al., "Comprehensive Functional Maps of the Antigen-binding Site of an Anti-ErbB2 Antibody Obtained with Shotgun Scanning Mutagenesis", J. Mol. Biol., vol. 320, pp. 415-428 (2002).
Vestergaard, C. et al., J. Invest. Dermatol. 115(4):640-6, 2000.
Washington University Genome Sequencing Center, Mouse Public Genomic Sequence TDB 16727183, Feb. 24, 2001.
Washington University Genome Sequencing Center, Mouse Public Genomic Sequence TDB 8480322, Jan. 13, 2001.
Washington University Genome Sequencing Center, Mouse Public Genomic Sequence TDB 50734527, Oct. 6, 2001.
Washington University Genome Sequencing Center, Mouse Public Genomic Sequence TDB 22973884, Apr. 16, 2001.
Washington University School of Medicine, 2002, (GenBank Acc. No. CF105870).
Whitehead Institute for Biomedical Research, Mouse Public Genomic Sequence TDB 3482986, Jan. 11, 2001.
Whitehead Institute for Biomedical Research, Mouse Public Genomic Sequence TDB 10456006, Mar. 14, 2001.
Whitehead Institute for Biomedical Research, Mouse Public Genomic Sequence TDB 49775248, Oct. 5, 2001.
Whitehead Institute for Biomedical Research, Mouse Public Genomic Sequence TDB 10005090, Mar. 10, 2001.
Whitehead Institute for Biomedical Research, Mouse Public Genomic Sequence TDB 20965871, Mar. 16, 2001.
Whitehead Institute for Biomedical Research, Mouse Public Genomic Sequence TDB 44835892, Sep. 20, 2001.
Wills-Karp, M., "The gene encoding inerleukin-13: a susceptibility locus for asthma and related traits," Respiratory Research, 1(1): 19-23, Jul. 17, 2000.
Wu, H. et al., "Humanization of a Murine Monoclonal Antibody by Simultaneous Optimization of Framework and CDR Residues", J. Mol. Biol., vol. 294, pp. 151-162 (1999).
Siadak et al., U.S. Appl. No. 13/329,392, filed Dec. 19, 2011.
Yao et al., U.S. Appl. No. 13/747,899, filed Jan. 23, 2013.
Yao et al., U.S. Appl. No. 13/788,454, filed Mar. 7, 2013.
Siadak et al., U.S. Appl. No. 13/895,008, filed May 15, 2013.
Siadak et al., U.S. Appl. No. 14/498,058, filed Sep. 26, 2014.

\* cited by examiner

Alignment of humanized Anti-IL-31 molecules

N.B. CDR definitions and numbering according to Kabat / EU nomenclature

HC = heavy chain; LC = light chain; VD = variable domain

Heavy chain grafts using the human VH1-46 germline gene as acceptor

| | 10 | 20 | 30 | 40 | 50 | 60 | 70 | 80 | 90 | 110 |
|---|---|---|---|---|---|---|---|---|---|---|
| 10 | QVQLVQSGAEVKKPGASVKVSCKASGYTFTRYWMQWVRQAPGQGLEWMGAIYPGDGDTRYSQKFQGRVTMTRDTSISTVYMELSSLRSEDTAVYYCARPDGYYAAPYGMDYWGQGTLVTVSS |
| 7,9,16,17,18,26 | QVQLVQSGAEVKKPGASVKVSCKASGYTFTRYWMQWVRQAPGQGLEWMGAIYPGDGDTRYSQKFQGRVTLTADKSISTAYMELSSLRSEDTAVYYCARPDGYYAAPYGMDYWGQGTLVTVSS |
| 13 | QVQLVQSGAEVKKPGASVKVSCKASGYTLTRYWMQWVRQAPGQGLEWMGAIYPGDGDTRYSQKFQGRVTLTADKSISTAYMELSSLRSEDTAVYYCARPDGYYAAPYGMDYWGQGTLVTVSS |
| 14 | QVQLVQSGAEVKKPGASVKVSCKASGYTFTRYWMQWVRQAPGQGLEWMGAIYPGDGDTRYSQKFQGRVTLTADKSISTAYMELSSLRSEDTAVYYCAFPDGYYAAPYGMDYWGQGTLVTVSS |
| 25,35 | QVQLVQSGAEVKKPGASVKVSCKASGYTLTRYWMQWVRQAPGQGLEWMGAIYPGDGDTRYSQKFQGRVTMTRDTSISTVYMELSSLRSEDTAVYYCAFPDGYYAAPYGMDYWGQGTLVTVSS |
| 27 | QVQLVQSGAEVKKPGASVKVSCKASGYTFTRYWMQWVRQAPGQGLEWMGAIYPGDGDTRYSQKFQGRVTLTRDTSISTVYMELSSLRSEDTAVYYCAFPDGYYAAPYGMDYWGQGTLVTVSS |
| 28 | QVQLVQSGAEVKKPGASVKVSCKASGYTLTRYWMQWVRQAPGQGLEWMGAIYPGDGDTRYSQKFQGRVTMTADTSISTVYMELSSLRSEDTAVYYCAFPDGYYAAPYGMDYWGQGTLVTVSS |
| 29 | QVQLVQSGAEVKKPGASVKVSCKASGYTLTRYWMQWVRQAPGQGLEWMGAIYPGDGDTRYSQKFQGRVTMTRDKSISTVYMELSSLRSEDTAVYYCAFPDGYYAAPYGMDYWGQGTLVTVSS |
| 30 | QVQLVQSGAEVKKPGASVKVSCKASGYTLTRYWMQWVRQAPGQGLEWMGAIYPGDGDTRYSQKFQGRVTMTRDTSISTAYMELSSLRSEDTAVYYCAFPDGYYAAPYGMDYWGQGTLVTVSS |
| 31 | QVQLVQSGAEVKKPGASVKVSCKASGYTLTRYWMQWVRQAPGQGLEWMGAIYPGDGDTRYSQKFQGRVTLTADTSISTAYMELSSLRSEDTAVYYCAFPDGYYAAPYGMDYWGQGTLVTVSS |
| 32 | QVQLVQSGAEVKKPGASVKVSCKASGYTLTRYWMQWVRQAPGQGLEWMGAIYPGDGDTRYSQKFQGRVTMTADTSISTAYMELSSLRSEDTAVYYCAFPDGYYAAPYGMDYWGQGTLVTVSS |
| 33 | QVQLVQSGAEVKKPGASVKVSCKASGYTLTRYWMQWVRQAPGQGLEWMGAIYPGDGDTRYSQKFQGRVTLTADKSTSTAYMELSSLRSEDTAVYYCAFPDGYYAAPYGMDYWGQGTLVTVSS |
| 36 | QVQLVQSGAEVKKPGASVKVSCKASGYTLTRYWMQWVRQAPGQGLEWMGAIYPGDGDTRYSQKFQGRVTMTRDKSTSTVYMELSSLRSEDTAVYYCAFPDGYYAAPYGMDYWGQGTLVTVSS |
| | FR1 | | CDR1 | FR2 | CDR2 | | FR3 | | CDR3 | FR4 |

FIGURE 1a

Alignment of humanized Anti-IL-31 molecules

N.B. CDR definitions and numbering according to Kabat / EU nomenclature

HC = heavy chain; LC = light chain; VD = variable domain

Heavy chain grafts using the human VH5-51 germline gene as acceptor

```
           10        20        30        40        50        60        70        80        90        100       110
            |         |         |         |         |         |         |         |         |         |         |

21          EVQLVQSGAEVVKKPGESLKISCKASGYTLTRYWMQWVRQMPGKGLEWMGAIYPGDGTRYSPSFQGQVTISADKSISTAYLQWSSLKASDTAMYYCAFPDGYYAAPYGMDYWGQGTTVTVSS 8,11,22,23,24  EVQLVQSGAEVVKKPGESLKISCKASGYTLTRYWMQWVRQMPGKGLEWMGAIYPGDGTRYSPSFQGQVTLTADKSISTAYLQWSSLKASDTAMYYCAFPDGYYAAPYGMDYWGQGTTVTVSS
              FR1                         FR2                              FR3                                      FR4
```

FIGURE 1b

Alignment of humanized Anti-IL-31 molecules

N.B. CDR definitions and numbering according to Kabat / EU nomenclature

HC = heavy chain; LC = light chain; VD = variable domain

Light chain grafts using the human VK1-A20 germline gene as acceptor

```
                              10        20        30        40        50        60        70        80        90        100
7,8,10,13,14,21,33            DIQMTQSPSSLSASVGDRVTITCRASGNIHNYLAWYQQKPGKVPKLLIYNAKTLADGVPSRFSGSGSRSETQYSLTISSLQPEDVATYYCQHFWSTPWTFGQGTKVEIKR
9,11,34,35                    DIQMTQSPSSLSASVGDRVTITCRASGNIHNYLAWYQQKPGKVPKLLIYNAKTLADGVPSRFSGSGSGTDFTLTISSLQPEDVATYYCQHFWSTPWTFGQGTKVEIKR
16,22                         DIQMTQSPSSLSASVGDRVTITCRASGNIHNYLAWYQQKPGKVPKLLIYNAKTLADGVPSRFSGSGSRSETQFSLTISSLQPEDVATYYCQHFWSTPWTFGQGTKVEIKR
17,23                         DIQMTQSPSSLSASVGDRVTITCRASGNIHNYLAWYQQKPGKVPKLLIYNAKTLADGVPSRFSGSGSGTQYSLTISSLQPEDVATYYCQHFWSTPWTFGQGTKVEIKR
18,24                         DIQMTQSPSSLSASVGDRVTITCRASGNIHNYLAWYQQKPGKVPKLLIYNAKTLADGVPSRFSGSGSRSETDYTLTISSLQPEDVATYYCQHFWSTPWTFGQGTKVEIKR
25,26,27,28,29,30,31,32,36    DIQMTQSPSSLSASVGDRVTITCRASGNIHNYLAWYQQKPGKVPKLLIYNAKTLADGVPSRFSGSGSGTDYTLTISSLQPEDVATYYCQHFWSTPWTFGQGTKVEIKR
                              FR1                           FR2                  FR3                                     FR4
```

FIGURE 1C

POLYNUCLEOTIDES ENCODING IL-31 MONOCLONAL ANTIBODIES

CROSS-REFERENCE TO RELATED APPLICATIONS

This application is a continuation of U.S. patent application Ser. No. 13/908,436, filed Jun. 3, 2013, now U.S. Pat. No. 8,685,669, which is a divisional of U.S. patent application Ser. No. 12/329,820, filed Dec. 8, 2008, now U.S. Pat. No. 8,470,979, which claims the benefit of U.S. Provisional Application Ser. No. 61/012,362, filed Dec. 7, 2007, which are all herein incorporated by reference in their entirety.

BACKGROUND OF THE INVENTION

IL-31, a newly identified cytokine, has been found to result in dermatitis-like symptoms when over-expressed in mice. See, Dillon, et al., Nature Immunol. 5:752-760, 2004. These symptoms can be alleviated by use of antagonists that block, inhibit, reduce, antagonize or neutralize the activity of IL-31, and include anti-IL-31 antibodies. Also see, U.S. patent application Ser. No. 10/352,554, filed Jan. 21, 2003 (U.S. Patent Publication No. 2003-0224487), now U.S. Pat. Nos. 7,064, 186, 7,425,325, and 7,459,293.

Monoclonal antibody technology has provided a vast array of therapeutics as well as diagnostics for use in identifying and treating disease. A number of recombinant or biosynthetic molecules comprising rodent antigen-binding sites have been described. Particularly, molecules having rodent antigen-binding sites built directly onto human antibodies by grafting only the rodent binding site, rather than the entire variable domain, into human immunoglobulin heavy and light chain domains have been described. See, e.g., Riechmann et al. (1988) Nature 332:323-327 and Verhoeyen et al. (1988) Science 239:1534-1536. Molecules having an antigen-binding site wherein at least one of the complementarity determining regions (CDRS) of the variable domain is derived from a murine monoclonal antibody and the remaining immunoglobulin-derived parts of the molecule are derived from human immunoglobulin have been described in U.K Patent Publication No. GB 2,276,169, published Sep. 21, 1994. A number of single chain antigen-binding site polypeptides and single chain Fv (sFv) molecules have also been described. See, e.g., U.S. Pat. Nos. 5,132,405 and 5,091,513 to Huston et al.; and U.S. Pat. No. 4,946,778 to Ladner et al.

Mouse anti-human IL-31 monoclonal antibodies have been described previously in U.S. patent application Ser. No. 11/430,066, filed May 8, 2006 (U.S. Patent Publication No. 2006-02752960) that describes mouse monoclonal antibodies that recognize human IL-31 and can be used to generate chimeric antibodies. However, chimeric antibodies may cause immunogenicity and humanized mouse—anti-human IL-31 antibodies are desirable. Humanized antibodies generally have at least three potential advantages over mouse or in some cases chimeric antibodies for use in human therapy: (1) Because the effector portion is human, it may interact better with the other parts of the human immune system (e.g., destroy the target cells more efficiently by complement-dependent cytotoxicity (CDC) or antibody-dependent cellular cytotoxicity (ADCC)); (2) The human immune system should not recognize the framework or constant region of the humanized antibody as foreign, and therefore the antibody response against such an injected antibody should be less than against a totally foreign mouse antibody or a partially foreign chimeric antibody; and (3) Injected mouse antibodies have been reported to have a half-life in the human circulation much shorter than the half-life of normal antibodies (D. Shaw et al., J. Immunol., 138, 4534-4538 (1987)). Injected humanized antibodies will presumably have a half-life more similar to naturally occurring human antibodies, allowing smaller and less frequent doses to be given.

Thus, there is a need for molecules which provide humanized variable region amino acid sequences for the mouse anti-human IL-31 antibodies for treating IL-31 mediated inflammation.

SUMMARY OF THE INVENTION

In an aspect of the present invention pertains to an isolated antibody that binds to human IL-31, comprising: a) a humanized heavy chain variable domain comprising CDRs consisting of amino acid sequences SEQ ID NO: 1, 2 and 3 respectively or consisting of amino acid sequences SEQ ID NO: 1, 4 and 3 respectively; b) a humanized light chain variable domain comprising CDRs consisting of amino acid sequences of SEQ ID NO: 5, 6 and 7. In another aspect, the invention pertains to antibodies described herein wherein: a) said humanized heavy chain variable domain comprises framework regions FR1, FR2, FR3 and FR4 having an amino acid sequence at least 90% identical to the amino acid sequence selected from the group consisting of: 1) the amino acid sequence of SEQ ID NO: 8 (FR1), 9 (FR2), 10 (FR3) and 11 (FR4) respectively; 2) the amino acid sequence of SEQ ID NO: 12 (FR1), 13 (FR2), 14 (FR3) and 15 (FR4) respectively; 3) the amino acid sequence of SEQ ID NO: 12 (FR1), 13 (FR2), 16 (FR3) and 15 (FR4) respectively; and b) said humanized light chain variable domain comprises framework regions FR5, FR6, FR7, and FR8 having an amino acid sequence at least 90% identical to the amino acid sequence the framework regions are selected from the group consisting of: 1) the amino acid sequence of SEQ ID NO: 17 (FR5), 18 (FR6), 19 (FR7) and 20 (FR8) respectively; and 2) the amino acid sequence of SEQ ID NO: 17 (FR5), 18 (FR6), 21 (FR7) and 20 (FR8) respectively. In an embodiment, said identity is at least 95%, even more preferably at least 98%, most preferably at least 99%.

In another aspect the invention pertains to an isolated antibody as described herein wherein amino acid at position 29 in FR1 of the heavy chain is leucine and amino acid at position 32 in FR3 of the heavy chain is phenylalanine. In another aspect the invention pertains to an isolated antibody as described herein wherein amino acid at position 8 in FR3 of the heavy chain is lysine and amino acid at position 15 in FR7 of the light chain is tyrosine.

In a further aspect the present invention pertains to an isolated antibody that binds to human IL-31, comprising: a) a humanized heavy chain variable domain comprising CDR1 and CDR3 having amino acid sequence of SEQ ID NO: 1 and 3 respectively and CDR2 having amino acid sequence of AIYPGDGDTRYSXaa1Xaa2FXaa3G (SEQ ID NO: 22) wherein Xaa1 is glutamine or proline, Xaa2 is serine or lysine and Xaa3 is glutamine or lysine; said humanized heavy chain variable domain comprising framework regions FR1, FR2, FR3 and FR4 having an amino acid sequence at least 90% identical to the amino acid sequence of: SEQ ID NO: 8, 9, 10 and 11 respectively, or SEQ ID NO: 12, 13, 14 and 15 respectively, or SEQ ID NO: 12, 13, 16 and 15 respectively; and with the proviso that amino acid at position 29 in FR1 is leucine and amino acid at position 32 in FR3 is phenylalanine; b) a humanized light chain variable domain comprising CDRs consisting of amino acid sequences of SEQ ID NO: 5, 6 and 7 said humanized light chain variable domain comprising framework regions FR5, FR6, FR7 and FR8 having an amino acid sequence at least 90% identical to the amino acid sequence of SEQ ID NO: 17, 18, 19 and 20 respectively, or at least 90% identical to the amino acid sequence of SEQ ID NO: 17, 18, 21 and 20 respectively. In a aspect of the present invention, said identity is at least 95%, even more preferably at least 98%, most preferably at least 99%. In another aspect the invention pertains to an isolated antibody as described herein wherein amino acid at position 8 in FR3 of the heavy chain is lysine and amino acid at position 15 in FR7 of the light chain is tyrosine. In another aspect the invention pertains to an isolated antibody as described herein wherein: amino acid Xaa1 is glutamine, Xaa2 is lysine and Xaa3 is lysine; amino acid Xaa1 is proline, Xaa2 is serine and Xaa3 is glutamine; or amino acid Xaa1 is glutamine, Xaa2 is lysine and Xaa3 is glutamine.

In another aspect the invention pertains to an isolated antibody as described herein wherein CDRs of the heavy chain variable domain consist of SEQ ID NO: 1, 4 and 3 respectively, CDRs of the light chain variable domain consist of SEQ ID NO: 5, 6 and 7 respectively, framework regions of the heavy chain variable domain consist of SEQ ID NO: 8, 9, 10 and 11 respectively, and framework regions of the light chain variable domain consist of SEQ ID NO: 17, 18, 19 and 20 respectively.

In another aspect the invention pertains to an isolated antibody as described herein wherein CDRs of the heavy chain variable domain consist of SEQ ID NO: 1, 2 and 3 respectively, CDRs of the light chain variable domain consist of SEQ ID NO: 5, 6 and 7 respectively, framework regions of the heavy chain variable domain consist of SEQ ID NO: 12, 13, 14 and 15 respectively, and framework regions of the light chain variable domain consist of SEQ ID NO: 17, 18, 19 and 20 respectively.

In another aspect the invention pertains to an isolated antibody as described herein wherein CDRs of the heavy chain variable domain consist of SEQ ID NO: 1, 2 and 3 respectively, CDRs of the light chain variable domain consist of SEQ ID NO: 5, 6 and 7 respectively, framework regions of the heavy chain variable domain consist of SEQ ID NO: 12, 13, 16 and 15 respectively, and framework regions of the light chain variable domain consist of SEQ ID NO: 17, 18, 21 and 20 respectively.

As it will be shown from the Examples and teachings herein, the presence of both a leucine at position 29 in FR1 and a phenylalanine at position 32 in FR3 of the humanized antibodies described herein, has a positive impact in terms of affinity and potency of said antibodies. As shown for example in a Biacore assay, the binding affinity of humanized antibodies bearing both a leucine at position 29 in FR1 and a phenylalanine at position 32 in FR3 is better when compared to humanized antibodies which bear another amino acid at these positions (compare for example clones number 7, 10, 13 and 14 in Table 2 of Example 3). The positive impact of these amino acids at position 29 of FR1 and 94 of FR3 of the heavy chain, both in terms of affinity and potency, has also been confirmed by two other biological tests (see Examples 4 and 5).

In an embodiment of the present invention, the antibody disclosed herein comprises a heavy chain immunoglobulin constant domain selected from the group consisting of the constant region of an α, γ, μ, δ or ε human immunoglobulin heavy chain. In a embodiment of the present invention, the antibody disclosed herein comprises a heavy chain immunoglobulin constant domain selected from the group consisting of a human IgG1 constant domain; a human IgG2 constant domain; a human IgG3 constant domain; a human IgG4 constant domain; a human IgM constant domain; a human IgE constant domain and a human IgA constant domain. In an embodiment, the human IgG4 constant domain is a mutated form stable in solution and with little or no complement activating activity. In an embodiment, the heavy chain immunoglobulin constant region domain is a human IgG4 constant domain with a Ser to Pro mutation at position 241 (Kabat numbering).

In an embodiment, the immunoglobulin light chain constant region domain is selected from the group consisting of the constant region of a κ or λ human immunoglobulin light chain. Preferably, the immunoglobulin light chain constant region domain is the constant region of a κ human immunoglobulin light chain.

BRIEF DESCRIPTION OF THE DRAWINGS

FIG. 1a shows an alignment of heavy chain anti-human IL-31 antibody sequences using the human VH1-46 germline gene as acceptor.

FIG. 1b shows an alignment of heavy chain anti-human IL-31 antibody sequences using the human VH5-51 germline as acceptor.

FIG. 1c shows an alignment of light chain anti-human IL-31 antibody sequences using the human VK1-A20 germline as acceptor. The amino acid sequences of the clones shown in FIGS. 1a-1c are listed in Table 1.

DETAILED DESCRIPTION OF THE INVENTION

Prior to setting forth the invention in detail, it may be helpful to the understanding thereof to define the following terms:

As used herein, the term "antibodies" includes polyclonal antibodies, affinity-purified polyclonal antibodies, monoclonal antibodies, and antigen-binding fragments, such as F(ab')$_2$, Fab proteolytic fragments, and single chain variable region fragments (scFvs). Genetically engineered intact antibodies or fragments, such as chimeric antibodies, Fv fragments, single chain antibodies and the like, as well as synthetic antigen-binding peptides and polypeptides, are also included. Non-human antibodies may be humanized by grafting non-human CDRs onto human framework and constant regions, or by incorporating the entire non-human variable domains (optionally "cloaking" them with a human-like surface by replacement of exposed residues, wherein the result is a "veneered" antibody). In some instances, humanized antibodies may retain non-human residues within the human variable region framework domains to enhance proper binding characteristics. Through humanizing antibodies, biological half-life may be increased, and the potential for adverse immune reactions upon administration to humans is reduced.

The term "chimeric antibody" or "chimeric antibodies" refers to antibodies whose light and heavy chain genes have been constructed, typically by genetic engineering, from immunoglobulin variable and constant region genes belonging to different species. For example, the variable segments of the genes from a mouse monoclonal antibody may be joined to human constant segments, such as gamma 1 and gamma 3. A typical therapeutic chimeric antibody is thus a hybrid protein composed of the variable or antigen-binding domain from a mouse antibody and the constant domain from a human antibody, although other mammalian species may be used.

As used herein, the term "immunoglobulin" refers to a protein consisting of one or more polypeptides substantially encoded by immunoglobulin genes. One form of immunoglobulin constitutes the basic structural unit of an antibody.

This form is a tetramer and consists of two identical pairs of immunoglobulin chains, each pair having one light and one heavy chain. In each pair, the light and heavy chain variable regions are together responsible for binding to an antigen, and the constant regions are responsible for the antibody effector functions.

Full-length immunoglobulin "light chains" (about 25 Kd or 214 amino acids) are encoded by a variable region gene at the NH2-terminus (about 110 amino acids) and a kappa or lambda constant region gene at the COOH— terminus. Full-length immunoglobulin "heavy chains" (about 50 Kd or 446 amino acids), are similarly encoded by a variable region gene (about 116 amino acids) and one of the other aforementioned constant region genes (about 330 amino acids). Heavy chains are classified as gamma, mu, alpha, delta, or epsilon, and define the antibody's isotype as IgG, IgM, IgA, IgD and IgE, respectively. Within light and heavy chains, the variable and constant regions are joined by a "J" region of about 12 or more amino acids, with the heavy chain also including a "D" region of about 10 more amino acids. (See generally, Fundamental Immunology (Paul, W., ed., 2nd ed. Raven Press, N.Y., 1989), Ch. 7 (incorporated herein by reference its disclosure on producing antibodies and antibody fragments).

An immunoglobulin light or heavy chain variable region consists of a "framework" region interrupted by three hyper-variable regions. Thus, the term "hypervariable region" refers to the amino acid residues of an antibody which are responsible for antigen binding. The hypervariable region comprises amino acid residues from a "Complementarity Determining Region" or "CDR" (i.e., residues 24-34 (L1), 50-56 (L2) and 89-97 (L3) in the light chain variable domain and 31-35 (H1), 50-65 (H2) and 95-102 (H3) in the heavy chain variable domain (Kabat et al., Sequences of Proteins of Immunological Interest, 5th Ed. Public Health Service, National Institutes of Health, Bethesda, Md. (1991)) and/or those residues from a "hypervariable loop" (i.e., residues 26-32 (L1), 50-52 (L2) and 91-96 (L3) in the light chain variable domain and 26-32 (H1), 53-55 (H2) and 96-101 (H3) in the heavy chain variable domain; Chothia and Lesk, 1987, J. Mol. Biol. 196: 901-917) (both of which are incorporated herein by reference). "Framework Region" or "FR" residues are those variable domain residues other than the hypervariable region residues as herein defined. The sequences of the framework regions of different light or heavy chains are relatively conserved within a species. Thus, a "human framework region" is a framework region that is substantially identical (about 85% or more, usually 90-95% or more) to the framework region of a naturally occurring human immunoglobulin. The framework region of an antibody, that is the combined framework regions of the constituent light and heavy chains, serves to position and align the CDR's. The CDR's are primarily responsible for binding to an epitope of an antigen.

Accordingly, the term "humanized" immunoglobulin refers to an immunoglobulin comprising a human framework region and one or more CDR's from a non-human (usually a mouse or rat) immunoglobulin. The non-human immunoglobulin providing the CDR's is called the "donor" and the human immunoglobulin providing the framework is called the "acceptor". Constant regions need not be present, but if they are, they must be substantially identical to human immunoglobulin constant regions, i.e., at least about 85-90%, preferably about 95% or more identical. Hence, all parts of a humanized immunoglobulin, except possibly the CDR's, are substantially identical to corresponding parts of natural human immunoglobulin sequences. A "humanized antibody" is an antibody comprising a humanized light chain and a humanized heavy chain immunoglobulin. For example, a humanized antibody would not encompass a typical chimeric antibody as defined above, e.g., because the entire variable region of a chimeric antibody is non-human.

The term "recombinant antibodies" means antibodies wherein the amino acid sequence has been varied from that of a native antibody. Because of the relevance of recombinant DNA techniques in the generation of antibodies, one need not be confined to the sequences of amino acids found in natural antibodies; antibodies can be redesigned to obtain desired characteristics. The possible variations are many and range from the changing of just one or a few amino acids to the complete redesign of, for example, the variable or constant region. Changes in the constant region will, in general, be made in order to improve or alter characteristics, such as complement fixation, interaction with membranes and other effector functions. Changes in the variable region will be made in order to improve the antigen binding characteristics.

In addition to antibodies, immunoglobulins may exist in a variety of other forms including, for example, single-chain or Fv, Fab, and (Fab')$_2$, as well as diabodies, linear antibodies, multivalent or multispecific hybrid antibodies (as described above and in detail in: Lanzavecchia et al., Eur. J. Immunol. 17, 105 (1987)) and in single chains (e.g., Huston et al., Proc. Natl. Acad. Sci. U.S.A., 85, 5879-5883 (1988) and Bird et al., Science, 242, 423-426 (1988), which are incorporated herein by reference for their teachings on antibody fragments). (See, generally, Hood et al., "Immunology", Benjamin, N.Y., 2nd ed. (1984), and Hunkapiller and Hood, Nature, 323, 15-16 (1986), which are incorporated herein by reference for antibodies).

As used herein, the terms "single-chain Fv," "single-chain antibodies," "Fv" or "scFv" refer to antibody fragments that comprises the variable regions from both the heavy and light chains, but lacks the constant regions, but within a single polypeptide chain. Generally, a single-chain antibody further comprises a polypeptide linker between the VH and VL domains which enables it to form the desired structure which would allow for antigen binding. Single chain antibodies are discussed in detail by Pluckthun in The Pharmacology of Monoclonal Antibodies, vol. 113, Rosenburg and Moore eds. Springer-Verlag, New York, pp. 269-315 (1994); see also International Patent Application Publication No. WO 88/01649 and U.S. Pat. Nos. 4,946,778 and 5,260,203, the disclosures of which are incorporated by reference for any purpose. In specific embodiments, single-chain antibodies can also be bi-specific and/or humanized.

A "Fab fragment" is comprised of one light chain and the $C_{H1}$ and variable regions of one heavy chain. The heavy chain of a Fab molecule cannot form a disulfide bond with another heavy chain molecule.

A "Fab' fragment" contains one light chain and one heavy chain that contains more of the constant region, between the $C_{H1}$ and $C_{H2}$ domains, such that an interchain disulfide bond can be formed between two heavy chains to form a F(ab')$_2$ molecule.

A "F(ab')$_2$ fragment" contains two light chains and two heavy chains containing a portion of the constant region between the $C_{H1}$ and $C_{H2}$ domains, such that an interchain disulfide bond is formed between two heavy chains.

Molecular weights and lengths of polymers determined by imprecise analytical methods (e.g., gel electrophoresis) will be understood to be approximate values. When such a value is expressed as "about" X or "approximately" X, the stated value of X will be understood to be accurate to ±10%.

All references cited herein are incorporated by reference in their entirety.

The present invention is based upon the discovery of humanized mouse anti-human IL-31 variable region sequences of antibodies. Use of these antibodies as antagonists to IL-31 can inhibit inflammation in general, and the symptoms of dermatitis and pruritic diseases in specific. The invention provides the use of humanized light chain and heavy chain regions of antibodies that recognize, bind, and/or neutralize the IL-31 polypeptide. Such humanized light and heavy chain regions can be fused to an immunoglobulin constant region, such as for example, IgG4 or IgG1, and expressed in a variety of host cells. The humanized anti-IL-31 variable region sequences described herein were generated using amino acid sequences of mouse anti-human IL-31 light chain and heavy chain variable regions of monoclonal antibodies previously described in U.S. patent application Ser. No. 11/430,066, filed May 8, 2006 (U.S. Patent Publication No. 2006-02752960), herein incorporated by reference.

Antibodies can comprise antibodies or antibody fragments, comprising or consisting of a light chain variable region and a heavy chain variable region, and can be chimeric, humanized, or antibody fragments that neutralize, inhibit, reduce, prevent or minimize the effects of IL-31 on its receptor. Clinical outcomes of the antibody or antibody fragments can be a reduction in inflammatory and autoimmune diseases, such as dermatitis, in particular atopic dermatitis, and pruritic diseases and Crohn's disease, as further described herein. In an embodiment, the dermatitis is atopic dermatitis. In another embodiment the dermatitis is prurigo nodularis. In another embodiment, the dermatitis is eczema. The reduction may also be a reduction in itch, scratching, or hairloss.

IL-31 is a newly discovered T cell cytokine which, when over-expressed in mice, results in dermatitis-like symptoms. See, Dillon, et al., Nature Immunol. 5:752-760, 2004. IL-31 is the HUGO name for a cytokine that has been previously described as Zcyto17rlig in U.S. patent application Ser. No. 10/352,554, filed Jan. 21, 2003 (U.S. Patent Publication No. 2003-0224487), now U.S. Pat. No. 7,064,186, Sprecher, Cindy et al., 2003, incorporated herein by reference). See also, Dillon, et al., Nature Immunol., supra. The amino acid sequence of human IL-31 is shown in SEQ ID NO: 24. Tissue analysis revealed that expression of mouse IL-31 is found in testis, brain, CD90+ cells, prostate cells, salivary gland and skin.

The heterodimeric receptor for IL-31 was described in U.S. Patent Publication No. 20030224487 as zcytor17 (HUGO name, IL-31RA) which forms a heterodimer with OncostatinM receptor beta (OSMRbeta). IL-31 was isolated from a cDNA library generated from activated human peripheral blood cells (hPBCs), which were selected for CD3. CD3 is a cell surface marker unique to cells of lymphoid origin, particularly T cells.

Inhibition, neutralization, or blocking signal transduction by the molecules comprising a humanized mouse anti-human light chain variable domain and/or a humanised mouse anti-human heavy chain variable domain, termed "IL-31 antigen binding molecules" or "IL-31 antagonists" herein, can be measured by a number of assays known to one skilled in the art. For example, assays measuring a reduction in proliferation include assays for reduction of a dye such as AlamarBlue™ (AccuMed International, Inc. Westlake, Ohio), 3-(4, 5-dimethylthiazol-2-yl)-2,5-diphenyl tetrazolium bromide (Mosman, *J. Immunol. Meth.* 65: 55-63, 1983); 3,(4,5 dimethyl thiazol-2-yl)-5-3-carboxymethoxyphenyl-2H-tetrazolium; 2,3-bis(2-methoxy-4-nitro-5-sulfophenyl)-5-[(phenylamino)carbonyl]-2H-tetrazolium hydroxide; and cyanoditolyl-tetrazolium chloride (which are commercially available from Polysciences, Inc., Warrington, Pa.); mitogenesis assays, such as measurement of incorporation of $^3$H-thymidine; dye exclusion assays using, for example, naphthalene black or trypan blue; dye uptake using diacetyl fluorescein; and chromium release. See, in general, Freshney, *Culture of Animal Cells: A Manual of Basic Technique*, 3rd ed., Wiley-Liss, 1994, which is incorporated herein by reference. In addition to the above, see published U.S. patent publication number 20030224487, (Sprecher, Cindy et al., 2003) for an example of BaF3 cells expressing IL-31RA and full-length OSMRbeta or as shown in the activity examples described herein.

Methods for preparing the polynucleotides encoding the antibodies described herin (including DNA and RNA) are well known in the art. Total RNA can be prepared using guanidinium isothiocyanate extraction followed by isolation by centrifugation in a CsCl gradient (Chirgwin et al., *Biochemistry* 18:52-94, 1979). Poly (A)$^+$ RNA is prepared from total RNA using the method of Aviv and Leder (*Proc. Natl. Acad. Sci. USA* 69:1408-12, 1972). Complementary DNA (cDNA) is prepared from poly(A)$^+$ RNA using known methods. In the alternative, genomic DNA can be isolated. Polynucleotides encoding IL-31 antibodies are then identified and isolated by, for example, hybridization or PCR.

The present invention also includes humanized IL-31 antigen binding molecules or IL-31 antagonists that bind functional fragments of IL-31 polypeptides and nucleic acid molecules encoding such functional fragments. A "functional" IL-31 or fragment thereof as defined herein is characterized by its proliferative or differentiating activity, by its ability to induce or inhibit specialized cell functions, or by its ability to bind specifically to an anti-IL-31 antibody or IL-31RA/OSMRbeta heterodimers of these receptors (either soluble or immobilized). Thus, the present invention further provides humanized IL-31 antigen binding molecules or IL-31 antagonists that bind a polypeptide molecule comprising one or more IL-31 functional fragments.

The present invention also provides humanized IL-31 antigen binding molecules or IL-31 antagonists that bind to polypeptide fragments or peptides comprising an epitope-bearing portion of a IL-31 polypeptide or an immunogenic epitope or antigenic epitope. The binding of the antibodies to these epitopes results in inhibition, blocking, neutralization, and/or reduction in signal transduction of IL-31 on its cognate receptor.

Mouse anti-human IL-31 monoclonal antibodies have been previously described in co-pending U.S. patent application Ser. No. 11/430,066, filed May 8, 2006 (U.S. Patent Publication No. 2006-02752960). The amino acid sequences of the variable regions of mouse anti-human IL-31 antibodies described in co-pending U.S. patent application Ser. No. 11/850,006, filed Sep. 4, 2007 and co-owned PCT application U.S.07/77555, filed Sep. 4, 2007, both of which are incorporated by reference herein for the variable region sequences and antibody production methods. These amino acid sequences were used as starting material for the humanized sequences described herein. In specific, the mouse anti-human IL-31 antibody sequence was from a hybridoma with the clone number 292.12.3.1.

The activity of the antibodies as described herein can be measured by their ability to inhibit, or reduce proliferation using a variety of assays that measure proliferation of and/or binding to cells expressing the IL-31RA receptor. Of particular interest are changes in IL-31-dependent cells. Suitable cell lines to be engineered to be IL-31-dependent include the IL-3-dependent BaF3 cell line (Palacios and Steinmetz, *Cell* 41: 727-734, 1985; Mathey-Prevot et al., *Mol. Cell. Biol.* 6: 4133-4135, 1986), FDC-P1 (Hapel et al., *Blood* 64: 786-790, 1984), and MO7e (Kiss et al., *Leukemia* 7: 235-240, 1993). Growth factor-dependent cell lines can be established according to published methods (e.g. Greenberger et al., *Leukemia Res.* 8: 363-375, 1984; Dexter et al., in Baum et al. Eds., *Experimental Hematology Today,* 8th Ann. Mtg. Int. Soc. Exp. Hematol. 1979, 145-156, 1980). The activity of the humanized anti-IL-31 antibodies or antagonists can also be measured in the BaF3 proliferation assay, the Biacore assay, or the NHK assays described herein.

In an embodiment, the immunoglobulin heavy chain constant region domain is selected from the group consisting of the constant region of an α, γ, μ, δ or ε human immunoglobulin heavy chain. Said constant region can be the constant region of a γ1, γ2, γ3 or γ4 human immunoglobulin heavy chain.

In another embodiment, the immunoglobulin light chain constant region domain is selected from the group consisting of the constant region of a κ or λ human immunoglobulin light chain.

In another embodiment, the heavy constant chain is human γ4, which is stable in solution and has little or no complement activating activity. In another embodiment, the heavy constant chain is human γ1.

The immunoglobulin may be selected from any of the major classes of immunoglobulins, including IgA, IgD, IgE, IgG and IgM, and any subclass or isotype, e.g. IgG1, IgG2, IgG3 and IgG4; IgA-1 and IgA-2.

Inhibition the activity of IL-31 can be measured by a number of assays. In addition to those assays disclosed herein, samples can be tested for inhibition of IL-31 activity within a variety of assays designed to measure receptor binding, the stimulation/inhibition of IL-31-dependent cellular responses or proliferation of IL-31RA receptor-expressing cells.

A IL-31-binding polypeptide, including IL-31 antigen binding molecules or IL-31 antagonists can also be used for purification of ligand. The polypeptide is immobilized on a solid support, such as beads of agarose, cross-linked agarose, glass, cellulosic resins, silica-based resins, polystyrene, cross-linked polyacrylamide, or like materials that are stable under the conditions of use. Methods for linking polypeptides to solid supports are known in the art, and include amine chemistry, cyanogen bromide activation, N-hydroxysuccinimide activation, epoxide activation, sulfhydryl activation, and hydrazide activation. The resulting medium will generally be configured in the form of a column, and fluids containing ligand are passed through the column one or more times to allow ligand to bind to the receptor polypeptide. The ligand is then eluted using changes in salt concentration, chaotropic agents (guanidine HCl), or pH to disrupt ligand-receptor binding.

Humanized IL-31 antigen binding molecules or IL-31 antagonists are considered to be specifically binding if: 1) they exhibit a threshold level of binding activity, and 2) they do not significantly cross-react with related polypeptide molecules. A threshold level of binding is determined if IL-31 antigen binding molecules or IL-31 antagonists herein bind to a IL-31 polypeptide, peptide or epitope with an affinity at least 10-fold greater than the binding affinity to control (non-IL-31) polypeptide. It is preferred that the antibodies exhibit a binding affinity ($K_a$) of $10^6$ $M^{-1}$ or greater, preferably $10^7$ $M^{-1}$ or greater, more preferably $10^8$ $M^{-1}$ or greater, and most preferably $10^9$ $M^{-1}$ or greater. The binding affinity of humanized IL-31 antigen binding molecules or IL-31 antagonists can be readily determined by one of ordinary skill in the art, for example, by Scatchard analysis (Scatchard, G., *Ann. N.Y. Acad. Sci.* 51: 660-672, 1949).

Whether IL-31 antigen binding molecules or IL-31 antagonists do not significantly cross-react with related polypeptide molecules is shown, for example, by the IL-31 antigen binding molecules or IL-31 antagonists detecting IL-31 polypeptide but not known related polypeptides using a standard Western blot analysis (Ausubel et al., *ibid.*). Screening can also be done using non-human IL-31, and IL-31 mutant polypeptides. Moreover, IL-31 antigen binding molecules or IL-31 antagonists can be "screened against" known related polypeptides, to isolate a population that specifically binds to the IL-31 polypeptides. For example, IL-31 antigen binding molecules or IL-31 antagonists are adsorbed to related polypeptides adhered to insoluble matrix; IL-31 antigen binding molecules or IL-31 antagonists specific to IL-31 will flow through the matrix under the proper buffer conditions. *Antibodies: A Laboratory Manual*, Harlow and Lane (eds.), Cold Spring Harbor Laboratory Press, 1988; *Current Protocols in Immunology*, Cooligan, et al. (eds.), National Institutes of Health, John Wiley and Sons, Inc., 1995.

Humanized IL-31 antigen binding molecules or IL-31 antagonists are characterized for their ability to block, inhibit, prevent, or reduce receptor binding when grown in the presence of the purified recombinant proteins human IL-31. For example, the humanized IL-31 antigen binding molecules or IL-31 antagonists can be characterized in a number of ways including binning (i.e, determining if each antibody could inhibit the binding of any other binding), relative affinity, and neutralization.

The humanized IL-31 antigen binding molecules or IL-31 antagonists of the invention are shown in Table 1, below, and in FIG. 1.

In Table 1, below, for the clones having the designation of "12VH1" (i.e., clones 7, 9, 10, 13-18, and 26-36): the term "fback" means LC(back)+HC(fback); the term "LC(back)" means LC(G66R, G68E, D70Q, F71Y, T72S); and the term "HC(back)" means HC(F29L, M69L, R71A, T73K, V78A, R94F). Similarly, in Table 1, below for the clones having the designation of "12VH5" (i.e., clones 8, 11 and 21-24): the term "fback" means LC(back)+HC(fback); the term "LC (back)" means LC(G66R, G68E, D70Q, F71Y, T72S); and the term "HC(back)" means HC(G24A, S28T, F29L, I69L, S70T, R94F).

TABLE 1

Humanized 292.12.3.1 constructs

| Clone Number | Mutation Description | Heavy Chain SEQ ID NO: | Light Chain SEQ ID NO: |
|---|---|---|---|
| 7 | 12VH1-gly + fback | 25 | 26 |
| 8 | 12VH5-gly + fback | 27 | 26 |
| 9 | 12VH1-gly + HC(fback) | 25 | 28 |

TABLE 1-continued

Humanized 292.12.3.1 constructs

| Clone Number | Mutation Description | Heavy Chain SEQ ID NO: | Light Chain SEQ ID NO: |
|---|---|---|---|
| 10 | 12VH1-gly + LC(fback) | 29 | 26 |
| 11 | 12VH5-gly + HC(fback) | 27 | 28 |
| 13 | 12VH1-gly + HC(F29L, M69L, R71A, T73K, V78A) + LC(fback) | 30 | 26 |
| 14 | 12VH1-gly + HC(M69L, R71A, T73K, V78A, R94F) + LC(fback) | 31 | 26 |
| 16 | 12VH1-gly + HC(fback) + LC(G66R, G68E, D70Q, T72S) | 25 | 32 |
| 17 | 12VH1-gly + HC(fback) + LC(D70Q, F71Y, T72S) | 25 | 33 |
| 18 | 12VH1-gly + HC(fback) + LC(G66R, G68E, F71Y) | 25 | 34 |
| 21 | 12VH5-gly + HC(G24A, S28T, F29L, R94F) + LC(fback) | 35 | 26 |
| 22 | 12VH5-gly + HC(fback) + LC(G66R, G68E, D70Q, T72S) | 27 | 32 |
| 23 | 12VH5-gly + HC(fback) + LC(D70Q, F71Y, T72S) | 27 | 33 |
| 24 | 12VH5-gly + HC(fback) + LC(G66R, G68E, F71Y) | 27 | 34 |
| 25 | 12VH1-gly + HC(F29L, R94F) + LC(F71Y) | 36 | 37 |
| 26 | 12VH1-gly + HC(fback) + LC(F71Y) | 25 | 37 |
| 27 | 12VH1-gly + HC(F29L, M69L, R94F) + LC(F71Y) | 38 | 37 |
| 28 | 12VH1-gly + HC(F29L, R71A, R94F) + LC(F71Y) | 39 | 37 |
| 29 | 12VH1-gly + HC(F29L, T73K, R94F) + LC(F71Y) | 40 | 37 |
| 30 | 12VH1-gly + HC(F29L, V78A, R94F) + LC(F71Y) | 41 | 37 |
| 31 | 12VH1-gly + HC(F29L, M69L, R71A, V78A, R94F) + LC(F71Y) | 42 | 37 |
| 32 | 12VH1-gly + HC(F29L, R71A, V78A, R94F) + LC(F71Y) | 43 | 37 |
| 33 | 12VH1(germ)-gly + fback | 44 | 26 |
| 34 | 12VH1-gly + HC(F29L, R94F) + LC(fback) | 36 | 28 |
| 35 | 12VH1-gly + HC(F29L, R94F) | 36 | 28 |
| 36 | 12VH1(germ)-gly + HC(F29L, T73K, R94F) + LC(F71Y) | 45 | 37 |

The antibodies disclosed herein may be produced by any technique known per se in the art, such as by recombinant technologies, chemical synthesis, cloning, ligations, or combinations thereof. In a embodiment, the antibodies of the present invention are produced by recombinant technologies, e.g., by expression of a corresponding nucleic acid in a suitable host cell. The polypeptide produced may be glycosylated or not, or may contain other post-translational modifications depending on the host cell type used. Many books and reviews provide teachings on how to clone and produce recombinant proteins using vectors and prokaryotic or eukaryotic host cells, such as some titles in the series "A Practical Approach" published by Oxford University Press ("DNA Cloning 2: Expression Systems", 1995; "DNA Cloning 4: Mammalian Systems", 1996; "Protein Expression", 1999; "Protein Purification Techniques", 2001).

A further object of the present invention is therefore an isolated nucleic acid molecule encoding any of the antibodies here above or below described, or a complementary strand or degenerate sequence thereof. In this regard, the term "nucleic acid molecule" encompasses all different types of nucleic acids, including without limitation deoxyribonucleic acids (e.g., DNA, cDNA, gDNA, synthetic DNA, etc.), ribonucleic acids (e.g., RNA, mRNA, etc.) and peptide nucleic acids (PNA). In a preferred embodiment, the nucleic acid molecule is a DNA molecule, such as a double-stranded DNA molecule or a cDNA molecule. The term "isolated" means nucleic acid molecules that have been identified and separated from at least one contaminant nucleic acid molecule with which it is ordinarily associated in the natural source. An isolated nucleic acid molecule is other than in the form or setting in which it is found in nature. Isolated nucleic acid molecules therefore are distinguished from the specific nucleic acid molecule as it exists in natural cells. A degenerate sequence designates any nucleotide sequence encoding the same amino acid sequence as a reference nucleotide sequence, but comprising a distinct nucleotide sequence as a result of the genetic code degeneracy.

A further object of this invention is a vector comprising DNA encoding any of the above or below described antibodies. The vector may be any cloning or expression vector, integrative or autonomously replicating, functional in any prokaryotic or eukaryotic cell. In particular, the vector may be a plasmid, cosmid, virus, phage, episome, artificial chromosome, and the like. The vector may comprise the coding sequences for both the heavy and light chain, or either of the light and heavy chain coding sequences. Should the vector comprise coding sequences for both heavy and light chains, the heavy and light chains may each be operably linked to a promoter. The promoter may be the same or different for the heavy and light chain. The heavy and light chain may also be operably linked to one single promoter, in this case the coding sequences for the heavy and light chains may preferably be separated by an internal ribosomal entry site (IRES). Suitable promoters for eukaryotic gene expression are, for example, promoters derived from viral genes such as the murine or human cytomegalovirus (CMV) or the rous sarcoma virus (RSV) promoter, which are well known to the person skilled in the art. The vector may comprise regulatory elements, such as a promoter, terminator, enhancer, selection marker, origin of replication, etc. Specific examples of such vectors include prokaryotic plasmids, such as pBR, pUC or pcDNA plasmids; viral vectors, including retroviral, adenoviral or AAV vectors; bacteriophages; baculoviruses; BAC or YAC, etc., as will be discussed below. The appropriate nucleic acid sequence may be inserted into the vector by a variety of procedures. In general, DNA is inserted into an appropriate restriction endonuclease site(s) using techniques known in the art. Construction of suitable vectors containing one or more of these components employs standard ligation techniques which are known to the skilled artisan.

A further aspect of the present invention is a recombinant host cell, wherein said cell comprises a nucleic acid molecule or a vector as defined above. The host cell may be a prokaryotic or eukaryotic cell. Examples of prokaryotic cells include bacteria, such as *E. coli*. Examples of eucaryotic cells are yeast cells, plant cells, mammalian cells and insect cells including any primary cell culture or established cell line (e.g., 3T3, Véro, HEK293, TN5, etc.). Suitable host cells for the expression of glycosylated proteins are derived from multicellular organisms. Examples of invertebrate cells include insect cells such as *Drosophila* S2 and *Spodoptera* Sf9, as well as plant cells. Examples of useful mammalian host cell lines include Chinese hamster ovary (CHO) and COS cells. More specific examples include monkey kidney CV1 line transformed by SV40 (COS-7, ATCC CRL 1651); human embryonic kidney line (293 or 293 cells subcloned for growth in suspension culture, Graham et al., J. Gen Virol., 36:59 (1977)); Chinese hamster ovary cells/–DHFR(CHO, Urlaub and Chasin, Proc. Natl, Acad. Sci. USA, 77:4216 (1980)); mouse sertoli cells (TM4, Mather, Biol. Reprod., 23:243-251 (1980)); human lung cells (W138, ATCC CCL 75); human liver cells (Hep G2, HB 8065); and mouse mammary tumor (MMT 060562, ATCC CCL51). Particularly preferred mammalian cells of the present invention are CHO cells. Further particularly preferred mammalian cells suitable for expression of the antibodies of the invention are murine cells, such as mouse myeloma (NS0) cells.

As disclosed here above, the antibodies of the present invention may be produced by any technique known per se in the art, such as by recombinant technologies, chemical synthesis, cloning, ligations, or combinations thereof. In a particular embodiment, the soluble receptors are produced by recombinant technologies, e.g., by expression of a corresponding nucleic acid in a suitable host cell. Another object of this invention is therefore a method of producing an antibody of the present invention, the method comprising culturing a recombinant host cell of the invention under conditions allowing expression of the nucleic acid molecule, and recovering the polypeptide produced. The method of producing of the present invention may further comprise the step of formulating the polypeptide into a pharmaceutical composition. The polypeptide produced may be glycosylated or not, or may contain other post-translational modifications depending on the host cell type used. Many books and reviews provide teachings on how to clone and produce recombinant proteins using vectors and prokaryotic or eukaryotic host cells, such as some titles in the series "A Practical Approach" published by Oxford University Press ("DNA Cloning 2: Expression Systems", 1995; "DNA Cloning 4: Mammalian Systems", 1996; "Protein Expression", 1999; "Protein Purification Techniques", 2001).

The vectors to be used in the method of producing an antibody according to the present invention can be episomal or non-/homologously integrating vectors, which can be introduced into the appropriate host cells by any suitable means (transformation, transfection, conjugation, protoplast fusion, electroporation, calcium phosphate-precipitation, direct microinjection, etc.). Factors of importance in selecting a particular plasmid, viral or retroviral vector include: the ease with which recipient cells that contain the vector may be recognized and selected from those recipient cells which do not contain the vector; the number of copies of the vector which are desired in a particular host; and whether it is desirable to be able to "shuttle" the vector between host cells of different species. The vectors should allow the expression of the polypeptide or fusion proteins of the invention in prokaryotic or eukaryotic host cells, under the control of appropriate transcriptional initiation/termination regulatory sequences, which are chosen to be constitutively active or inducible in said cell. A cell line substantially enriched in such cells can be then isolated to provide a stable cell line.

Host cells are transfected or transformed with expression or cloning vectors described herein for protein production and cultured in conventional nutrient media modified as appropriate for inducing promoters, selecting transformants, or amplifying the genes encoding the desired sequences. The culture conditions, such as media, temperature, pH and the like, can be selected by the skilled artisan without undue experimentation. In general, principles, protocols, and practical techniques for maximizing the productivity of cell cultures can be found in Mammalian Cell Biotechnology: a Practical Approach, M. Butler, ed. (IRL Press, 1991) and Sambrook et al., supra.

For eukaryotic host cells (e.g. yeasts, insect or mammalian cells), different transcriptional and translational regulatory sequences may be employed, depending on the nature of the host. They may be derived form viral sources, such as adenovirus, papilloma virus, Simian virus or the like, where the regulatory signals are associated with a particular gene which has a high level of expression. Examples are the TK promoter of the Herpes virus, the SV40 early promoter, the yeast gal4 gene promoter, etc. Transcriptional initiation regulatory signals may be selected which allow for repression and activation, so that expression of the genes can be modulated. The cells which have been stably transformed by the introduced DNA can be selected by also introducing one or more markers which allow for selection of host cells which contain the expression vector. The marker may also provide for prototrophy to an auxotrophic host, biocide resistance, e.g. antibiotics, or heavy metals such as copper, or the like. The selectable marker gene can be either directly linked to the DNA sequences to be expressed (e.g., on the same vector), or introduced into the same cell by co-transfection. Additional elements may also be needed for optimal synthesis of proteins of the invention.

Suitable prokaryotic cells include bacteria (such as *Bacillus subtilis* or *E. coli*) transformed with a recombinant bacteriophage, plasmid or cosmid DNA expression vector. Such cells typically produce proteins comprising a N-terminal Methionine residue. Preferred cells to be used in the present invention are eukaryotic host cells, e.g. mammalian cells, such as human, monkey, mouse, and Chinese Hamster Ovary (CHO) cells, because they provide post-translational modifications to protein molecules, including correct folding or glycosylation at correct sites. Examples of suitable mammalian host cells include African green monkey kidney cells (Vero; ATCC CRL 1587), human embryonic kidney cells (293-HEK; ATCC CRL 1573), baby hamster kidney cells (BHK-21, BHK-570; ATCC CRL 8544, ATCC CRL 10314), canine kidney cells (MDCK; ATCC CCL 34), Chinese hamster ovary cells (CHO-K1; ATCC CCL61; CHO DG44 (Chasin et al., Som. Cell. Molec. Genet. 12:555, 1986)), rat pituitary cells (GH1; ATCC CCL82), HeLa S3 cells (ATCC CCL2.2), rat hepatoma cells (H-4-II-E; ATCC CRL 1548), SV40-transformed monkey kidney cells (COS-1; ATCC CRL 1650), Bowes melanoma and human hepatocellular carcinoma (for example Hep G2), murine embryonic cells (NIH-3T3; ATCC CRL 1658) and a number of other cell lines. Alternative eukaryotic host cells are yeast cells (e.g., *Saccharomyces*, *Kluyveromyces*, etc.) transformed with yeast expression vectors. Also yeast cells can carry out post-translational peptide modifications including glycosylation. A number of recombinant DNA strategies exist which utilize strong promoter sequences and high copy number of plasmids that can be utilized for production of the desired proteins in yeast. Yeast cells recognize leader sequences in cloned mammalian gene products and secrete polypeptides bearing leader sequences (i.e., pre-peptides).

For long-term, high-yield production of a recombinant polypeptide, stable expression is preferred. For example, cell lines which stably express the polypeptide of interest may be transformed using expression vectors which may contain viral origins of replication and/or endogenous expression elements and a selectable marker gene on the same or on a separate vector. Following the introduction of the vector, cells may be allowed to grow for 1-2 days in an enriched media before they are switched to selective media. The purpose of the selectable marker is to confer resistance to selection, and its presence allows growth and recovery of cells that successfully express the introduced sequences. Resistant clones of stably transformed cells may be proliferated using tissue culture techniques appropriate to the cell type. A cell line substantially enriched in such cells can be then isolated to provide a stable cell line.

A particularly preferred method of high-yield production of a recombinant polypeptide of the present invention is through the use of dihydrofolate reductase (DHFR) amplification in DHFR-deficient CHO cells, by the use of successively increasing levels of methotrexate as described in U.S. Pat. No. 4,889,803. The polypeptide obtained may be in a glycosylated form.

Antibodies disclosed herein can also be expressed in other eukaryotic cells, such as avian, fungal, insect, yeast, or plant cells. The baculovirus system provides an efficient means to introduce cloned genes into insect cells. The materials for baculovirus/insect cell expression systems are commercially available in kit form from, inter alia, Invitrogen.

In addition to recombinant DNA technologies, the antibodies of this invention may be prepared by chemical synthesis technologies. Examples of chemical synthesis technologies are solid phase synthesis and liquid phase synthesis. As a solid phase synthesis, for example, the amino acid corresponding to the carboxy-terminus of the polypeptide to be synthesised is bound to a support which is insoluble in organic solvents and, by alternate repetition of reactions (e.g., by sequential condensation of amino acids with their amino groups and side chain functional groups protected with appropriate protective groups), the polypeptide chain is extended. Solid phase synthesis methods are largely classified by the tBoc method and the Fmoc method, depending on the type of protective group used. Totally synthetic proteins are disclosed in the literature (Brown A et al., 1996).

The antibodies of the present invention can be produced, formulated, administered, or generically used in other alternative forms that can be preferred according to the desired method of use and/or production. The proteins of the invention can be post-translationally modified, for example by glycosylation. The polypeptides or proteins of the invention can be provided in isolated (or purified) biologically active form, or as precursors, derivatives and/or salts thereof.

Useful conjugates or complexes can also be generated for improving the agents in terms of drug delivery efficacy. For this purpose, the antibodies described herein can be in the form of active conjugates or complex with molecules such as polyethylene glycol and other natural or synthetic polymers (Harris J M and Chess R B, 2003; Greenwald R B et al., 2003; Pillai O and Panchagnula R, 2001). In this regard, the present invention contemplates chemically modified antibodies as disclosed herein, in which the antibody is linked with a polymer. Typically, the polymer is water soluble so that the conjugate does not precipitate in an aqueous environment, such as a physiological environment. An example of a suitable polymer is one that has been modified to have a single reactive group, such as an active ester for acylation, or an aldehyde for alkylation. In this way, the degree of polymerization can be controlled. An example of a reactive aldehyde is polyethylene glycol propionaldehyde, ormono-(C1-C10) alkoxy, or aryloxy derivatives thereof (see, for example, Harris, et al., U.S. Pat. No. 5,252,714). The polymer may be branched or unbranched. Moreover, a mixture of polymers can be used to produce the conjugates. The conjugates used for therapy can comprise pharmaceutically acceptable water-soluble polymer moieties. Suitable water-soluble polymers include polyethylene glycol (PEG), monomethoxy-PEG, mono-(C1-C10) alkoxy-PEG, aryloxy-PEG, poly-(N-vinyl pyrrolidone) PEG, tresyl monomethoxy PEG, PEG propionaldehyde, bis-succinimidyl carbonate PEG, propylene glycol homopolymers, a polypopyleneoxide/ethylene oxide co-polymer, polyoxyethylated polyols (e.g., glycerol), polyvinyl alcohol, dextran, cellulose, or other carbohydrate-based polymers. Suitable PEG may have a molecular weight from about 600 to about 60,000, including, for example, 5,000, 12,000, 20,000 and 25,000. A conjugate can also comprise a mixture of such water-soluble polymers.

Examples of conjugates comprise any of the antibody disclosed here above and a polyallcyl oxide moiety attached to the N-terminus of said soluble receptor. PEG is one suitable polyalkyl oxide. As an illustration, any of the antibody disclosed herein can be modified with PEG, a process known as "PEGylation." PEGylation can be carried out by any of the PEGylation reactions known in the art (see, for example, EP 0 154 316, Delgado et al., Critical Reviews in Therapeutic Drug Carrier Systems 9: 249 (1992), Duncan and Spreafico, Clin. Pharmacokinet. 27: 290 (1994), and Francis et al., Int J Hematol 68: 1 (1998)). For example, PEGylation can be performed by an acylation reaction or by an alkylation reaction with a reactive polyethylene glycol molecule. In an alternative approach, conjugates are formed by condensing activated PEG, in which a terminal hydroxy or amino group of PEG has been replaced by an activated linker (see, for example, Karasiewicz et al., U.S. Pat. No. 5,382,657). Preferably, all these modifications do not affect significantly the ability of the antibody to bind human IL-31.

The antibodies described herein may comprise an additional N-terminal amino acid residue, preferably a methionine. Indeed, depending on the expression system and conditions, polypeptides may be expressed in a recombinant host cell with a starting Methionine. This additional amino acid may then be either maintained in the resulting recombinant protein, or eliminated by means of an exopeptidase, such as Methionine Aminopeptidase, according to methods disclosed in the literature (Van Valkenburgh H A and Kahn R A, Methods Enzymol. (2002) 344:186-93; Ben-Bassat A, Bioprocess Technol. (1991) 12:147-59).

As it will be shown in the example part of the present document, mouse anti-human anti-IL-31 antibodies may include potential glycosylation sites in their variable domains. For example, clone 292.12.3.1 bears a glycosylation site in the framework region FR1 of the heavy chain variable domain. The inventors of the present invention have now found that said glycosylation site is not necessary to keep a good binding affinity for human IL-31. Moreover, abolishing this glycosylation site (e.g. by mutation) has a positive effect on the thermostability of the antibody. Therefore in an embodiment of the present invention, the antibodies as disclosed herein do not have glycosylation site in their variable domains.

IL-31 antigen binding molecules or IL-31 antagonists generated by the methods described herein can be tested for neutralization by a variety of methods. For example the luciferase assay as described in published U.S. patent application (See publication number 20030224487, Sprecher, Cindy et al., 2003) can be used. In addition neutralization can be tested by measuring a decrease in the production of pro-inflammatory chemokines such as TARC and MDC from keratinocyte cultures in the presence of ligand and the monoclonal antibody. Neutralization can also be measured by the in vivo and in vitro assays described herein.

Reduction of TARC and MDC in response to the humanized anti-IL-31 antibodies and antagonists described herein can be measured in an AD mouse model as follows:

Method I) Six-week old male NC/Nga mice (CRL Japan) are sensitized intradermally with 50 µg dust mite extract (D. pteronyssinus, Indoor Biotechnologies) three times a week on the back and scored for AD-like lesions. After 5 weeks of sensitization the mice are euthanized and the right ears were excised and placed into a single well of a 48-well culture dish (Corning) supplemented with RPMI+2% FBS (GIBCO Invitrogen). Plates are placed in 5% CO2 humidity controlled incubators. Supernatants are collected after 24 hours and frozen at −20° C. until further analysis.

Method II) Twelve-week old female NC/Nga mice (CRL Japan) are sensitized intradermally with 10 µg SEB (Toxin Technology) in the ear and on the back three times per week. The mice are scored for AD-like lesions. After 5 weeks of sensitization the mice are euthanized and 6 mm biopsy punches were taken from the injected ear of each mouse and placed into a single well of a 48-well culture dish supplemented with RPMI+2% FBS. Plates were placed in 5% CO2 humidity controlled incubators. Supernatants are collected after 24 hours and frozen at −20° C. until further analysis.

Groups of mice in both studies are treated with humanized IL-31 antigen binding molecules or the humanized IL-31 antibodies or antagonists intraperitoneally two times each week starting after 1 to 2 weeks of sensitization. TARC and MDC concentrations in the 24-hour supernatant samples are measured by conventional ELISA (R&D Systems).

In one embodiment, the humanized IL-31 antigen binding molecules or IL-31 antagonists of the present invention include, but are not limited to, Fab, Fab' and F(ab')$_2$, Fd, single-chain Fvs (scFv), single-chain antibodies, disulfide-linked Fvs (sdFv) and fragments comprising either a VL or VH domain. Antigen-binding antibody fragments, including single-chain antibodies, may comprise the variable region(s) (i.e., SEQ ID NOs: 25-45) alone or in combination with the entirety or a portion of the following: hinge region, $C_{H1}$, $C_{H2}$, and $C_{H3}$ domains. Also included in the invention are antigen-binding fragments also comprising any combination of variable region(s) with a hinge SEQ ID NOs: 25; 27; 29; 30; 31; 35; 36; 38; 39; 40; 41; 42; 43; 44, and 45 can be combined with the light chain variable region of any of SEQ ID NOs: 26; 28; 32; 33; 34; and 37.

In another embodiment, the invention provides an isolated antibody or antibody fragment that binds to human IL-31, comprising a humanized heavy chain variable domain and a humanized light chain variable domain wherein the humanized heavy chain variable domain and a humanized light chain variable domain are selected from the group consisting of: a) a humanized heavy chain variable domain comprising the amino acid sequence of SEQ ID NO: 25 and a humanized light chain variable domain comprising the amino acid sequence of SEQ ID NO: 26; b) a humanized heavy chain variable domain comprising the amino acid sequence of SEQ ID NO: 27 and a humanized light chain variable domain comprising the amino acid sequence of SEQ ID NO:26; c) a humanized heavy chain variable domain comprising the amino acid sequence of SEQ ID NO: 25 and a humanized light chain variable domain comprising the amino acid sequence of SEQ ID NO: 28; d) a humanized heavy chain variable domain comprising the amino acid sequence of SEQ ID NO: 29 and a humanized light chain variable domain comprising the amino acid sequence of SEQ ID NO: 26; e) a humanized heavy chain variable domain comprising the amino acid sequence of SEQ ID NO: 27 and a humanized light chain variable domain comprising the amino acid sequence of SEQ ID NO: 28; f) a humanized heavy chain variable domain comprising the amino acid sequence of SEQ ID NO: 30 and a humanized light chain variable domain comprising the amino acid sequence of SEQ ID NO: 26; g) a humanized heavy chain variable domain comprising the amino acid sequence of SEQ ID NO: 31 and a humanized light chain variable domain comprising the amino acid sequence of SEQ ID NO: 26; h) a humanized heavy chain variable domain comprising the amino acid sequence of SEQ ID NO: 25 and a humanized light chain variable domain comprising the amino acid sequence of SEQ ID NO: 32; i) a humanized heavy chain variable domain comprising the amino acid sequence of SEQ ID NO: 25 and a humanized light chain variable domain comprising the amino acid sequence of SEQ ID NO: 33; j) a humanized heavy chain variable domain comprising the amino acid sequence of SEQ ID NO: 25 and a humanized light chain variable domain comprising the amino acid sequence of SEQ ID NO: 34; k) a humanized heavy chain variable domain comprising the amino acid sequence of SEQ ID NO: 35 and a humanized light chain variable domain comprising the amino acid sequence of SEQ ID NO: 26; l) a humanized heavy chain variable domain comprising the amino acid sequence of SEQ ID NO: 27 and a humanized light chain variable domain comprising the amino acid sequence of SEQ ID NO: 32; m) a humanized heavy chain variable domain comprising the amino acid sequence of SEQ ID NO: 27 and a humanized light chain variable domain comprising the amino acid sequence of SEQ ID NO: 33; n) a humanized heavy chain variable domain comprising the amino acid sequence of SEQ ID NO: 27 and a humanized light chain variable domain comprising the amino acid sequence of SEQ ID NO: 34; o) a humanized heavy chain variable domain comprising the amino acid sequence of SEQ ID NO: 36 and a humanized light chain variable domain comprising the amino acid sequence of SEQ ID NO: 37; p) a humanized heavy chain variable domain comprising the amino acid sequence of SEQ ID NO: 25 and a humanized light chain variable domain comprising the amino acid sequence of SEQ ID NO: 37; q) a humanized heavy chain variable domain comprising the amino acid sequence of SEQ ID NO: 38 and a humanized light chain variable domain comprising the amino acid sequence of SEQ ID NO: 37; r) a humanized heavy chain variable domain comprising the amino acid sequence of SEQ ID NO: 39 and a humanized light chain variable domain comprising the amino acid sequence of SEQ ID NO: 37; s) a humanized heavy chain variable domain comprising the amino acid sequence of SEQ ID NO: 40 and a humanized light chain variable domain comprising the amino acid sequence of SEQ ID NO: 37; t) a humanized heavy chain variable domain comprising the amino acid sequence of SEQ ID NO: 41 and a humanized light chain variable domain comprising the amino acid sequence of SEQ ID NO: 37; u) a humanized heavy chain variable domain comprising the amino acid sequence of SEQ ID NO: 42 and a humanized light chain variable domain comprising the amino acid sequence of SEQ ID NO: 37; v) a humanized heavy chain variable domain comprising the amino acid sequence of SEQ ID NO: 43 and a humanized light chain variable domain comprising the amino acid sequence of SEQ ID NO: 37; w) a humanized heavy chain variable domain comprising the amino acid sequence of SEQ ID NO: 44 and a humanized light chain variable domain comprising the amino acid sequence of SEQ ID NO: 26; x) a humanized heavy chain variable domain comprising the amino acid sequence of SEQ ID NO: 36 and a humanized light chain variable domain comprising the amino acid sequence of SEQ ID NO: 28; y) a humanized heavy chain variable domain comprising the amino acid sequence of SEQ ID NO: 36 and a humanized light chain variable domain comprising the amino acid sequence of SEQ ID NO: 28; and z) a humanized heavy chain variable domain comprising the amino acid sequence of SEQ ID NO: 45 and a humanized light chain variable domain comprising the amino acid sequence of SEQ ID NO: 37.

In another embodiment, the invention provides an isolated antibody or antibody fragment that binds to human IL-31, comprising a humanized heavy chain variable domain and a humanized light chain variable domain wherein the humanized heavy chain variable domain and a humanized light chain variable domain are selected from the group consisting of: a) a humanized heavy chain variable domain having at least 90% sequence identity to the amino acid sequence of SEQ ID NO: 25 and a humanized light chain variable domain having at least 90% sequence identity to the amino acid sequence of SEQ ID NO: 26; b) a humanized heavy chain variable domain having at least 90% sequence identity to the amino acid sequence of SEQ ID NO: 27 and a humanized light chain variable domain having at least 90% sequence identity to the amino acid sequence of SEQ ID NO: 26; c) a humanized heavy chain variable domain having at least 90% sequence identity to the amino acid sequence of SEQ ID NO: 25 and a humanized light chain variable domain having at least 90% sequence identity to the amino acid sequence of SEQ ID NO: 28; d) a humanized heavy chain variable domain having at least 90% sequence identity to the amino acid sequence of SEQ ID NO: 29 and a humanized light chain variable domain having at least 90% sequence identity to the amino acid sequence of SEQ ID NO: 26; e) a humanized heavy chain variable domain having at least 90% sequence identity to the amino acid sequence of SEQ ID NO: 27 and a humanized light chain variable domain having at least 90% sequence identity to the amino acid sequence of SEQ ID NO: 28; f) a humanized heavy chain variable domain having at least 90% sequence identity to the amino acid sequence of SEQ ID NO: 30 and a humanized light chain variable domain having at least 90% sequence identity to the amino acid sequence of SEQ ID NO: 26; g) a humanized heavy chain variable domain having at least 90% sequence identity to the amino acid sequence of SEQ ID NO: 31 and a humanized light chain variable domain having at least 90% sequence identity to the amino acid sequence of SEQ ID NO: 26; h) a humanized heavy chain variable domain having at least 90% sequence identity to the amino acid sequence of SEQ ID NO: 25 and a humanized light chain variable domain having at least 90% sequence identity to the amino acid sequence of SEQ ID NO: 32; i) a humanized heavy chain variable domain having at least 90% sequence identity to the amino acid sequence of SEQ ID NO: 25 and a humanized light chain variable domain having at least 90% sequence identity to the amino acid sequence of SEQ ID NO: 33; j) a humanized heavy chain variable domain having at least 90% sequence identity to the amino acid sequence of SEQ ID NO: 25 and a humanized light chain variable domain having at least 90% sequence identity to the amino acid sequence of SEQ ID NO: 34; k) a humanized heavy chain variable domain having at least 90% sequence identity to the amino acid sequence of SEQ ID NO: 35 and a humanized light chain variable domain having at least 90% sequence identity to the amino acid sequence of SEQ ID NO: 26; l) a humanized heavy chain variable domain having at least 90% sequence identity to the amino acid sequence of SEQ ID NO: 27 and a humanized light chain variable domain having at least 90% sequence identity to the amino acid sequence of SEQ ID NO: 32; m) a humanized heavy chain variable domain having at least 90% sequence identity to the amino acid sequence of SEQ ID NO: 27 and a humanized light chain variable domain having at least 90% sequence identity to the amino acid sequence of SEQ ID NO: 33; n) a humanized heavy chain variable domain having at least 90% sequence identity to the amino acid sequence of SEQ ID NO: 27 and a humanized light chain variable domain having at least 90% sequence identity to the amino acid sequence of SEQ ID NO: 34; o) a humanized heavy chain variable domain having at least 90% sequence identity to the amino acid sequence of SEQ ID NO: 36 and a humanized light chain variable domain having at least 90% sequence identity to the amino acid sequence of SEQ ID NO: 37; p) a humanized heavy chain variable domain having at least 90% sequence identity to the amino acid sequence of SEQ ID NO: 25 and a humanized light chain variable domain comprising the amino acid sequence of SEQ ID NO: 37; q) a humanized heavy chain variable domain comprising the amino acid sequence of SEQ ID NO: 38 and a humanized light chain variable domain comprising the amino acid sequence of SEQ ID NO: 37; r) a humanized heavy chain variable domain comprising the amino acid sequence of SEQ ID NO: 39 and a humanized light chain variable domain comprising the amino acid sequence of SEQ ID NO: 37; s) a humanized heavy chain variable domain having at least 90% sequence identity to the amino acid sequence of SEQ ID NO: 40 and a humanized light chain variable domain having at least 90% sequence identity to the amino acid sequence of SEQ ID NO: 37; t) a humanized heavy chain variable domain having at least 90% sequence identity to the amino acid sequence of SEQ ID NO: 41 and a humanized light chain variable domain having at least 90% sequence identity to the amino acid sequence of SEQ ID NO: 37; u) a humanized heavy chain variable domain having at least 90% sequence identity to the amino acid sequence of SEQ ID NO: 42 and a humanized light chain variable domain having at least 90% sequence identity to the amino acid sequence of SEQ ID NO: 37; v) a humanized heavy chain variable domain having at least 90% sequence identity to the amino acid sequence of SEQ ID NO: 43 and a humanized light chain variable domain having at least 90% sequence identity to the amino acid sequence of SEQ ID NO: 37; w) a humanized heavy chain variable domain having at least 90% sequence identity to the amino acid sequence of SEQ ID NO: 44 and a humanized light chain variable domain having at least 90% sequence identity to the amino acid sequence of SEQ ID NO: 26; x) a humanized heavy chain variable domain having at least 90% sequence identity to the amino acid sequence of SEQ ID NO: 36 and a humanized light chain variable domain having at least 90% sequence identity to the amino acid sequence of SEQ ID NO: 28; y) a humanized heavy chain variable domain having at least 90% sequence identity to the amino acid sequence of SEQ ID NO: 36 and a humanized light chain variable domain having at least 90% sequence identity to the amino acid sequence of SEQ ID NO: 28; and z) a humanized heavy chain variable domain having at least 90% sequence identity to the amino acid sequence of SEQ ID NO: 45 and a humanized light chain variable domain having at least 90% sequence identity to the amino acid sequence of SEQ ID NO: 37.

In an aspect the invention provides an isolated antibody selected from the group consisting of: a) an antibody comprising a light chain consisting of amino acids sequence SEQ ID NO: 46 and a heavy chain consisting of amino acid sequence SEQ ID NO: 47; b) an antibody comprising a light chain consisting of amino acids sequence SEQ ID NO: 48 and a heavy chain consisting of amino acid sequence SEQ ID NO: 49; and c) an antibody comprising a light chain consisting of amino acids sequence SEQ ID NO: 50 and a heavy chain consisting of amino acid sequence SEQ ID NO: 51.

The present invention also includes recombinant humanized IL-31 antigen binding molecules or IL-31 antagonists that are functionally equivalent to those described above. Modified humanized IL-31 antigen binding molecules or IL-31 antagonists providing improved stability and/or therapeutic efficacy are also included. Examples of modified antibodies include those with conservative substitutions of amino acid residues, and one or more deletions or additions of amino acids which do not significantly deleteriously alter the antigen binding utility. Substitutions can range from changing or modifying one or more amino acid residues to complete redesign of a region as long as the therapeutic utility is maintained. Humanized IL-31 antigen binding molecules or IL-31 antagonists of the present invention can be can be modified post-translationally (e.g., acetylation, and phosphorylation) or can be modified synthetically (e.g., the attachment of a labeling group). It is understood that the humanized IL-31 antigen binding molecules or IL-31 antagonists designed by the present method may have additional conservative amino acid substitutions which have substantially no effect on antigen binding or other immunoglobulin functions.

The humanized IL-31 antigen binding molecules or IL-31 antagonists of the present invention include derivatives that are modified, for example, but not by way of limitation, the derivatives include humanized IL-31 antigen binding molecules or IL-31 antagonists that have been modified, e.g., by glycosylation, acetylation, pegylation, phosphylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the derivative may contain one or more non-classical amino acids.

Humanized IL-31 antigen binding molecules or IL-31 antagonists comprise CDRs of a mouse donor immunoglobulin and heavy chain and light chain frameworks of a human acceptor immunoglobulin. Methods of making humanized antibody are disclosed in U.S. Pat. Nos. 5,301,101; 5,585,089; 5,693,762; and 6,180,370 (each of which is incorporated by reference in its entirety). The CDRs of these antibodies can then be grafted to any selected human frameworks, which are known in the art, to generate the desired humanized antibody.

The invention also provides humanized IL-31 antigen binding molecules or IL-31 antagonists that competitively inhibit the binding of a monoclonal antibody described herein to human IL-31. Competitive inhibition can be determined by any method known in the art, for example, using the competitive binding assays described herein. In preferred embodiments, the antibody competitively inhibits the binding of a monoclonal antibody of the invention by at least 90%, at least 80%, at least 70%, at least 60%, or at least 50% to the polypeptide.

The invention also provides humanized IL-31 antigen binding molecules or IL-31 antagonists that competitively inhibit binding of an antibody to an epitope of the invention as determined by any method known in the art for determining competitive binding, for example, the immunoassays described herein. In preferred embodiments, the antibody competitively inhibits binding to the epitope by at least 90%, at least 80%, at least 70%, at least 60%, or at least 50%.

The in vivo half-lives of the humanized IL-31 antigen binding molecules or IL-31 antagonists can be increased by modifying (e.g., substituting, deleting or adding) amino acid residues identified as involved in the interaction between the Fc domain and the FcRn receptor (see, e.g., International Publication Nos. WO 97/34631 and WO 02/060919, which are incorporated herein by reference in their entireties), or by attaching polymer molecules such as high molecular weight polyethyleneglycol (PEG). PEG can be attached with or without a multifunctional linker either through site-specific conjugation of the PEG to the N- or C-terminus of said antibodies or antibody fragments or via epsilon-amino groups present on lysine residues. Linear or branched polymer derivatization that results in minimal loss of biological activity will be used. The degree of conjugation will be closely monitored by SDS-PAGE and mass spectrometry to ensure proper conjugation of PEG molecules to the antibodies. Unreacted PEG can be separated from antibody-PEG conjugates by, e.g., size exclusion or ion-exchange chromatography.

The present invention includes criteria by which a limited number of amino acids in the framework of a humanized immunoglobulin chain are chosen to be the same as the amino acids at those positions in the donor rather than in the acceptor, in order to increase the affinity of an antibody comprising the humanized immunoglobulin chain.

In addition to the humanized immunoglobulins specifically described herein, other "substantially homologous" modified immunoglobulins to the native sequences can be readily designed and manufactured utilizing various recombinant DNA techniques well known to those skilled in the art. A variety of different human framework regions may be used singly or in combination as a basis for the humanized immunoglobulins of the present invention. In general, modifications of the genes may be readily accomplished by a variety of well-known techniques, such as site-directed mutagenesis (see, Gillman and Smith, Gene, 8, 81-97 (1979) and S. Roberts et al., Nature, 328, 731-734 (1987), both of which are incorporated herein by reference).

The humanized antibodies of the invention include fragments as well as intact antibodies. Typically, these fragments compete with the intact antibody from which they were derived for antigen binding. The fragments typically bind with an affinity of at least $10^7$ M.$^{-1}$, and more typically $10^8$ or $10^9$ M.$^{-1}$ (i.e., within the same ranges as the intact antibody). Humanized antibody fragments include separate heavy chains, light chains Fab, Fab' F(ab')$_2$, and Fv. Fragments are produced by recombinant DNA techniques, or by enzymic or chemical separation of intact immunoglobulins.

For details in humanizing antibodies, see European Patent Nos. EP 239,400, EP 592,106, and EP 519,596; International Publication Nos. WO 91/09967 and WO 93/17105; U.S. Pat. Nos. 5,225,539, 5,530,101, 5,565,332, 5,585,089, 5,766,886, and 6,407,213; and Padlan, 1991, Molecular Immunology 28(4/5): 489 498; Studnicka et al., 1994, Protein Engineering 7(6): 805 814; Roguska et al., 1994, PNAS 91: 969 973; Tan et al., 2002, J. Immunol. 169: 1119 25; Caldas et al., 2000, Protein Eng. 13: 353 60; Morea et al., 2000, Methods 20: 267 79; Baca et al., 1997, J. Biol. Chem. 272: 10678 84; Roguska et al., 1996, Protein Eng. 9: 895 904; Couto et al., 1995, Cancer Res. 55 (23 Supp): 5973s 5977s; Couto et al., 1995, Cancer Res. 55: 1717 22; Sandhu, 1994, Gene 150: 409 10; Pedersen et al., 1994, J. Mol. Biol. 235: 959 73; Jones et al., 1986, Nature 321: 522-525; Reichmann et al., 1988, Nature 332: 323-329; and Presta, 1992, Curr. Op. Struct. Biol. 2: 593-596.

Various techniques have been developed for the production of antibody fragments. These fragments can be derived via proteolytic digestion of intact antibodies (see, e.g., Morimoto et al., Journal of Biochemical and Biophysical Methods 24: 107-117 (1992) and Brennan et al., Science, 229:81 (1985)), or produced directly by recombinant host cells. For example, the antibody fragments can be isolated from the antibody phage libraries discussed above. Alternatively, Fab'-SH fragments can be directly recovered from *E. coli* and chemically coupled to form F(ab')$_2$ fragments (Carter et al., Bio/Technology 10: 163-167 (1992)). According to another approach, F(ab')$_2$ fragments can be isolated directly from recombinant host cell culture. Other techniques for the production of antibody fragments will be apparent to the skilled practitioner. Further, examples of techniques which can be used to produce single-chain Fvs and antibodies include those described in U.S. Pat. Nos. 4,946,778 and 5,258,498; Huston et al., Methods in Enzymology 203:46-88 (1991); Shu et al., PNAS 90:7995-7999 (1993); and Skerra et al., Science 240:1038-1040 (1988).

The present invention encompasses antibodies recombinantly fused or chemically conjugated (including both covalently and non-covalently conjugations) to a polypeptide (or portion thereof, preferably at least 10, 20 or 50 amino acids of the polypeptide) of the present invention to generate fusion proteins. Thus, the invention also pertains to immunoconjugates comprising the antibody described herein conjugated to a cytotoxic agent such as a chemotherapeutic agent, toxin (e.g. an enzymatically active toxin of bacterial, fungal, plant or animal origin, or fragments thereof), or a radioactive isotope (i.e., a radioconjugate).

The present invention further includes compositions comprising the polypeptides of the present invention (e.g., those comprising an immunogenic or antigenic epitope) fused or conjugated to heterologous polypeptide sequences (e.g., antibody domains other than the variable regions). For example, the polypeptides of the present invention may be fused or conjugated to an antibody Fc region, or portion thereof. For example, polypeptides of the present invention (including fragments or variants thereof), may be fused with the constant domain of immunoglobulins (IgA, IgE, IgG, IgM), or portions thereof ($C_{H1}$, $C_{H2}$, $C_{H3}$, or any combination thereof and portions thereof, resulting in chimeric polypeptides. The antibody portion fused to a polypeptide of the present invention may comprise the constant region, hinge region, $C_{H1}$ domain, $C_{H2}$ domain, and $C_{H3}$ domain or any combination of whole domains or portions thereof. The polypeptides may also be fused or conjugated to the above antibody portions to form multimers. For example, Fc portions fused to the polypeptides of the present invention can form dimers through disulfide bonding between the Fc portions. Higher multimeric forms can be made by fusing the polypeptides to portions of IgA and IgM. Methods for fusing or conjugating the polypeptides of the present invention to antibody portions are known in the art. See, e.g., U.S. Pat. Nos. 5,336,603; 5,622,929; 5,359,046; 5,349,053; 5,447,851; 5,112,946; EP 307,434; EP 367,166; PCT publications WO 96/04388; WO 91/06570; Ashkenazi et al., Proc. Natl. Acad. Sci. USA 88:10535-10539 (1991); Zheng et al., J. Immunol. 154:5590-5600 (1995); and Vil et al., Proc. Natl. Acad. Sci. USA 89:11337-11341 (1992) (said references incorporated by reference in their entireties). By way of another non-limiting example, polypeptides and/or antibodies of the present invention (including fragments or variants thereof) may be fused with albumin (including but not limited to recombinant human serum albumin or fragments or variants thereof (see, e.g., U.S. Pat. No. 5,876,969, issued Mar. 2, 1999, EP Patent 0 413 622, and U.S. Pat. No. 5,766,883, issued Jun. 16, 1998, herein incorporated by reference in their entirety)). Polypeptides and/or antibodies of the present invention (including fragments or variants thereof) may be fused to either the N- or C-terminal end of the heterologous protein (e.g., immunoglobulin Fc polypeptide or human serum albumin polypeptide). Polynucleotides encoding fusion proteins of the invention are also encompassed by the invention.

As discussed above, the polypeptides of the present invention may be fused or conjugated to the above antibody portions to increase the in vivo half life of the polypeptides or for use in immunoassays using methods known in the art. Further, the polypeptides of the present invention may be fused or conjugated to the above antibody portions to facilitate purification. One reported example describes chimeric proteins consisting of the first two domains of the human CD4-polypeptide and various domains of the constant regions of the heavy or light chains of mammalian immunoglobulins. (See, e.g., EP 394,827; Traunecker et al., Nature 331:84-86 (1988)). Enhanced delivery of an antigen across the epithelial barrier to the immune system has been demonstrated for antigens (e.g., insulin) conjugated to an FcRn binding partner such as IgG or Fc fragments (see, e.g., PCT Publications WO 96/22024 and WO 99/04813). The polypeptides of the present invention fused or conjugated to an antibody having disulfide-linked dimeric structures (due to the IgG) may also be more efficient in binding and neutralizing other molecules, than the monomeric secreted protein or protein fragment alone. (Fountoulakis et al., J. Biochem. 270:3958-3964 (1995)). In many cases, the Fc part in a fusion protein is beneficial in therapy and diagnosis, and thus can result in, for example, improved pharmacokinetic properties. (EP A 232, 262). Alternatively, deleting the Fc part after the fusion protein has been expressed, detected, and purified, would be desired. For example, the Fc portion may hinder therapy and diagnosis if the fusion protein is used as an antigen for immunizations. In drug discovery, for example, human proteins, such as hIL-5, have been fused with Fc portions for the purpose of high-throughput screening assays to identify antagonists of hIL-5. (See, D. Bennett et al., J. Molecular Recognition 8:52-58 (1995); K. Johanson et al., J. Biol. Chem. 270:9459-9471 (1995)0. Such techniques also include, but are not limited to, the use of bifunctional conjugating agents (see e.g., U.S. Pat. Nos. 5,756,065; 5,714,631; 5,696,239; 5,652,361; 5,505,931; 5,489,425; 5,435,990; 5,428,139; 5,342,604; 5,274,119; 4,994,560; and 5,808,003; the contents of each of which are hereby incorporated by reference in its entirety).

Moreover, the polypeptides of the invention (e.g., antibodies or fragments thereof) can be fused to marker sequences, such as a peptide to facilitates their purification. In a further embodiment, nucleic acids encoding the polypeptides of the invention (including, but not limited to nucleic acids encoding immunogenic and/or antigenic epitopes) can also be recombined with a gene of interest as an epitope tag (e.g., the hemagglutinin tag ("HA") or flag tag) to aid in detection and purification of the expressed polypeptide. In preferred embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., Proc. Natl. Acad. Sci. USA 86:821-824 (1989), for instance, hexa-histidine provides for convenient purification of the fusion protein. Other peptide tags useful for purification include, but are not limited to, the "HA" tag, which corresponds to an epitope derived from the influenza hemagglutinin protein (Wilson et al., Cell 37:767 (1984)) and the "flag" tag.

The present invention further encompasses humanized IL-31 antigen binding molecules or IL-31 antagonists conjugated to a diagnostic or therapeutic agent. The IL-31 antigen binding molecules or IL-31 antagonists can be used diagnostically to, for example, monitor the development or progression of a pruritic disease as part of a clinical testing procedure to, e.g., determine the efficacy of a given treatment, diagnosis, detection, and/or prevention regimen. Detection can be facilitated by coupling the antibody to a detectable substance. Examples of detectable substances include various enzymes, prosthetic groups, fluorescent materials, luminescent materials, bioluminescent materials, radioactive materials, positron emitting metals using various positron emission tomographies, and nonradioactive paramagnetic metal ions. See, for example, U.S. Pat. No. 4,741,900 for metal ions which can be conjugated to antibodies for use as diagnostics according to the present invention. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include $^{125}$I, $^{131}$I, $^{111}$In or $^{99}$Tc.

Further, humanized IL-31 antigen binding molecules or IL-31 antagonists may be conjugated to a therapeutic moiety such as a cytotoxin, e.g., a cytostatic or cytocidal agent, a therapeutic agent or a radioactive metal ion. A cytotoxin or cytotoxic agent includes any agent that is detrimental to cells. Examples include paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The conjugates of the invention can be used for modifying a given biological response, the therapeutic agent or drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, a-interferon, .beta.-interferon, nerve growth factor, platelet derived growth factor, tissue plasminogen activator, a thrombotic agent or an anti-angiogenic agent, e.g., angiostatin or endostatin; or, biological response modifiers such as, for example, lymphokines, interleukin-1 ("IL-1"), interleukin-2 ("IL-2"), interleukin-6 ("IL-6"), granulocyte macrophase colony stimulating factor ("GM-CSF"), granulocyte colony stimulating factor ("G-CSF"), or other growth factors.

Humanized IL-31 antigen binding molecules or IL-31 antagonists may also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

Techniques for conjugating such therapeutic moiety to antibodies are well known, see, e.g., Amon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., "The Preparation And Cytotoxic Properties Of Antibody-Toxin Conjugates", Immunol. Rev. 62:119-58 (1982).

Alternatively, humanized IL-31 antigen binding molecules or IL-31 antagonists can be conjugated to a second antibody to form an antibody heteroconjugate as described by Segal in U.S. Pat. No. 4,676,980.

An humanized IL-31 antigen binding molecules or IL-31 antagonists, with or without a therapeutic moiety conjugated to it, administered alone or in combination with cytotoxic factor(s) and/or cytokine(s) can be used as a therapeutic.

Humanized IL-31 antigen binding molecules or IL-31 antagonists may be used for tagging cells that express IL-31; for isolating IL-31 by affinity purification; for diagnostic assays for determining circulating levels of IL-31 polypeptides; for detecting or quantitating soluble IL-31 as a marker of underlying pathology or disease; in analytical methods employing FACS; for screening expression libraries; for generating anti-idiotypic antibodies; and as neutralizing antibodies or as antagonists to block IL-31 activity in vitro and in vivo. Suitable direct tags or labels include radionuclides, enzymes, substrates, cofactors, inhibitors, fluorescent markers, chemiluminescent markers, magnetic particles and the like; indirect tags or labels may feature use of biotin-avidin or other complement/anti-complement pairs as intermediates. Antibodies herein may also be directly or indirectly conjugated to drugs, toxins, radionuclides and the like, and these conjugates used for in vivo diagnostic or therapeutic applications. Moreover, antibodies to IL-31 or fragments thereof may be used in vitro to detect denatured IL-31 or fragments thereof in assays, for example, Western Blots or other assays known in the art.

Suitable detectable molecules may be directly or indirectly attached to the polypeptide or antibody, and include radionuclides, enzymes, substrates, cofactors, inhibitors, fluorescent markers, chemiluminescent markers, magnetic particles and the like. Suitable cytotoxic molecules may be directly or indirectly attached to the polypeptide or antibody, and include bacterial or plant toxins (for instance, diphtheria, toxin, saporin, *Pseudomonas* exotoxin, ricin, abrin and the like), as well as therapeutic radionuclides, such as iodine-131, rhenium-188 or yttrium-90 (either directly attached to the polypeptide or antibody, or indirectly attached through means of a chelating moiety, for instance). Polypeptides or antibodies may also be conjugated to cytotoxic drugs, such as adriamycin. For indirect attachment of a detectable or cytotoxic molecule, the detectable or cytotoxic molecule can be conjugated with a member of a complementary/anticomplementary pair, where the other member is bound to the polypeptide or antibody portion. For these purposes, biotin/streptavidin is an exemplary complementary/anticomplementary pair.

The IL-31 antigen binding molecules or IL-31 antagonists of the present invention can be measured for their ability to inhibit, block, or neutralize the IL-31 ligand as determined by various in vivo models known in the art and described herein, including but not limited to the NC/Nga model, the Ova epicutaneous model, the chronic hypersensitivity model, and the chronic hapten model.

Both skin-homing T cells and epidermal keratinocytes have been implicated in the pathology of skin diseases in humans. IL-31 mRNA and protein expression is restricted to the skin-homing CLA+ T cell population in humans. See U.S. patent application Ser. No. 11/353,427, filed Feb. 14, 2006, (U.S. Patent Publication No. 2006-0188499) and U.S. patent application Ser. No. 11/353,454, filed Feb. 14, 2006, (U.S. Patent Publication No. 2006-0188500), both of which are incorporated herein by reference. As such, an antagonist to IL-31, including an antibody or receptor antagonist will be useful in treating skin and epidermal diseases which have expression of CLA+ T cells. Such diseases include, for example, atopic dermatitis, contact dermatitis, drug-induced allergic reactions, skin-tropic viruses and viral associated pruritis, vitiligo, cutaneous T cell lymphoma, alopecia aerata, acne rosacea, acne vulgaris, prurigo nodularis, and bullous pemphigoid. Chemokine markers such as TARC and MDC are useful to measure the effect of a neutralizing monoclonal antibody to IL-31. The inhibitory effects of treatment with humanized IL-31 antigen binding molecules or IL-31 antagonists described herein can be measured by monitoring the levels of TARC and MDC.

Contact Dermatitis

Allergic contact dermatitis is defined as a T cell mediated immune reaction to an antigen that comes into contact with the skin. The CLA+ T cell population is considered to be involved in the initiation of dermatitis since allergen dependent T cell responses are largely confined to the CLA+ population of cells (See Santamaria-Babi, L. F., et al., *J Exp Med:* 181, 1935, (1995)). Recent data has found that only memory (CD45RO+) CD4+ CLA+ and not CD8+ T cells proliferate and produce both type-1 (IFN-) and type-2 (IL-5) cytokines in response to nickel, a common contact hypersensitivity allergen. Furthermore, cells expressing CLA in combination with CD4, CD45RO (memory) or CD69 are increased after nickel-specific stimulation and express the chemokine receptors CXCR3, CCR4, CCR10 but not CCR6. See Moed H., et al., *Br J Dermatol*:51, 32, (2004).

In animal models, it has been demonstrated that allergic contact dermatitis is T-cell dependent and that the allergic-responsive T cells migrate to the site of allergen application. See generally: Engeman T. M., et al., *J Immunol:* 164, 5207, (2000); Ferguson T. A. & Kupper T. S. *J Immunol:* 150, 1172, (1993); and Gorbachev A. V. & Fairchild R. L. *Crit Rev Immunol:* 21, 451 (2001). Since CLA+ T cells produce IL-31 and IL-31 stimulation of skin keratinocytes can induce pro-inflammatory chemokines, such as TARC and MDC, IL-31 may be involved in the pathophysiology of contact dermatitis. By using a neutralizing IL-31 antibody in a mouse model of contact hypersensitivity.

Thus, neutralization of IL-31 by the humanized IL-31 antigen binding molecules or IL-31 antagonists described herein may be used to improve clinical outcome of Contact Hypersensitivity by inhibition, reduction, neutralization, prevention or blocking the inflammation and/or scratching associated with disease.

Atopic Dermatitis

Atopic dermatitis (AD) is a chronically relapsing inflammatory skin disease with a dramatically increasing incidence over the last decades. Clinically AD is characterized by highly pruritic often excoriated plaques and papules that show a chronic relapsing course. The diagnosis of AD is mostly based on major and minor clinical findings. See Hanifin J. M., *Arch Dermatol:* 135, 1551 (1999). Histopathology reveals spongiosis, hyper and focal parakeratosis in acute lesions, whereas marked epidermal hyperplasia with hyper and parakeratosis, acanthosis/hypergranulosis and perivascular infiltration of the dermis with lymphocytes and abundant mast cells are the hallmarks of chromic lesions.

T cells play a central role in the initiation of local immune responses in tissues and evidence suggests that skin-infiltrating T cells in particular, may play a key role in the initiation and maintenance of disregulated immune responses in the skin. Approximately 90% of infiltrating T cells in cutaneous inflammatory sites express the cutaneous lymphocyte-associated Ag (CLA+) which binds E-selectin, an inducible adhesion molecule on endothelium (reviewed in Santamaria-Babi L. F., et al., *Eur J Dermatol:* 14, 13, (2004)). A significant increase in circulating CLA+ T cells among AD patients compared with control individuals has been documented (See Teraki Y., et al., *Br J Dermatol:* 143, 373 (2000), while others have demonstrated that memory CLA+ T cells from AD patients preferentially respond to allergen extract compared to the CLA− population (See Santamaria-Babi, L. F., et al., *J Exp Med:* 181, 1935, (1995)). In humans, the pathogenesis of atopic disorders of the skin have been associated with increases in CLA+ T cells that express increased levels of Th-2-type cytokines like IL-5 and IL-13 9, 10. See Akdis M., et al., *Eur J Immunol:* 30, 3533 (2000); and Hamid Q., et al., *J Allergy Clin Immunol:* 98, 225 (1996).

NC/Nga Mice spontaneously develop AD-like lesions that parallel human AD in many aspects, including clinical course and signs, histophathology and immunopathology when housed in non-specified pathogen-free (non-SPF) conditions at around 6-8 weeks of age. In contrast, NC/Nga mice kept under SPF conditions do not develop skin lesions. However, onset of spontaneous skin lesions and scratching behaviour can be synchronized in NC/Nga mice housed in a SPF facility by weekly intradermal injection of crude dust mite antigen. See Matsuoka H., et al., *Allergy:* 58, 139 (2003). Therefore, the development of AD in NC/Nga is a useful model for the evaluation of novel therapeutics for the treatment of AD.

In addition to the NC/Nga model of spontaneous AD, epicutaneous sensitization of mice using OVA can also be used as a model to induce antigen-dependent epidermal and dermal thickening with a mononuclear infiltrate in skin of sensitized mice. This usually coincides with elevated serum levels of total and specific IgE, however no skin barrier dysfunction or pruritus normally occurs in this model. See Spergel J. M., et al., *J Clin Invest,* 101: 1614, (1998). This protocol can be modified in order to induce skin barrier disregulation and pruritus by sensitizing DO11.10 OVA TCR transgenic mice with OVA. Increasing the number of antigen-specific T cells that could recognize the sensitizing antigen may increase the level of inflammation in the skin to induce visible scratching behaviour and lichenification/scaling of the skin.

Both the NC/Nga spontaneous AD model and the OVA epicutaneous DO11.10 model are used to evaluate the ability of the humanized IL-31 antigen binding molecules or IL-31 antagonists described herein to inhibit, reduce, or neutralize the effects of IL-31. Administration of humanized IL-31 antigen binding molecules or IL-31 antagonists can result in a reduction in scratching that can be effective in treating pruritic diseases including, but not limited to, atopic dermatitis, prurigo nodularis, and eczema, since cessation of scratching will stop progression of dermatitis, the development of which is dependent on scratching.

Additional models to measure the inhibitory effects of the humanized IL-31 antigen binding molecules or IL-31 antagonists described herein are described by Umeuchi, H. et al., European Journal of Pharmacology, 518: 133-139, 2005; and by Yoo, J. et al., J. Experimental Medicine, 202:541-549, 2005.

Thus, neutralization of IL-31 by the humanized IL-31 antigen binding molecules or IL-31 antagonists described herein may be used to improve clinical outcome of dermatitis and pruritic diseases including atopic dermatitis, prurigo nodularis, and eczema by inhibition, reduction, prevention or blocking the inflammation and/or scratching associated with disease.

Methods of measuring the ability of the humanized anti-IL-31 antibodies and antagonists to inhibit, reduce, or neutralize the itch response include the following assays and models:

I) Capsaicin Treatment of IL-31 Treated Mice

Ten week old BALB/c animals (CRL) are anaesthetized and injected with a long-lasting analgesic agent, bupranorphine hydrochloride, subcutaneously at 0.1 mg/kg before injection of 0.25 ml of 4 mg/ml solution of capsaicin in 10% ethanol+10% Tween-80 in saline subcutaneously into scruff of neck. Animals are kept anaesthetized for at least 30 min following neurotoxin treatment. Forty-eight hours later, 14-day osmotic pumps are implanted subcutaneously for continuous delivery of 20 ug/day of IL-31 for 14 days. Mice are monitored daily for 6 days for alopecia and pruritis using the following criteria: 0=no scratching, animal appears normal, 1=thinning of coat in small areas, scratching noted, 2=minor hair loss (small patches), scratching, 3=moderate hair loss, scratching, and 4=severe hair loss, excessive scratching.

Neutralization, inhibition, or reduction of IL-31 by humanized IL-31 antigen binding molecules or IL-31 antagonists may decrease the incidence and intensity of itch, and therefore dermatitis, in patients suffering from skin disorders that involve itch.

II) Tact Gene Expression

Mice that are homozygous null for the Tac1 gene express no detectable substance P or neurokinin A. These mice have significantly reduced nociceptive pain responses to moderate to intense stimuli and are therefore a useful tool for studying the contribution of tachykinin peptides to pain/itch processing and inflammatory disease states. Twelve week old, Tac1 knockout mice were implanted with 14-day osmotic pumps delivering 1 ug/day of IL-31 protein and observed daily for alopecia and pruritis using the following criteria: 0=no scratching, animal appears normal, 1=thinning of coat in small areas, scratching noted, 2=minor hair loss (small patches), scratching, 3=moderate hair loss, scratching, and 4=severe hair loss, excessive scratching.

Results of this study show that Tac1 deficient mice were less susceptible to IL-31 induced scratching/hairloss compared to wildtype control mice. While 100% (10/10) of wildtype mice had developed evidence of scratching and hairloss by day 6 of IL-31 treatment, only 33.3% (2/6) Tac1 deficient mice were showing signs of scratching and hairloss at the same time-point. Thus, neutralization, inhibition or reduction of IL-31 by humanized IL-31 antigen binding molecules or IL-31 antagonists may decrease the incidence and intensity of scratching in the context of dermatitis.

III) Administration of IL-31 Neutralizing Antibody

Normal female BALB/c mice (CRL) approximately 8 to 12 weeks old can be implanted subcutaneously with 14-day osmotic pumps (Alzet, #2002) delivering 1 ug/day mIL-31. Groups of mice receive intraperitoneal (i.p.) injections of rat anti-mouse IL-31 monoclonal antibody 10 mg/kg (200 ug/mouse) twice weekly starting 1 week prior to IL-31 delivery. Control groups of mice receive i.p. injections of vehicle (PBS/0.1% BSA) with the identical dosing schedules. Mice are scored daily for alopecia and pruritus using the following criteria: 0=no scratching, animal appears normal, 1=thinning of coat in small areas, scratching noted, 2=minor hair loss (small patches), scratching, 3=moderate hair loss, scratching, and 4=severe hair loss, excessive scratching.

Thus, neutralization, reduction or inhibition of IL-31 by IL-31 antigen binding molecules or IL-31 antagonists may delay the onset of the scratch/hairloss response induced by IL-31.

The effects of humanized IL-31 antigen binding molecules or IL-31 antagonists are measured by inhibition of scratching, itching, dermatitis, a reduction in IL-31RA expression in keratinocytes, and/or a reduction in score for alopecia and pruritis.

Drug-Induced Delayed Type Cutaneous Allergic Reactions

Drug-induced delayed type cutaneous allergic reactions are very heterogeneous and may mirror many distinct pathophysiological events. See Brockow K., et al., *Allergy:* 57, 45 (2002). Immunological mechanisms involved in these reactions have been shown as either antibody or cell mediated. In immediate drug allergy an IgE-mediated antibody reaction can be demonstrated by a positive skin prick and/or intradermal test after 20 min, whereas non-immediate reactions to drugs can occur more than one hour after last drug intake and are often T-cell mediated. Non-immediate T-cell mediated delayed type reactions can occur in patients with adverse drug reactions to penicillins for example. Proliferative T cell responses to penicillins have been shown to be restricted to the memory (CD45RO+) CLA+ subpopulation of T cells from penicillin allergic patients whereas the CD45RO+ CLA− subset shows no proliferative response. See Blanca M., Leyva L., et al., *Blood Cells Mol Dis:* 31, 75 (2003). Delayed-type hypersensitivity (DTH) reactions can be artificially reproduced in mice, allowing assessment of factors that may be involved in the initiation and perpetuation of the DTH response. Humanized IL-31 antigen binding molecules or IL-31 antagonists could be effective in limiting, reducing, inhibiting a delayed type hypersensitivity reaction.

Toxic epidermal necrolysis (TEN) is a very rare but extremely severe drug reaction characterized by widespread apoptosis of epidermis with extensive blisters. Studies have shown that lymphocytes infiltrating the blister are CLA+ T cells and can exhibit cytotoxicity towards epidermal keratinocytes. See Leyva L., et al., *J Allergy Clin Immunol:* 105, 157 (2000); and Nassif A., Bensussan A., et al., *J Allergy Clin Immunol:* 114, 1209 2004). A transgenic mouse system, whereby OVA is expressed under the control of the keratin-5 (K5) promoter in the epidermal and hair follicular keratinocytes of mice, has been generated to establish an animal model for TEN. OVA specific CD8+ T cells, when adoptively transferred into K5-OVA mice, undergo activation and proliferation in the skin-draining lymph nodes and target the skin of K5-OVA mice, resulting in development of skin lesions that are reminiscent of TEN. See Azukizawa H., et al., *Eur J Immunol:* 33, 1879 (2003).

Thus, neutralization of IL-31 by the humanized IL-31 antigen binding molecules or IL-31 antagonists described herein may be used to improve clinical outcome of TEN by inhibition, reduction, prevention or blocking the inflammation and/or scratching associated with disease.

Bullous Pemphigoid

Bullous pemphigoid is a subepidermal disorder which manifests as subepidermal blisters with a dermal infiltrate of neutrophils and eosinophils. Diagnosis is characterized by the presence of antigen-specific antibodies against specific adhesion proteins of the epidermis and dermal-epidermal junction. See Jordon R. E., et al., *JAMA:* 200, 751 (1967). Studies analyzing the role of T cells in the pathogenesis of bullous pemphigoid by analysis of PBL and skin blister T cells have found a predominance of CLA+ T cells expressing increased levels of Th2-cytokines like IL-4 and IL-13. See Teraki Y., et al., *J Invest Dermatol:* 117, 1097 (2001). In bullous pemphigoid patients following therapy with systemic corticosteroids, the frequency of CLA+, but not CLA–, interleukin-13-producing cells is significantly decreased. Decreases in CLA+ cells following corticosteroid treatment is associated with clinical improvement. See Teraki, *ibid.*

Thus, neutralization of IL-31 by the humanized IL-31 antigen binding molecules or IL-31 antagonists described herein may be used to improve clinical outcome of bullous pemphigoid by inhibition, reduction, prevention or blocking the inflammation and/or scratching associated with disease.

Alopecia Areata

Alopecia areata (AA) is regarded as a tissue-restricted autoimmune disease of hair follicles in which follicular activity is arrested because of the continued activity of lymphocytic infiltrates. AA results in patches of complete hair loss anywhere on the body, though actual loss of hair follicles does not occur, even in hairless lesions. Although clinical signs of inflammation are absent, skin biopsies from sites of active disease show perifollicular lymphocytic inflammation of primarily CD4+ cells, along with a CD8+ intrafollicular infiltrate. See Kalish R. S. & Gilhar A. *J Investig Dermatol Symp Proc:* 8, 164 (2003).

Studies have shown that scalp skin infiltrating CD4+ or CD8+ lymphocytes express CLA and, in peripheral blood of individuals with AA, the percent of CLA+ CD4+ or CD8+ lymphocytes is significantly higher than that of normal controls. Furthermore, patients with severe or progressive AA show a much higher CLA– positivity compared to patients recovering from the disease and a decrease in percent CLA+ cells parallels a good clinical course. See Yano S., et al., *Acta Derm Venereol:* 82, 82 (2002). These studies therefore suggest that CLA+ lymphocytes may play an important role in AA. Xenograft models have demonstrated that activated T cells are likely to play a role in the pathogenesis of AA. Lesional scalp from AA patients grafted onto nude mice regrows hair coincident with a loss of infiltrating lymphocytes from the graft and, transfer of activated lesional T cells to SCID mice can transfer hair loss to human scalp explants on SCID mice. See Kalish R. S. & Gilhar A. *J Investig Dermatol Symp Proc:* 8, 164 (2003).

A variety of immunomodulating therapies are part of the usual treatment for this disorder however none of these treatments have been consistent in their efficacy. See Tang L., et al., *J Invest Dermatol:* 120, 400 (2003); Tang L., et al., (2004); and Tang L., et al., *J Am Acad Dermatol:* 49, 1013 (2003). Nevertheless, their uses in valid animal models provide a tool to dissect out molecular mechanisms of therapeutic effects. See Shapiro J., et al., *J Investig Dermatol Symp Proc:* 4, 239 (1999); Tang L., et al., Old wine in new bottles: reviving old therapies for alopecia areata using rodent models (2003); and Verma D. D., et al., *Eur J Dermatol*:14, 332 (2004).

Thus, neutralization of IL-31 by the humanized IL-31 antigen binding molecules or IL-31 antagonists described herein may be used to improve clinical outcome of alopecia areata by inhibition, reduction, prevention or blocking the inflammation and/or scratching associated with disease.

Acne Rosacea/Acne Vulgaris

Acne vulgaris, a disorder of the pilosebaceous apparatus, is the most common skin problem of adolescence. Abnormalities in follicular keratinization are thought to produce the acne lesion. Acne rosacea is differentiated from acne vulagaris by the presence of red papules, pustules, cysts and extensive telangiectasias, but the absence of comedones (white heads). Increased sebum excretion from sebaceous glands is a major factor in the pathophysiology of acne vulgaris. Other sebaceous gland functions are also associated with the development of acne, including sebaceous proinflammatory lipids; different cytokines produced locally; periglandular peptides and neuropeptides, such as corticotrophin-releasing hormone, which is produced by sebocytes; and substance P, which is expressed in the nerve endings at the vicinity of healthy-looking glands of acne patients. See Zouboulis C. C. *Clin Dermatol:* 22, 360 (2004).

Although the pathophysiology of acne vulgaris and acne rosacea remains unknown, clinical observations and histopathologic studies suggest that inflammation of the pilosebaceous follicle may be central to the pathogenesis of rosacea and acne vulgaris. Early studies on analysis of T cell subsets infiltrating rosacea legions indicated that the majority of T cells expressed CD4. See Rufli T. & Buchner S. A. *Dermatologica:* 169, 1 (1984).

CD4+ T cells produce IL-31 and IHC analysis of skin for IL-31 expression suggests that IL-31 is expressed in sebaceous and sweat glands. IL-31 stimulation of epidermal keratinocytes induces expression of chemokines which likely results in cellular infiltration suggesting that IL-31 may contribute to the pro-inflammatory response in skin. See Dillon S. R., et al., *Nat Immunol:* 5, 752 (2004). IL-31 may therefore contribute to the pathophysiology of acne rosacea and acne vulgaris.

Thus, neutralization of IL-31 by the humanized IL-31 antigen binding molecules or IL-31 antagonists described herein may be used to improve clinical outcome of acne vulgaris by inhibition, reduction, prevention or blocking the inflammation and/or scratching associated with disease.

Prurigo Nodularis

Prurigo nodularis is an eruption of lichenified or excoriated nodules caused by intractable pruritus that is difficult to treat. While chronic rubbing results in lichenification, and scratching in linear excoriations, individuals who pick and gouge at their itchy, irritated skin tend to produce markedly thickened papules known as prurigo nodules. Although prurigo nodularis is not specific to atopic dermatitis, many patients with these nodules also have an atopic reaction, which manifests as allergic rhinitis, asthma, or food allergy. T cells represent the majority of infiltrating cells in prurigo lesions and these lesions often represents the most pruritic skin lesion in atopy patients.

Topical treatment of prurigo nodularis with capsaicin, an anti-pruritic alkaloid that interferes with the perception of prurities and pain by depletion of neuropeptides like substance P in small sensory cutaneous nerves, has proven to be an effective and safe regimen resulting in clearing of the skin lesions. See Stander S., et al., *J Am Acad Dermatol:* 44, 471 (2001). Studies of the itch response in NC/Nga mice using capsaicin treatment showed that the spontaneous development of dermatitis lesions was almost completely prevented. Furthermore, the elevation of serum IgE levels was significantly suppressed and infiltrating eosinophils and mast cell numbers in lesional skin of capsaicin treated mice were reduced. See Mihara K., et al., *Br J Dermatol:* 151, 335 (2004). The observations from this group suggest that scratching behaviour might contribute to the development of dermatitis by enhancing various immunological responses, therefore implying that prevention of the itch sensation and/or itch-associated scratching behaviour might be an effective treatment for AD. See Mihara K., et al., *Br J Dermatol:* 151, 335 (2004). Thus, the humanized anti-IL-31 antibodies described herein will be useful in minimizing the effects of AD, prurigo nodularis, and other pruritic diseases as they are shown herein to reduce the amount of scratching in NC/Nga mice.

Chronic delivery of IL-31 induces pruritis and alopecia in mice followed by the development of skin lesions resembling dermatitis suggesting that IL-31 may induce itching. See Dillon S. R., et al., *Nat Immunol:* 5, 752 (2004). The involvement of IL-31 in induction of the itch response can be measured, for example, by two methods (i) capsaicin treatment of IL-31-treated mice; and (ii) IL-31 treatment of Tac1 knockout mice, which have significantly reduced nociceptive pain responses because of lack of expression of neuropeptides. In addition, whether neutralization of IL-31 in IL-31 treated mice with humanized IL-31 antigen binding molecules or IL-31 antagonists could prevent pruritis and alopecia can be tested in these models.

Thus, neutralization of IL-31 by the humanized IL-31 antigen binding molecules or IL-31 antagonists described herein may be used to improve clinical outcome of prurigo nodularis by inhibition, reduction, prevention or blocking the inflammation and/or scratching associated with disease.

Skin-Tropic Viruses and Viral Associated Pruritis

Herpes Simplex Virus (HSV)-specific CD8+ T cells in the peripheral blood and HSV-specific CD8+ T cells recovered from herpes lesions express high levels of CLA where as non-skin-tropic herpes virus-specific CD8+ T cells lack CLA expression. See Koelle D. M., et al., *J Clin Invest:* 110, 537 (2002). HSV-2 reactive CD4+ T lymphocytes also express CLA, but at levels lower than those previously observed for CD8+ T lymphocytes. See Gonzalez J. C., et al., *J Infect Dis:* 191, 243 (2005). Pruritis has also been associated with herpes viral infections (See Hung K. Y., et al., *Blood Purif:* 16, 147 (1998). though other viral diseases, like HIV, have also been associated with pruritic skin lesions. Severe, intractable pruritus, often associated with erythematopapular skin lesions and hypereosinophilia, is a condition observed in some non-atopic, HIV-infected patients 36. See Singh F. & Rudikoff D, *Am J Clin Dermatol;* 4, 177 (2003); and Milazzo F., Piconi S., et al., *Allergy:* 54, 266 (1999).

The association of skin-tropic viruses with pruritis and CLA+ T cells suggests that IL-31 producing T cells may be involved in the pathophysiology of viral infections.

Thus, neutralization of IL-31 by the humanized IL-31 antigen binding molecules or IL-31 antagonists described herein may be used to improve clinical outcome of pruritis associated with skin-tropic viruses by inhibition, reduction, prevention or blocking the inflammation and/or scratching associated with disease.

Moreover, inflammation is a protective response by an organism to fend off an invading agent. Inflammation is a cascading event that involves many cellular and humoral mediators. On one hand, suppression of inflammatory responses can leave a host immunocompromised; however, if left unchecked, inflammation can lead to serious complications including chronic inflammatory diseases (e.g., rheumatoid arthritis, multiple sclerosis, inflammatory bowel disease and the like), septic shock and multiple organ failure. Importantly, these diverse disease states share common inflammatory mediators. The collective diseases that are characterized by inflammation have a large impact on human morbidity and mortality. Therefore it is clear that anti-inflammatory antibodies and binding polypeptides, such as anti-IL-31 antibodies and binding polypeptides described herein, could have crucial therapeutic potential for a vast number of human and animal diseases, from asthma and allergy to autoimmunity and septic shock. As such, use of anti-inflammatory anti IL-31 antibodies and binding polypeptides described herein can be used therapeutically as IL-31 antagonists described herein, particularly in diseases such as arthritis, endotoxemia, inflammatory bowel disease, psoriasis, related disease and the like.

1. Arthritis

Arthritis, including osteoarthritis, rheumatoid arthritis, arthritic joints as a result of injury, and the like, are common inflammatory conditions which would benefit from the therapeutic use of anti-inflammatory antibodies and binding polypeptides, such as anti-IL-31 antibodies and binding polypeptides of the present invention. For Example, rheumatoid arthritis (RA) is a systemic disease that affects the entire body and is one of the most common forms of arthritis. It is characterized by the inflammation of the membrane lining the joint, which causes pain, stiffness, warmth, redness and swelling. Inflammatory cells release enzymes that may digest bone and cartilage. As a result of rheumatoid arthritis, the inflamed joint lining, the synovium, can invade and damage bone and cartilage leading to joint deterioration and severe pain amongst other physiologic effects. The involved joint can lose its shape and alignment, resulting in pain and loss of movement.

Rheumatoid arthritis (RA) is an immune-mediated disease particularly characterized by inflammation and subsequent tissue damage leading to severe disability and increased mortality. A variety of cytokines are produced locally in the rheumatoid joints. Numerous studies have demonstrated that IL-1 and TNF-alpha, two prototypic pro-inflammatory cytokines, play an important role in the mechanisms involved in synovial inflammation and in progressive joint destruction. Indeed, the administration of TNF-alpha and IL-1 inhibitors in patients with RA has led to a dramatic improvement of clinical and biological signs of inflammation and a reduction of radiological signs of bone erosion and cartilage destruction. However, despite these encouraging results, a significant percentage of patients do not respond to these agents, suggesting that other mediators are also involved in the pathophysiology of arthritis (Gabay, *Expert. Opin. Biol. Ther.* 2(2): 135-149, 2002). One of those mediators could be IL-31, and as such a molecule that binds or inhibits IL-31, such as anti IL-31 antibodies or binding partners, could serve as a valuable therapeutic to reduce inflammation in rheumatoid arthritis, and other arthritic diseases.

There are several animal models for rheumatoid arthritis known in the art. For example, in the collagen-induced arthritis (CIA) model, mice develop chronic inflammatory arthritis that closely resembles human rheumatoid arthritis. Since CIA shares similar immunological and pathological features with RA, this makes it an ideal model for screening potential human anti-inflammatory compounds. The CIA model is a well-known model in mice that depends on both an immune response, and an inflammatory response, in order to occur. The immune response comprises the interaction of B-cells and CD4+ T-cells in response to collagen, which is given as antigen, and leads to the production of anti-collagen antibodies. The inflammatory phase is the result of tissue responses from mediators of inflammation, as a consequence of some of these antibodies cross-reacting to the mouse's native collagen and activating the complement cascade. An advantage in using the CIA model is that the basic mechanisms of pathogenesis are known. The relevant T-cell and B-cell epitopes on type II collagen have been identified, and various immunological (e.g., delayed-type hypersensitivity and anti-collagen antibody) and inflammatory (e.g., cytokines, chemokines, and matrix-degrading enzymes) parameters relating to immune-mediated arthritis have been determined, and can thus be used to assess test compound efficacy in the CIA model (Wooley, *Curr. Opin. Rheum.* 3:407-20, 1999; Williams et al., *Immunol.* 89:9784-788, 1992; Myers et al., *Life Sci.* 61:1861-78, 1997; and Wang et al., *Immunol.* 92:8955-959, 1995).

As a molecule that modulates immune and inflammatory response, IL-31 may induce production of SAA, which is implicated in the pathogenesis of rheumatoid arthritis. Humanized IL-31 antigen binding molecules or IL-31 antagonists may reduce SAA activity in vitro and in vivo, the systemic or local administration of IL-31 antigen binding molecules or IL-31 antagonists can potentially suppress the inflammatory response in RA.

2. Endotoxemia

Endotoxemia is a severe condition commonly resulting from infectious agents such as bacteria and other infectious disease agents, sepsis, toxic shock syndrome, or in immunocompromised patients subjected to opportunistic infections, and the like. Therapeutically useful of anti-inflammatory antibodies and binding polypeptides, such as anti-IL-31 antibodies and binding polypeptides of the present invention, could aid in preventing and treating endotoxemia in humans and animals. Other potential therapeutics include IL-31RA polypeptides, soluble heterodimeric and multimeric receptor polypeptides, or anti IL-31 antibodies or binding partners of the present invention, and the like, could serve as a valuable therapeutic to reduce inflammation and pathological effects in endotoxemia.

Lipopolysaccharide (LPS) induced endotoxemia engages many of the proinflammatory mediators that produce pathological effects in the infectious diseases and LPS induced endotoxemia in rodents is a widely used and acceptable model for studying the pharmacological effects of potential pro-inflammatory or immunomodulating agents. LPS, produced in gram-negative bacteria, is a major causative agent in the pathogenesis of septic shock (Glausner et al., *Lancet* 338:732, 1991). A shock-like state can indeed be induced experimentally by a single injection of LPS into animals. Molecules produced by cells responding to LPS can target pathogens directly or indirectly. Although these biological responses protect the host against invading pathogens, they may also cause harm. Thus, massive stimulation of innate immunity, occurring as a result of severe Gram-negative bacterial infection, leads to excess production of cytokines and other molecules, and the development of a fatal syndrome, septic shock syndrome, which is characterized by fever, hypotension, disseminated intravascular coagulation, and multiple organ failure (Dumitru et al. *Cell* 103:1071-1083, 2000).

These toxic effects of LPS are mostly related to macrophage activation leading to the release of multiple inflammatory mediators. Among these mediators, TNF appears to play a crucial role, as indicated by the prevention of LPS toxicity by the administration of neutralizing anti-TNF antibodies (Beutler et al., *Science* 229:869, 1985). It is well established that 1 ug injection of *E. coli* LPS into a C57Bl/6 mouse will result in significant increases in circulating IL-6, TNF-alpha, IL-1, and acute phase proteins (for example, SAA) approximately 2 hours post injection. The toxicity of LPS appears to be mediated by these cytokines as passive immunization against these mediators can result in decreased mortality (Beutler et al., *Science* 229:869, 1985). The potential immunointervention strategies for the prevention and/or treatment of septic shock include anti-TNF mAb, IL-1 receptor antagonist, LIF, IL-10, and G-CSF. Since LPS induces the production of pro-inflammatory factors possibly contributing to the pathology of endotoxemia, the neutralization of IL-31 activity, SAA or other pro-inflammatory factors by antagonizing IL-31 polypeptide can be used to reduce the symptoms of endotoxemia, such as seen in endotoxic shock. Other potential therapeutics include humanized IL-31 antigen binding molecules or IL-31 antagonists.

3. Inflammatory Bowel Disease. IBD

Inflammatory Bowel Disease (IBD) can affect either colon and rectum (Ulcerative colitis) or both, small and large intestine (Crohn's Disease). The pathogenesis of these diseases is unclear, but they involve chronic inflammation of the affected tissues. Potential therapeutics include IL-31RA polypeptides, soluble heterodimeric and multimeric receptor polypeptides, or anti-IL-31 antibodies or binding partners of the present invention, and the like, could serve as a valuable therapeutic to reduce inflammation and pathological effects in IBD and related diseases.

The chronic inflammation and ulceration in Crohn's disease usually starts with either small-intestinal obstruction or abdominal pain which may mimic acute appendicitis; other presentations can relate to its complications. The course of the disease is chronic, and there may be exacerbations and remissions in spite of therapy. Onset is usually in early adult life, with about half of all cases beginning between the ages of 20 and 30 years and 90% between 10 and 40 years. Slightly more males than females are affected.

Microscopy reflects the gross appearances. Inflammation involvement is discontinuous: it is focal or patchy. Collections of lymphocytes and plasma cells are found mainly in the mucosa and submucosa but usually affecting all layers (transmural inflammation). The classical microscopic feature of Crohn's disease is the presence of granule cells surrounded by a cuff of lymphocytes. The incidence of idiopathic inflammatory bowel diseases shows considerable geographic variation. These diseases have a much higher incidence in northern Europe and the United States than in countries of southern Europe, Africa, South America and Asia, although increasing urbanisation and prosperity is leading to a higher incidence in parts of southern Europe and Japan (General and Systematic Pathology, Churchill Livingstone, 3rd edition 2000, JCE Underwood, Ed.).

In Crohn's disease, clinically there are two main groups, the first comprising patients whose disease goes into lasting remission within three years of onset, the second comprising patients with disease persisting beyond three years.

Whatever the aetiology, there is evidence of persistence and inappropriate T-cell and macrophage activation in Crohn's disease with increased production of pro-inflammatory cytokines, in particular interleukins (IL) 1, 2, 6 and 8, Interferon (IFN)— and Tumor Necrosis Factor (TNF). Crohn's disease is characterised by sustained (chronic) inflammation accompanied by fibrosis. The process of fibroblastic proliferation and collagen deposition may be mediated by transforming growth factor, which has certain anti-inflammatory actions, namely fibroblast recruitment, matrix synthesis and down-regulation of inflammatory cells, but it is likely that many other mediators will be implicated Ulcerative colitis (UC) is an inflammatory disease of the large intestine, commonly called the colon, characterized by inflammation and ulceration of the mucosa or innermost lining of the colon. This inflammation causes the colon to empty frequently, resulting in diarrhea. Symptoms include loosening of the stool and associated abdominal cramping, fever and weight loss. Although the exact cause of UC is unknown, recent research suggests that the body's natural defenses are operating against proteins in the body which the body thinks are foreign (an "autoimmune reaction"). Perhaps because they resemble bacterial proteins in the gut, these proteins may either instigate or stimulate the inflammatory process that begins to destroy the lining of the colon. As the lining of the colon is destroyed, ulcers form releasing mucus, pus and blood. The disease usually begins in the rectal area and may eventually extend through the entire large bowel. Repeated episodes of inflammation lead to thickening of the wall of the intestine and rectum with scar tissue. Death of colon tissue or sepsis may occur with severe disease. The symptoms of ulcerative colitis vary in severity and their onset may be gradual or sudden. Attacks may be provoked by many factors, including respiratory infections or stress.

Although there is currently no cure for UC available, treatments are focused on suppressing the abnormal inflammatory process in the colon lining Treatments including corticosteroids immunosuppressives (eg. azathioprine, mercaptopurine, and methotrexate) and aminosalicytates are available to treat the disease. However, the long-term use of immunosuppressives such as corticosteroids and azathioprine can result in serious side effects including thinning of bones, cataracts, infection, and liver and bone marrow effects. In the patients in whom current therapies are not successful, surgery is an option. The surgery involves the removal of the entire colon and the rectum.

There are several animal models that can partially mimic chronic ulcerative colitis. The most widely used model is the 2,4,6-trinitrobenesulfonic acid/ethanol (TNBS) induced colitis model, which induces chronic inflammation and ulceration in the colon. When TNBS is introduced into the colon of susceptible mice via intra-rectal instillation, it induces T-cell mediated immune response in the colonic mucosa, in this case leading to a massive mucosal inflammation characterized by the dense infiltration of T-cells and macrophages throughout the entire wall of the large bowel. Moreover, this histopathologic picture is accompanies by the clinical picture of progressive weight loss (wasting), bloody diarrhea, rectal prolapse, and large bowel wall thickening (Neurath et al. *Intern. Rev. Immunol.* 19:51-62, 2000).

Another colitis model uses dextran sulfate sodium (DSS), which induces an acute colitis manifested by bloody diarrhea, weight loss, shortening of the colon and mucosal ulceration with neutrophil infiltration. DSS-induced colitis is characterized histologically by infiltration of inflammatory cells into the lamina propria, with lymphoid hyperplasia, focal crypt damage, and epithelial ulceration. These changes are thought to develop due to a toxic effect of DSS on the epithelium and by phagocytosis of lamina propria cells and production of TNF-alpha and IFN-gamma. Despite its common use, several issues regarding the mechanisms of DSS about the relevance to the human disease remain unresolved. DSS is regarded as a T cell-independent model because it is observed in T cell-deficient animals such as SCID mice.

The administration of humanized IL-31 antigen binding molecules or IL-31 antagonists to these TNBS or DSS models can be used to evaluate the use of IL-31 antagonists to ameliorate symptoms and alter the course of gastrointestinal disease. IL-31 may play a role in the inflammatory response in colitis, and the neutralization of IL-31 activity by administrating humanized IL-31 antigen binding molecules or IL-31 antagonists is a potential therapeutic approach for IBD.

4. Psoriasis

Psoriasis is a chronic skin condition that affects more than seven million Americans. Psoriasis occurs when new skin cells grow abnormally, resulting in inflamed, swollen, and scaly patches of skin where the old skin has not shed quickly enough. Plaque psoriasis, the most common form, is characterized by inflamed patches of skin ("lesions") topped with silvery white scales. Psoriasis may be limited to a few plaques or involve moderate to extensive areas of skin, appearing most commonly on the scalp, knees, elbows and trunk. Although it is highly visible, psoriasis is not a contagious disease. The pathogenesis of the diseases involves chronic inflammation of the affected tissues. Humanized IL-31 antigen binding molecules or IL-31 antagonists could serve as a valuable therapeutic to reduce inflammation and pathological effects in psoriasis, other inflammatory skin diseases, skin and mucosal allergies, and related diseases.

Psoriasis is a T-cell mediated inflammatory disorder of the skin that can cause considerable discomfort. It is a disease for which there is no cure and affects people of all ages. Psoriasis affects approximately two percent of the populations of European and North America. Although individuals with mild psoriasis can often control their disease with topical agents, more than one million patients worldwide require ultraviolet or systemic immunosuppressive therapy. Unfortunately, the inconvenience and risks of ultraviolet radiation and the toxicities of many therapies limit their long-term use. Moreover, patients usually have recurrence of psoriasis.

IL-31 was isolated from tissue known to have important immunological function and which contain cells that play a role in the immune system. IL-31 is expressed in CD3+ selected, activated peripheral blood cells, and it has been shown that IL-31 expression increases after T cell activation. Moreover, humanized IL-31 antigen binding molecules or IL-31 antagonists can have an effect on the growth/expansion of monocytes/macrophages, T-cells, B-cells, NK cells and/or differentiated state of monocytes/macrophages, T-cells, B-cells, NK cells or these cells' progenitors. Factors that both stimulate proliferation of hematopoietic progenitors and activate mature cells are generally known, however, proliferation and activation can also require additional growth factors. For example, it has been shown that IL-7 and Steel Factor (c-kit ligand) were required for colony formation of NK progenitors. IL-15+IL-2 in combination with IL-7 and Steel Factor was more effective (Mrozek et al., Blood 87:2632-2640, 1996). However, unidentified cytokines may be necessary for proliferation of specific subsets of NK cells and/or NK progenitors (Robertson et. al., *Blood* 76:2451-2438, 1990). Similarly, IL-31 may act alone or in concert or synergy with other cytokines to enhance growth, proliferation expansion and modification of differentiation of monocytes/macrophages, T-cells, B-cells or NK cells.

The present invention is directed toward use of humanized IL-31 antigen binding molecules or IL-31 antagonists as antagonists in inflammatory and immune diseases or conditions such as atopic dermatitis, pruritic diseases, pancreatitis, type I diabetes (IDDM), pancreatic cancer, pancreatitis, Graves Disease, inflammatory bowel disease (IBD), Crohn's Disease, colon and intestinal cancer, diverticulosis, autoimmune disease, sepsis, organ or bone marrow transplant; inflammation due to trauma, surgery or infection; amyloidosis; splenomegaly; graft versus host disease; and where inhibition of inflammation, immune suppression, reduction of proliferation of hematopoietic, immune, inflammatory or lymphoid cells, macrophages, T-cells (including Th1 and Th2 cells, CD4+ and CD8+ cells), suppression of immune response to a pathogen or antigen. Moreover the presence of IL-31RA expression in activated immune cells such as activated CD4+ and CD19+ cells showed that IL-31RA receptor may be involved in the body's immune defensive reactions against foreign invaders: such as microorganisms and cell debris, and could play a role in immune responses during inflammation and cancer formation. As such, antibodies and binding partners of the present invention that are agonistic or antagonistic to IL-31RA receptor function, such as IL-31, can be used to modify immune response and inflammation.

Humanized IL-31 antigen binding molecules or IL-31 antagonists may also be used within diagnostic systems for the detection of circulating levels of IL-31. Within a related embodiment, antibodies or other agents that specifically bind to IL-31 polypeptides can be used to detect circulating IL-31 polypeptides. Elevated or depressed levels of ligand polypeptides may be indicative of pathological conditions, including cancer. IL-31 polypeptides may contribute to pathologic processes and can be an indirect marker of an underlying disease.

In atherosclerotic lesions, one of the first abnormalities is localization of monocyte/macrophages to endothelial cells. These lesions could be prevented by use of antagonists to IL-31. Humanized IL-31 antigen binding molecules or IL-31 antagonists can be used as antagonists of IL-31 in atherosclerotic lesions. Moreover, monoblastic leukemia is associated with a variety of clinical abnormalities that reflect the release of the biologic products of the macrophage, examples include high levels of lysozyme in the serum and urine and high fevers. Moreover, such leukemias exhibit an abnormal increase of monocytic cells. These effects could possibly be prevented by antagonists to IL-31, such as those described herein. Moreover, humanized IL-31 antigen binding molecules or IL-31 antagonists can be conjugated to molecules such as toxic moieties and cytokines, as described herein to direct the killing of leukemia monocytic cells.

IL-31 has been shown to be expressed in activated mononuclear cells, and may be involved in regulating inflammation. As such, polypeptides of the present invention can be assayed and used for their ability to modify inflammation, or can be used as a marker for inflammation. Methods to determine proinflammatory and antiinflammatory qualities of IL-31 are known in the art and discussed herein. Moreover, it may be involved in up-regulating the production of acute phase reactants, such as serum amyloid A (SAA), α1-antichymotrypsin, and haptoglobin, and that expression of IL-31RA receptor ligand may be increased upon injection of lipopolysaccharide (LPS) in vivo that are involved in inflammatory response (Dumoutier, L. et al., *Proc. Nat'l. Acad. Sci.* 97:10144-10149, 2000). Production of acute phase proteins, such as SAA, is considered s short-term survival mechanism where inflammation is beneficial; however, maintenance of acute phase proteins for longer periods contributes to chronic inflammation and can be harmful to human health. For review, see Uhlar, C M and Whitehead, A S, *Eur. J. Biochem.* 265:501-523, 1999, and Baumann H. and Gauldie, *J. Immunology Today* 15:74-80, 1994. Moreover, the acute phase protein SAA is implicated in the pathogenesis of several chronic inflammatory diseases, is implicated in atherosclerosis and rheumatoid arthritis, and is the precursor to the amyloid A protein deposited in amyloidosis (Uhlar, C M and Whitehead, supra.). Thus, where a ligand such as IL-31 that acts as a pro-inflammatory molecule and induces production of SAA, humanized IL-31 antigen binding molecules or IL-31 antagonists would be useful in treating inflammatory disease and other diseases associated with acute phase response proteins induced by the ligand. For example, a method of reducing inflammation comprises administering to a mammal with inflammation or itch an amount of a composition of humanized IL-31 antigen binding molecules or IL-31 antagonists that is sufficient to reduce the inflammation or itch. Moreover, a method of suppressing an inflammatory response in a mammal with inflammation can comprise: (1) determining a level of serum amyloid A protein; (2) administering a composition comprising a humanized IL-31 antigen binding molecules or IL-31 antagonists as described herein in an acceptable pharmaceutical carrier; (3) determining a post administration level of serum amyloid A protein; (4) comparing the level of serum amyloid A protein in step (1) to the level of serum amyloid A protein in step (3), wherein a lack of increase or a decrease in serum amyloid A protein level is indicative of suppressing an inflammatory response.

Tissue distribution of the mRNA corresponding it's IL-31RA receptor cDNA showed that mRNA level was highest in monocytes and prostate cells, and is elevated in activated monocytes, and activated CD4+, activated CD8+, and activated CD3+ cells. Hence, IL-31RA receptor is also implicated in inducing inflammatory and immune response. Thus, particular embodiments of the present invention are directed toward use of humanized IL-31 antigen binding molecules or IL-31 antagonists in inflammatory and immune diseases or conditions such as, pancreatitis, type I diabetes (IDDM), pancreatic cancer, pancreatitis, Graves Disease, inflammatory bowel disease (IBD), Crohn's Disease, colon and intestinal cancer, diverticulosis, autoimmune disease, sepsis, organ or bone marrow transplant; inflammation due to trauma, surgery or infection; amyloidosis; splenomegaly; graft versus host disease; and where inhibition of inflammation, immune suppression, reduction of proliferation of hematopoietic, immune, inflammatory or lymphoid cells, macrophages, T-cells (including Th1 and Th2 cells, CD4+ and CD8+ cells), suppression of immune response to a pathogen or antigen. Moreover the presence of IL-31RA receptor and IL-31 expression in activated immune cells such as activated CD3+, monocytes, CD4+ and CD19+ cells showed that IL-31RA receptor may be involved in the body's immune defensive reactions against foreign invaders: such as microorganisms and cell debris, and could play a role in immune responses during inflammation and cancer formation. As such, humanized IL-31 antigen binding molecules or IL-31 antagonists of the present invention that are agonistic or antagonistic to IL-31RA receptor function, can be used to modify immune response and inflammation.

Humanized IL-31 antigen binding molecules or IL-31 antagonists are useful to:

1) Antagonize or block signaling via IL-31RA-comprising receptors in the treatment of acute inflammation, inflammation as a result of trauma, tissue injury, surgery, sepsis or infection, and chronic inflammatory diseases such as asthma, inflammatory bowel disease (IBD), chronic colitis, splenomegaly, rheumatoid arthritis, recurrent acute inflammatory episodes (e.g., tuberculosis), and treatment of amyloidosis, and atherosclerosis, Castleman's Disease, asthma, and other diseases associated with the induction of acute-phase response; and 2) Antagonize or block signaling via the IL-31RA receptor receptors in the treatment of autoimmune diseases such as IDDM, multiple sclerosis (MS), systemic Lupus erythematosus (SLE), myasthenia gravis, rheumatoid arthritis, and IBD to prevent or inhibit signaling in immune cells (e.g. lymphocytes, monocytes, leukocytes) via IL-31RA receptor (Hughes C et al., *J Immunol* 153: 3319-3325, 1994). Alternatively antibodies, such as monoclonal antibodies (MAb) to IL-31, can also be used as an antagonist to deplete unwanted immune cells to treat autoimmune disease. Asthma, allergy and other atopic disease may be treated with an MAb against, for example, anti-IL-31 antibodies, soluble IL-31RA receptor soluble receptors or IL-31RA/CRF2-4 heterodimers, to inhibit the immune response or to deplete offending cells. Blocking or inhibiting signaling via IL-31RA, using the polypeptides and antibodies of the present invention, may also benefit diseases of the pancreas, kidney, pituitary and neuronal cells. IDDM, NIDDM, pancreatitis, and pancreatic carcinoma may benefit. IL-31RA may serve as a target for MAb therapy of cancer where an antagonizing MAb inhibits cancer growth and targets immune-mediated killing. (Holliger P, and Hoogenboom, H: *Nature Biotech.* 16: 1015-1016, 1998). Mabs to soluble IL-31RA receptor monomers, homodimers, heterodimers and multimers may also be useful to treat nephropathies such as glomerulosclerosis, membranous neuropathy, amyloidosis (which also affects the kidney among other tissues), renal arteriosclerosis, glomerulonephritis of various origins, fibroproliferative diseases of the kidney, as well as kidney dysfunction associated with SLE, IDDM, type II diabetes (NIDDM), renal tumors and other diseases.

Generally, the dosage of administered humanized IL-31 antigen binding molecules or IL-31 antagonists will vary depending upon such factors as the patient's age, weight, height, sex, general medical condition and previous medical history. Typically, it is desirable to provide the recipient with a dosage of IL-31 polypeptide which is in the range of from about 1 pg/kg to 10 mg/kg (amount of agent/body weight of patient), although a lower or higher dosage also may be administered as circumstances dictate. One skilled in the art can readily determine such dosages, and adjustments thereto, using methods known in the art.

Administration of a humanized IL-31 antigen binding molecules or IL-31 antagonists to a subject can be topical, inhaled, intravenous, intraarterial, intraperitoneal, intramuscular, subcutaneous, intrapleural, intrathecal, by perfusion through a regional catheter, or by direct intralesional injection. When administering therapeutic proteins by injection, the administration may be by continuous infusion or by single or multiple boluses.

Additional routes of administration include oral, mucosal-membrane, pulmonary, and transcutaneous. Oral delivery is suitable for polyester microspheres, zein microspheres, proteinoid microspheres, polycyanoacrylate microspheres, and lipid-based systems (see, for example, DiBase and Morrel, "Oral Delivery of Microencapsulated *Proteins*," in *Protein Delivery: Physical Systems*, Sanders and Hendren (eds.), pages 255-288 (Plenum Press 1997)). The feasibility of an intranasal delivery is exemplified by such a mode of insulin administration (see, for example, Hinchcliffe and Illum, *Adv. Drug Deliv. Rev.* 35:199 (1999)). Dry or liquid particles comprising IL-31 can be prepared and inhaled with the aid of dry-powder dispersers, liquid aerosol generators, or nebulizers (e.g., Pettit and Gombotz, *TIBTECH* 16:343 (1998); Patton et al., *Adv. Drug Deliv. Rev.* 35:235 (1999)). This approach is illustrated by the AERX diabetes management system, which is a hand-held electronic inhaler that delivers aerosolized insulin into the lungs. Studies have shown that proteins as large as 48,000 kDa have been delivered across skin at therapeutic concentrations with the aid of low-frequency ultrasound, which illustrates the feasibility of transcutaneous administration (Mitragotri et al., *Science* 269:850 (1995)). Transdermal delivery using electroporation provides another means to administer a molecule having IL-31 binding activity (Potts et al., *Pharm. Biotechnol.* 10:213 (1997)).

A pharmaceutical composition comprising humanized IL-31 antigen binding molecules or IL-31 antagonists having IL-31 binding activity can be formulated according to known methods to prepare pharmaceutically useful compositions, whereby the therapeutic proteins are combined in a mixture with a pharmaceutically acceptable carrier. A composition is said to be a "pharmaceutically acceptable carrier" if its administration can be tolerated by a recipient patient. Sterile phosphate-buffered saline is one example of a pharmaceutically acceptable carrier. Other suitable carriers are well-known to those in the art. See, for example, Gennaro (ed.), *Remington's Pharmaceutical Sciences,* 19th Edition (Mack Publishing Company 1995).

For purposes of therapy, molecules having IL-31 binding activity and a pharmaceutically acceptable carrier are administered to a patient in a therapeutically effective amount. A combination of a protein, polypeptide, or peptide having IL-31 binding activity and a pharmaceutically acceptable carrier is said to be administered in a "therapeutically effective amount" if the amount administered is physiologically significant. An agent is physiologically significant if its presence results in a detectable change in the physiology of a recipient patient. For example, an agent used to treat inflammation is physiologically significant if its presence alleviates at least a portion of the inflammatory response.

A pharmaceutical composition comprising humanized IL-31 antigen binding molecules or IL-31 antagonists can be furnished in liquid form, in an aerosol, or in solid form. Liquid forms, are illustrated by injectable solutions, aerosols, droplets, topological solutions and oral suspensions. Exemplary solid forms include capsules, tablets, and controlled-release forms. The latter form is illustrated by miniosmotic pumps and implants (Bremer et al., *Pharm. Biotechnol.* 10:239 (1997); Ranade, "Implants in Drug Delivery," in *Drug Delivery Systems*, Ranade and Hollinger (eds.), pages 95-123 (CRC Press 1995); Bremer et al., "Protein Delivery with Infusion Pumps," in *Protein Delivery: Physical Systems*, Sanders and Hendren (eds.), pages 239-254 (Plenum Press 1997); Yewey et al., "Delivery of Proteins from a Controlled Release Injectable Implant," in *Protein Delivery Physical Systems*, Sanders and Hendren (eds.), pages 93-117 (Plenum Press 1997)). Other solid forms include creams, pastes, other topological applications, and the like.

The humanized IL-31 antigen binding molecules or IL-31 antagonists disclosed herein may also be formulated as immunoliposomes. Liposomes containing the antibody are prepared by methods known in the art, such as described in Epstein et al., Proc. Natl. Acad. Sci. USA, 82: 3688 (1985); Hwang et al., Proc. Natl. Acad. Sci. USA, 77: 4030 (1980); and U.S. Pat. Nos. 4,485,045 and 4,544,545. Liposomes with enhanced circulation time are disclosed in U.S. Pat. No. 5,013,556.

Liposomes provide one means to deliver therapeutic polypeptides to a subject intravenously, intraperitoneally, intrathecally, intramuscularly, subcutaneously, or via oral administration, inhalation, or intranasal administration. Liposomes are microscopic vesicles that consist of one or more lipid bilayers surrounding aqueous compartments (see, generally, Bakker-Woudenberg et al., *Eur. J. Clin. Microbiol. Infect. Dis.* 12 (Suppl. 1):S61 (1993), Kim, *Drugs* 46:618 (1993), and Ranade, "Site-Specific Drug Delivery Using Liposomes as Carriers," in *Drug Delivery Systems*, Ranade and Hollinger (eds.), pages 3-24 (CRC Press 1995)). Liposomes are similar in composition to cellular membranes and as a result, liposomes can be administered safely and are biodegradable. Depending on the method of preparation, liposomes may be unilamellar or multilamellar, and liposomes can vary in size with diameters ranging from 0.02 µm to greater than 10 µm. A variety of agents can be encapsulated in liposomes: hydrophobic agents partition in the bilayers and hydrophilic agents partition within the inner aqueous space(s) (see, for example, Machy et al., *Liposomes In Cell Biology And Pharmacology* (John Libbey 1987), and Ostro et al., *American J. Hosp. Pharm.* 46:1576 (1989)). Moreover, it is possible to control the therapeutic availability of the encapsulated agent by varying liposome size, the number of bilayers, lipid composition, as well as the charge and surface characteristics of the liposomes.

Particularly useful liposomes can be generated by the reverse phase evaporation method with a lipid composition comprising phosphatidylcholine, cholesterol and PEG-derivatized phosphatidylethanolamine (PEG-PE). Liposomes are extruded-through filters of defined pore size to yield liposomes with the desired diameter. Fab' fragments of the antibody of the present invention can be conjugated to the liposomes as described in Martin et al. *J. Biol. Chem.* 257: 286-288 (1982) via a disulfide interchange reaction. A chemotherapeutic agent (such as Doxorubicin) is optionally contained within the liposome. See Gabizon et al. J. National Cancer Inst. 81(19) 1484 (1989).

Therapeutic formulations of the humanized IL-31 antigen binding molecules or IL-31 antagonists are prepared for storage by mixing the antibody having the desired degree of purity with optional physiologically acceptable carriers, excipients or stabilizers (Remington's Pharmaceutical Sciences 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as Tween™, Pluronics™ or polyethylene glycol (PEG).

The formulation herein may also contain more than one active compound as necessary for the particular indication being treated, preferably those with complementary activities that do not adversely affect each other. For example, it may be desirable to further provide antibodies which bind to IL-31 in the one formulation. Alternatively, or in addition, the composition may comprise a chemotherapeutic agent or a cytokine. Such molecules are suitably present in combination in amounts that are effective for the purpose intended.

Polypeptides having IL-31 binding activity can be encapsulated within liposomes using standard techniques of protein microencapsulation (see, for example, Anderson et al., *Infect. Immun.* 31:1099 (1981), Anderson et al., *Cancer Res.* 50:1853 (1990), and Cohen et al., *Biochim. Biophys. Acta* 1063:95 (1991), Alving et al. "Preparation and Use of Liposomes in Immunological Studies," in *Liposome Technology*, 2nd Edition, Vol. III, Gregoriadis (ed.), page 317 (CRC Press 1993), Wassef et al., *Meth. Enzymol.* 149:124 (1987)). As noted above, therapeutically useful liposomes may contain a variety of components. For example, liposomes may comprise lipid derivatives of poly(ethylene glycol) (Allen et al., *Biochim Biophys. Acta* 1150:9 (1993)).

The formulations to be used for in vivo administration must be sterile. This is readily accomplished by filtration through sterile filtration membranes.

Sustained-release preparations may be prepared. Suitable examples of sustained-release preparations include semipermeable matrices of solid hydrophobic polymers containing the antibody, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and .gamma. ethyl-L-glutamate, non-degradable ethylene-vinyl acetate, degradable lactic acid-glycolic acid copolymers such as the Lupron Depot™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

Other dosage forms can be devised by those skilled in the art, as shown, for example, by Ansel and Popovich, *Pharmaceutical Dosage Forms and Drug Delivery Systems*, 5$^{th}$ Edition (Lea & Febiger 1990), Gennaro (ed.), *Remington's Pharmaceutical Sciences*, 19$^{th}$ Edition (Mack Publishing Company 1995), and by Ranade and Hollinger, *Drug Delivery Systems* (CRC Press 1996).

As an illustration, pharmaceutical compositions may be supplied as a kit comprising a container that comprises a humanized IL-31 antigen binding molecule or IL-31 antagonist (e.g., an antibody or antibody fragment that binds a IL-31 polypeptide). Therapeutic polypeptides can be provided in the form of an injectable solution for single or multiple doses, or as a sterile powder that will be reconstituted before injection. Alternatively, such a kit can include a dry-powder disperser, liquid aerosol generator, or nebulizer for administration of a therapeutic polypeptide.

The invention is further illustrated by the following non-limiting examples.

EXAMPLES

Example 1

Determination of Humanized Variable Region Sequences

Mouse anti-human IL-31 monoclonal antibodies are described in co-pending U.S. patent application Ser. No.

11/430,066, filed May 8, 2006 (U.S. Patent Publication No. 2006-02752960). The amino acid sequences of the variable regions of mouse anti-human IL-31 antibodies described in co-pending U.S. patent application Ser. No. 11/850,006, filed Sep. 4, 2007 and co-owned PCT application U.S.07/77555, filed Sep. 4, 2007. These amino acid sequences were used as starting material for the humanized sequences described herein. In specific the mouse anti-human IL-31 antibody sequence was from a hybridoma with the clone number 292.12.3.1.

Nucleotides encoding the CDR regions of clones 292.12.3.1 were cloned into a cDNA vector encoding human IgG such that a chimeric antibodies were generated consisting of a human IgG framework harboring the murine CDR regions. Individual amino acids in the chimeric antibody were optimized to obtain the characteristics of a monoclonal antibody of high quality (binding affinity, stability, and homogenecity). Three dimensional models of each antibody were generated and humanized variable regions and CDR regions were determined.

Constructs containing the humanized mouse anti-human IL-31 heavy and light chain variable regions were fused to a human IgG4 constant region with a Ser to Pro mutation at position 241 (Kabat numbering) to inhibit formation of half antibodies. The constructs were expressed in HEK2923 cells and purified on a protein A column followed by buffer exchange into PBS. Binding affinity was measured by Biacore. Potency was measured in a BAF proliferation assay and a NHK stat3 phosphorylation assay. Biphysical characteristics such as homogenecity, aggregation, and folding stability were evaluated.

Example 2

Expression of Humanized IL-31 Antigen Binding Molecules in HEK293 Cells

All experimental procedures were carried out according to the manufactures instructions. Anti IL-31 antibody cDNA was ordered from Geneart (http://www.Geneart.com) and subcloned into the expression plasmid pTT5. Antibody light chain (LC) and heavy chain (HC) were kept on independent plasmids. pTT5 was licensed from Yves Durocher (Biotechnology Research Institute, National Research Council Canada). The pTT5 plasmid has been characterized in the following publications; Durocher et al. NAR 2002; and Pham et al. Biotechn. Bioeng. 2003.

To obtain plasmid for HEK293-6E transfection, anti IL-31 antibody coding plasmids were chemically transformed into TOP10 *E. coli* cells (cat no. C4040-06, Invitrogen, Taastrup, Denmark) and isolated via plasmid purification columns (cat no. 27144, Qiagen, Ballerup, Denmark). Site-directed amino acid exchange was performed by PCR, with primers from DNA technology, and Dpn1 digest (cat no. 200518, Clontech via Medinova Scientific A/S, Glostrup, Denmark). Plasmids were sequenced at MWG-biotech.

HEK293-6E cells were transfected as described in the 293Fectin protocol (cat no. 12347019, Invitrogen, Taastrup, Denmark). In brief, 15 μg of LC and 15 μg of HC plasmid were diluted in 1 ml of Opti-MEM (cat no. 31985-062, Gibco/Invitrogen, Taastrup, Denmark) and mixed with 40 μl of 293Fectin also diluted in 1 ml Opti-MEM. For a standard transfection 30 million HEK293-6E cells were pelleted and resuspended in 28 ml of Freestyle medium (cat no. 12338, Gibco/Invitrogen, Taastrup, Denmark) and the 2 ml plasmid mix was then added. The cells were hereafter incubated at 37° C., 8% CO2, with agitation (125 rpm) for 6 days before pelleting and supernatant sampling.

Example 3

Binding Affinity of Humanized IL-31 Antigen Binding Molecules Measured by Biacore Introduction Protein interactions can be monitored in real time using surface plasmon resonance (SPR) analysis. In this study we perform SRP analysis on Biacore 3000 and Biacore T100 instruments, in order to characterize the anti-IL-31 monoclonal antibodies with respect to affinity towards recombinant human IL-31 (hIL-31).

Affinity studies were performed using a direct binding procedure, with the monoclonal antibody covalently coupled via free amine groups to the carboxymethylated dextrane membrane (CM5) on the sensor chip surface. Recombinant hIL-31 was injected in various concentrations, followed by a dissociation period with constant buffer flow over the sensor chip surface. Using this experimental design, the binding of hIL-31 to the immobilized monoclonal antibody can be regarded as a 1:1 binding, with one hIL-31 molecule binding to one antibody binding site. The kinetic parameters for the interaction can be calculated using a 1:1 interaction langmuir fitting model.

Method

The purified monoclonal antibodies were immobilized in individual flow cells on a CM5 type sensor chip. Immobilizations were performed using a standard amine coupling procedure, aiming for an immobilization level of 500 Resonance Units (RU). The antibodies were diluted to 1-5 ug/ml in 10 mM NaAc pH 4.5.

HPS-EP pH 7.4 (10 mM HEPES, 150 mM NaCl, 3 mM EDTA and 0.005% Polysorbat P20) was used as running buffer, and diluents for the recombinant hIL-31 (hIL-31, BHK produced, A1277F, zcytor17lig CEE). The hIL-31 was tested in a 3-fold dilution series from 333.3 nM to 1.4 nM. Association (injection) was 4 min., followed by a 20 min. dissociation (wash) period. Flow rate was 50 ul/min. Experiments were performed at 250 C. Regeneration of the surface was accomplished by injection of 30 sec. pulse of 10 mM Glycin-HCl pH 1.8 or 1M formic acid, at a 30 ul/min flow rate. Detection in all flow cells simultaneously. Flow cell #1 contained no immobilized antibody, and was used for subtraction of background and bulk. All experiments were performed in triplicates.

The "parent" murine monoclonal antibody was included in all experiments for internal referencing of the kinetic parameters obtained.

The kinetic parameters were calculated by global fitting of the data using a 1:1 langmuir binding model. Data was inspected for mass-transport limitations prior to calculation of the kinetic parameters. In some experiments the Rmax was fitted locally, and the RI constant at 0.

Experiments were performed on Biacore 3000 and T100 instruments. Data was evaluated using Biaeval 4.1 and Biacore T100 evaluation software. Data is shown in Table 2 and below. Several of the clones showed affinity similar to the parent strain in this assay.

TABLE 2

| Clone Number | KD (nM) | kd (1/s) | ka (1/Ms) | Relative potency loss (KD) | Relative potency loss (kd) |
|---|---|---|---|---|---|
| 292.12.3.1 (parent) | 2.2 | 6.10E−05 | 2.80E+04 | | |
| 7 | 1.9 | 5.70E−05 | 3.30E+04 | Similar to parent | Similar to parent |
| 8 | 1.9 | 5.40E−05 | 2.80E+04 | Similar to parent | Similar to parent |
| 9 | 2.1 | 9.00E−05 | 4.30E+04 | Similar to parent | ~1.5x to parent |
| 10 | 186 | 1.50E−02 | 8.80E+05 | ~85x to parent | ~245x to parent |
| 11 | 1.46 | 7.60E−05 | 5.20E+04 | Similar to parent | Similar to parent |
| 13 | 24 | 3.00E−03 | 1.20E+05 | ~10x to parent | ~50x to parent |
| 14 | 12.5 | 7.30E−04 | 5.90E+04 | ~5.5x to parent | ~12x to parent |
| 16 | 1.2 | 7.50E−05 | 6.10E+04 | ~0.5x to parent | Similar to parent |
| 17 | 0.9 | 6.50E−05 | 7.00E+04 | ~0.4x to parent | Similar to parent |
| 18 | 1.13 | 6.20E−05 | 5.50E+04 | ~0.5x to parent | Similar to parent |
| 21 | 1.4 | 9.70E−05 | 6.90E+04 | Similar to parent | Similar to parent |
| 22 | 1.7 | 1.10E−04 | 6.70E+04 | Similar to parent | ~2x to parent |
| 23 | 1.4 | 9.00E−05 | 6.50E+04 | ~0.6x to parent | ~1.5x to parent |
| 25 | 0.85 | 7.20E−05 | 8.50E+04 | ~0.5x to parent | Similar to parent |
| 26 | 0.68 | 7.00E−05 | 1.00E+05 | ~0.4x to parent | Similar to parent |
| 27 | 0.8 | 7.90E−05 | 9.80E+04 | ~0.5x to parent | ~1.3x to parent |
| 28 | 0.46 | 5.60E−05 | 1.20E+05 | ~0.25x to parent | Similar to parent |
| 29 | 0.99 | 8.98E−05 | 9.00E+04 | ~0.5x to parent | ~1.5x to parent |
| 30 | 1.1 | 9.00E−05 | 7.80E+04 | ~0.5x to parent | ~1.5x to parent |
| 31 | 0.77 | 7.00E−05 | 9.20E+04 | ~0.4x to parent | Similar to parent |
| 32 | 0.64 | 5.90E−05 | 9.30E+04 | ~0.3x to parent | Similar to parent |
| 33 | 1.3 | 6.80E−05 | 5.20E+04 | ~0.6x to parent | Similar to parent |
| 34 | 1.4 | 6.90E−05 | 5.20E+04 | ~0.6x to parent | Similar to parent |
| 35 | 1.6 | 1.00E−04 | 6.40E+04 | ~0.7x to parent | ~1.5x to parent |
| 36 | 1.6 | 1.08E−04 | 6.80E+04 | ~0.5x to parent | ~1.5x to parent |

Example 4

Potency of Humanized IL-31 Antigen Binding Molecules Measured by BAF Proliferation Assay A. Media and Buffers Culture medium: RPMI 1640 with Glutamax (SKN, NN), 10% heat inactivated FBS, 1% P/S (BioWhitaker Cat. No. DE17-602E), 0.5 mg/ml Geneticin (GIBCO Cat. No. 10131-019), 100 µg/ml Zeocin (Invitrogen 45-0430), 1 ng/ml mouse IL3 (TriChem ApS Cat. No. 213-13), 2 ug/ml Pyromycin (Sigma-Aldrich P7255).

Assay medium: RPMI 1640 with Glutamax (SKN, NN), 10% heat inactivated FBS, 1% P/S (BioWhitaker Cat. No. DE17-602E), 0.5 mg/ml Geneticin (GIBCO Cat. No. 10131-019), 100 µg/ml Zeocin (Invitrogen 45-0430), 2 ug/ml Pyromycin (Sigma-Aldrich P7255).

alamarBlue dye (BioScource, Dal1100) is used to assess proliferation.

B. Antibodies, Cells and Cytokines

Human anti-IL-31 monoclonal antibodies were produced at Novo Nordisk and purified at Novo Nordisk (Copenhagen, Denmark). BAF-3(hIL-31R) cells received from ZymoGenetics, Inc. (Seattle, Wash.) as a KZS134-BAF3 cell line transfected with the genes for hIL-31Rα and hOSMRB. Recombinant human IL-31 (C108S, described in U.S. Patent Publication No. 2006-0228329), produced in *E. Coli* by ZymoGenetics, Inc.). MW 18 kDa C. Proliferation Assay 1. Stimulation Assay BAF-3(hIL-31R) cells are washed thoroughly in Assay medium to get rid of residual IL3. The cells are then seeded into 96-well microtiter plates (flat-well view plate Packard cat. S00190) at $10^4$ cells per well. Serial dilutions of hIL-31 ($10^{-9}$M to $10^{-15}$ M) are added to the wells and additional wells with cells but no hIL-31 serves as negative control. The cells are cultured for three days in 5% CO2 at 37° C. For the last 6 hours of the culture period, 10 µl alamarBlue is added to each well. The cells are analyzed for fluorescence intensity on a spectrofluorometer (bmg POLARstar+ Galaxy) at excitation 555-12 nm and emission 590 nm. For inhibition analysis, a constant concentration of hIL-31 is used to stimulate the cells. This concentration was chosen on basis of approximately 90% of max stimulation in the proliferation assay which in our hands means $10^{-10}$M hIL20.

2. Inhibition Assay.

$10 \times 10^4$ cells per well of washed BAF-3(hIL-31R) cells are seeded into microtiter wells in assay medium. $10^{-10}$M (final concentration) of hIL-31 is added to each well (except some wells used as negative control containing only cells). Serial dilutions of antibody (i.e. 100 µg and 2-fold) are added to the wells already containing cells and cytokines (except wells used for positive controls which should contain only cells+hIL-31). The mixture of cells, cytokine and antibody are incubated in 100 µl/w for 72 hours in 5% CO2 at 37° C. The last 6 hours of incubation includes 10 µl/w of alamarBlue. The plates are analysed for fluorescence intensity on a spectrofluorometer (bmg POLARstar+ Galaxy) at excitation 555-12 nm and emission 590 nm. The curves are drawn and the potency (IC50) is calculated using Prism 4 (GraphPad PRISM software Inc.). Data is shown in Table 3 and below. Several of the clones showed potency similar to the parent in this assay.

TABLE 3

Potency (nM) of humanised mAbs at 1E-10M hIL-31

| Clone Number | Average Potency | Average Fold loss in potency relative to 292.12.3.1 |
|---|---|---|
| 292.12.3.1 (parent) | 1.6 | 1.0 |
| 07 | 4.5 | 3.3 |
| 08 | 4.1 | 2.5 |
| 09 | 28.5 | 15.1 |
| 10 | ≫ | ≫ |
| 11 | 22.8 | 11.6 |
| 12 | ≫ | ≫ |
| 13 | 109.0 | 99.1 |
| 14 | ≫ | ≫ |

TABLE 3-continued

Potency (nM) of humanised mAbs at 1E-10M hIL-31

| Clone Number | Average Potency | Average Fold loss in potency relative to 292.12.3.1 |
|---|---|---|
| 15 | 10.4 | 7.7 |
| 16 | 10.6 | 9.8 |
| 17 | 5.9 | 5.2 |
| 18 | 8.1 | 5.9 |
| 20 | >> | >> |
| 21 | 4.8 | 3.5 |
| 22 | 14.0 | 13.2 |
| 23 | 8.6 | 7.6 |
| 24 | 6.0 | 4.0 |
| 25 | 26.3 | 16.5 |
| 26 | 9.3 | 5.8 |
| 27 | 29.1 | 18.7 |
| 28 | 26.4 | 17.1 |
| 29 | 12.9 | 8.3 |
| 30 | 57.8 | 37.1 |
| 31 | 32.4 | 25.1 |
| 32 | 18.9 | 14.7 |
| 33 | 3.1 | 2.3 |
| 35 | 62.1 | 75.1 |
| 36 | 14.1 | — |

Example 5

Potency of Humanized IL-31 Antigen Binding Molecules Measured by NHK Stat3 Phosphorylation Assay Culture of normal human keratinocytes and STAT3 phosphorylation assay:

Normal human keratinocytes (NHKs) from abdominal skin were obtained from Biopredic Int. (Rennes, France) and were grown in Epilife Medium supplemented with the HKGS kit from Cascade Biologics (Portland, Oreg.). A Detach Kit containing HBSS, trypsin-EDTA and trypsin neutralizing reagent was used to harvest cells and was obtained from Promocell (Heidelberg, Germany). NHKs were stimulated for 15 minutes with recombinant human IL-31 in flat-bottomed 96-well plates (Nunc, Roskilde, Denmark) in order to measure STAT3 phosphorylation and determine the EC50 of the cytokine. NHK lysates were tested in PathScan Phospho-STAT3 Sandwich ELISA Kit from Cell Signaling Technology (Danvers, Mass.) according to the manufacturer's instructions. The IC50 of each neutralizing antibody was then determined by adding serial dilutions of antibodies to NHKs prior to stimulation for 15 minutes with an EC80 of recombinant human IL-31. Mouse IgG1 (R&D Systems, Minneapolis, Minn.) and human IgG4 (Sigma-Aldrich, Saint Louis, Mo.) were used as isotypic control antibodies.

Potencies of Antibodies Directed Against Human IL-31

For each antibody directed against human IL-31, IC50 values (nM) are shown in Table 4. For each experiment, a Z' factor as determined with the XL Fit software is given. The stimulation index obtained with an EC80 of recombinant human IL-31 is shown. Several of the clones showed potency similar to the parent or acceptable potency in this assay.

TABLE 4

| | Exp 1 | Exp 2 | Exp 3 | Exp 4 | Exp 6 | Exp 7 | Exp 8 | Exp 9 | Exp 10 |
|---|---|---|---|---|---|---|---|---|---|
| Stimulation Index | 4.97 | 4.22 | 7.61 | 3.63 | 6.00 | 9.05 | 4.08 | 6.79 | 8.70 |
| Z' factor | 0.98 | 0.98 | 0.93 | 0.83 | 0.91 | 0.93 | 0.92 | 0.95 | 0.90 |
| Clone Number | | | | | | | | | |
| 292.12.3.1 (parent) | 0.71 | 1.90 | 3.66 | 8.17 | 4.48 | 5.54 | 5.57 | 7.06 | 13.16 |
| 7 | | | | 7.80 | 3.99 | 7.74 | 5.44 | 7.58 | 8.82 |
| 8 | | | | 6.74 | | | | | 3.44 |
| 9 | | | | | 3.25 | 7.37 | 6.59 | 7.10 | |
| 10 | | | | | 68.83 | 223.87 | | | |
| 13 | | | | | 46.51 | 210.90 | | | |
| 14 | | | | | 71.92 | 242.30 | | | |
| 16 | | | | | 3.84 | 6.22 | | | |
| 17 | | | | | 6.65 | 5.29 | | | |
| 18 | | | | | 2.60 | 2.68 | | | |
| 25 | | | | | | | 5.85 | 7.28 | |
| 26 | | | | | | | 7.84 | 6.93 | |
| 27 | | | | | | | 3.42 | 9.59 | |
| 28 | | | | | | | 10.50 | 5.95 | |
| 29 | | | | | | | 4.49 | 5.37 | |
| 30 | | | | | | | 14.79 | 8.71 | |
| 31 | | | | | | | 11.01 | 7.82 | |
| 32 | | | | | | | 11.53 | 6.43 | |
| 33 | | | | | | | 4.08 | 5.68 | 13.62 |
| 34 | | | | | | | | 5.46 | 8.40 |
| 35 | | | | | | | | | 12.04 |
| 36 | | | | | | | | | 8.95 |

From the foregoing, it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. An isolated nucleic acid molecule encoding a monoclonal antibody that specifically binds to human IL-31, wherein the encoded monoclonal antibody comprises a heavy chain variable domain and a light chain variable domain, wherein the heavy chain variable domain and the light chain variable domain each comprises a complementarity determining region (CDR) and a framework region (FR), wherein the heavy chain variable domain complementarity determining region comprises:
   a) a CDR1 having the amino acid residues of SEQ ID NO:1;
   b) a CDR2 having the amino acid residues of SEQ ID NO:2; and
   c) a CDR3 having the amino acid residues of SEQ ID NO:3;
wherein the heavy chain variable domain framework region comprises:
   d) a FR1 having at least 90% sequence identity with amino acid residues of SEQ ID NO:12;
   e) a FR2 having at least 90% sequence identity with amino acid residues of SEQ ID NO:13;
   f) a FR3 having at least 90% sequence identity with amino acid residues of SEQ ID NO:14; and
   g) a FR4 having at least 90% sequence identity with amino acid residues of SEQ ID NO:15;
wherein the light chain variable domain complementarity determining region comprises:
   h) a CDR1 having the amino acid residues of SEQ ID NO:5;
   i) a CDR2 having the amino acid residues of SEQ ID NO:6; and
   j) a CDR3 having the amino acid residues of SEQ ID NO:7; and
wherein the light chain variable domain framework region comprises:
   k) a FR5 having at least 90% sequence identity with amino acid residues of SEQ ID NO:17;
   l) a FR6 having at least 90% sequence identity with amino acid residues of SEQ ID NO:18;
   m) a FR7 having at least 90% sequence identity with amino acid residues of SEQ ID NO:19; and
   n) a FR8 having at least 90% sequence identity with amino acid residues of SEQ ID NO:20.

2. The isolated nucleic acid molecule of claim 1, wherein the nucleic acid molecule further encodes a human immunoglobulin constant domain.

3. The isolated nucleic acid molecule of claim 2, wherein the human immunoglobulin constant domain is IgG1, IgG2, IgG3 or IgG4.

4. The isolated nucleic acid molecule of claim 2, wherein the human immunoglobulin constant domain is IgG4.

5. An expression vector comprising the following operably linked elements:
   a) a transcription promoter;
   b) the nucleic acid molecule of claim 1; and
   c) a transcription terminator.

6. An expression vector comprising the following operably linked elements:
   a) a first transcription promoter;
   b) a first nucleic acid molecule encoding the heavy chain variable domain of claim 1;

c) a first transcription terminator;
d) a second transcription promoter;
e) a second nucleic acid molecule encoding the light chain variable domain of claim 1; and
f) a second transcription terminator.

7. An expression vector comprising the following operably linked elements:
   a) a first transcription promoter;
   b) a first nucleic acid molecule encoding the heavy chain variable domain of claim 1;
   c) a first transcription terminator;
   d) the first transcription promoter;
   e) a second nucleic acid molecule encoding the light chain variable domain of claim 1; and
   f) a second transcription terminator.

8. A recombinant host cell comprising the expression vector of claim 5.

9. A recombinant host cell comprising the expression vector of claim 6.

10. A recombinant host cell comprising the expression vector of claim 7.

11. A recombinant host cell comprising:
    a) a first expression vector comprising:
       i) a first transcription promoter;
       ii) a first nucleic acid molecule encoding the heavy chain variable domain of claim 1; and
       iii) a first transcription terminator; and
    b) a second expression vector comprising:
       i) a second transcription promoter;
       ii) a second nucleic acid molecule encoding the light chain variable domain of claim 1; and
       iii) a second transcription terminator.

12. A method of producing the IL-31 monoclonal antibody encoded by the nucleic acid molecule in the expression vector of claim 5 comprising:
    a) culturing a host cell comprising said vector under conditions wherein the monoclonal antibody is expressed; and
    b) recovering the monoclonal antibody.

13. A method of producing the IL-31 monoclonal antibody encoded by the nucleic acid molecule in the expression vector of claim 6 comprising:
    a) culturing a host cell comprising said vector under conditions wherein the monoclonal antibody is expressed; and
    b) recovering the monoclonal antibody.

14. A method of producing the IL-31 monoclonal antibody encoded by the nucleic acid molecule in the expression vector of claim 7 comprising:
    a) culturing a host cell comprising said vector under conditions wherein the monoclonal antibody is expressed; and
    b) recovering the monoclonal antibody.

15. A method of producing a IL-31 monoclonal antibody comprising:
    a) culturing the host cell of claim 11 under conditions wherein the heavy and light chain variable domains are expressed; and
    b) recovering the monoclonal antibody.

16. An isolated nucleic acid molecule encoding a monoclonal antibody that specifically binds to human IL-31, wherein the encoded monoclonal antibody comprises a heavy chain variable domain and a light chain variable domain, wherein the heavy chain variable domain comprises the amino acid residues of SEQ ID NO:44 and the light chain variable domain comprises the amino acid residues of SEQ ID NO:26.

17. The isolated nucleic acid molecule of claim 16, wherein the nucleic acid molecule further encodes a human immunoglobulin constant domain.

18. The isolated nucleic acid molecule of claim 17, wherein the human immunoglobulin constant domain is IgG1, IgG2, IgG3 or IgG4.

19. The isolated nucleic acid molecule of claim 17, wherein the human immunoglobulin constant domain is IgG4.

20. An expression vector comprising the following operably linked elements:
    a) a transcription promoter;
    b) the nucleic acid molecule of claim 16; and
    c) a transcription terminator.

21. An expression vector comprising the following operably linked elements:
    a) a first transcription promoter;
    b) a first nucleic acid molecule encoding the heavy chain variable domain of claim 16;
    c) a first transcription terminator;
    d) a second transcription promoter;
    e) a second nucleic acid molecule encoding the light chain variable domain of claim 16; and
    f) a second transcription terminator.

22. An expression vector comprising the following operably linked elements:
    a) a first transcription promoter;
    b) a first nucleic acid molecule encoding the heavy chain variable domain of claim 16;
    c) a first transcription terminator;
    d) the first transcription promoter;
    e) a second nucleic acid molecule encoding the light chain variable domain of claim 16; and
    f) a second transcription terminator.

23. A recombinant host cell comprising the expression vector of claim 20.

24. A recombinant host cell comprising the expression vector of claim 21.

25. A recombinant host cell comprising the expression vector of claim 22.

26. A recombinant host cell comprising:
    a) a first expression vector comprising:
       i) a first transcription promoter;
       ii) a first nucleic acid molecule encoding the chain variable domain of claim 16; and
       iii) a first transcription terminator; and
    b) a second expression vector comprising:
       i) a second transcription promoter;
       ii) a second nucleic acid molecule encoding the light chain variable domain of claim 16; and
       iii) a second transcription terminator.

27. A method of producing the IL-31 monoclonal antibody encoded by the nucleic acid molecule in the expression vector of claim 20 comprising:
    a) culturing a host cell comprising said vector under conditions wherein the monoclonal antibody is expressed; and
    b) recovering the monoclonal antibody.

28. A method of producing the IL-31 monoclonal antibody encoded by the nucleic acid molecule in the expression vector of claim 21 comprising:
    a) culturing a host cell comprising said vector under conditions wherein the monoclonal antibody is expressed; and
    b) recovering the monoclonal antibody.

29. A method of producing the IL-31 monoclonal antibody encoded by the nucleic acid molecule in the expression vector of claim 22 comprising:
   a) culturing a host cell comprising said vector under conditions wherein the monoclonal antibody is expressed; and
   b) recovering the monoclonal antibody.

30. A method of producing a IL-31 monoclonal antibody comprising:
   a) culturing the host cell of claim 26 under conditions wherein the heavy and light chain variable domains are expressed; and
   b) recovering the monoclonal antibody.

* * * * *

```
                          SEQUENCE LISTING

<160> NUMBER OF SEQ ID NOS: 51

<210> SEQ ID NO 1
<211> LENGTH: 5
<212> TYPE: PRT
<213> ORGANISM: Mus musculus

<400> SEQUENCE: 1

Arg Tyr Trp Met Gln
1               5

<210> SEQ ID NO 2
<211> LENGTH: 17
<212> TYPE: PRT
<213> ORGANISM: Mus musculus

<400> SEQUENCE: 2

Ala Ile Tyr Pro Gly Asp Gly Asp Thr Arg Tyr Ser Gln Lys Phe Gln
1               5                  10                  15

Gly

<210> SEQ ID NO 3
<211> LENGTH: 13
<212> TYPE: PRT
<213> ORGANISM: Mus musculus

<400> SEQUENCE: 3

Pro Asp Gly Tyr Tyr Ala Ala Pro Tyr Gly Met Asp Tyr
1               5                  10

<210> SEQ ID NO 4
<211> LENGTH: 17
<212> TYPE: PRT
<213> ORGANISM: Mus musculus

<400> SEQUENCE: 4

Ala Ile Tyr Pro Gly Asp Gly Asp Thr Arg Tyr Ser Pro Ser Phe Gln
1               5                  10                  15

Gly

<210> SEQ ID NO 5
<211> LENGTH: 11
<212> TYPE: PRT
<213> ORGANISM: Mus musculus

<400> SEQUENCE: 5

Arg Ala Ser Gly Asn Ile His Asn Tyr Leu Ala
1               5                  10

<210> SEQ ID NO 6
<211> LENGTH: 7
<212> TYPE: PRT
<213> ORGANISM: Mus musculus

<400> SEQUENCE: 6

Asn Ala Lys Thr Leu Ala Asp
1               5

<210> SEQ ID NO 7
```

```
<211> LENGTH: 9
<212> TYPE: PRT
<213> ORGANISM: Mus musculus

<400> SEQUENCE: 7

Gln His Phe Trp Ser Thr Pro Trp Thr
1               5

<210> SEQ ID NO 8
<211> LENGTH: 30
<212> TYPE: PRT
<213> ORGANISM: Mus musculus
<220> FEATURE:
<221> NAME/KEY: VARIANT
<222> LOCATION: (29)...(29)
<223> OTHER INFORMATION: Xaa is Leu or Phe

<400> SEQUENCE: 8

Glu Val Gln Leu Val Gln Ser Gly Ala Glu Val Lys Lys Pro Gly Glu
1               5                   10                  15

Ser Leu Lys Ile Ser Cys Lys Ala Ser Gly Tyr Thr Xaa Thr
            20                  25                  30

<210> SEQ ID NO 9
<211> LENGTH: 14
<212> TYPE: PRT
<213> ORGANISM: Mus musculus

<400> SEQUENCE: 9

Trp Val Arg Gln Met Pro Gly Lys Gly Leu Glu Trp Met Gly
1               5                   10

<210> SEQ ID NO 10
<211> LENGTH: 32
<212> TYPE: PRT
<213> ORGANISM: Mus musculus

<400> SEQUENCE: 10

Gln Val Thr Leu Thr Ala Asp Lys Ser Ile Ser Thr Ala Tyr Leu Gln
1               5                   10                  15

Trp Ser Ser Leu Lys Ala Ser Asp Thr Ala Met Tyr Tyr Cys Ala Phe
            20                  25                  30

<210> SEQ ID NO 11
<211> LENGTH: 11
<212> TYPE: PRT
<213> ORGANISM: Mus musculus

<400> SEQUENCE: 11

Trp Gly Gln Gly Thr Thr Val Thr Val Ser Ser
1               5                   10

<210> SEQ ID NO 12
<211> LENGTH: 30
<212> TYPE: PRT
<213> ORGANISM: Mus musculus
<220> FEATURE:
<221> NAME/KEY: VARIANT
<222> LOCATION: (29)...(29)
<223> OTHER INFORMATION: Xaa is Leu or Phe

<400> SEQUENCE: 12

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Xaa Thr
```

-continued

```
<210> SEQ ID NO 13
<211> LENGTH: 14
<212> TYPE: PRT
<213> ORGANISM: Mus musculus

<400> SEQUENCE: 13

Trp Val Arg Gln Ala Pro Gly Gln Gly Leu Glu Trp Met Gly
1               5                   10

<210> SEQ ID NO 14
<211> LENGTH: 32
<212> TYPE: PRT
<213> ORGANISM: Mus musculus
<220> FEATURE:
<221> NAME/KEY: VARIANT
<222> LOCATION: (8)...(8)
<223> OTHER INFORMATION: Xaa is Lys or Thr
<220> FEATURE:
<221> NAME/KEY: VARIANT
<222> LOCATION: (32)...(32)
<223> OTHER INFORMATION: Xaa is Phe or Arg

<400> SEQUENCE: 14

Arg Val Thr Leu Thr Ala Asp Xaa Ser Thr Ser Thr Ala Tyr Met Glu
1               5                   10                  15

Leu Ser Ser Leu Arg Ser Glu Asp Thr Ala Val Tyr Tyr Cys Ala Xaa
            20                  25                  30

<210> SEQ ID NO 15
<211> LENGTH: 11
<212> TYPE: PRT
<213> ORGANISM: Mus musculus

<400> SEQUENCE: 15

Trp Gly Gln Gly Thr Leu Val Thr Val Ser Ser
1               5                   10

<210> SEQ ID NO 16
<211> LENGTH: 32
<212> TYPE: PRT
<213> ORGANISM: Mus musculus
<220> FEATURE:
<221> NAME/KEY: VARIANT
<222> LOCATION: (8)...(8)
<223> OTHER INFORMATION: Xaa is Lys or Thr
<220> FEATURE:
<221> NAME/KEY: VARIANT
<222> LOCATION: (32)...(32)
<223> OTHER INFORMATION: Xaa is Phe or Arg

<400> SEQUENCE: 16

Arg Val Thr Met Thr Arg Asp Xaa Ser Thr Ser Thr Val Tyr Met Glu
1               5                   10                  15

Leu Ser Ser Leu Arg Ser Glu Asp Thr Ala Val Tyr Tyr Cys Ala Xaa
            20                  25                  30

<210> SEQ ID NO 17
<211> LENGTH: 23
<212> TYPE: PRT
<213> ORGANISM: Mus musculus

<400> SEQUENCE: 17

Asp Ile Gln Met Thr Gln Ser Pro Ser Ser Leu Ser Ala Ser Val Gly
1               5                   10                  15
```

Asp Arg Val Thr Ile Thr Cys
            20

<210> SEQ ID NO 18
<211> LENGTH: 15
<212> TYPE: PRT
<213> ORGANISM: Mus musculus

<400> SEQUENCE: 18

Trp Tyr Gln Gln Lys Pro Gly Lys Val Pro Lys Leu Leu Ile Tyr
1               5                   10                  15

<210> SEQ ID NO 19
<211> LENGTH: 32
<212> TYPE: PRT
<213> ORGANISM: Mus musculus
<220> FEATURE:
<221> NAME/KEY: VARIANT
<222> LOCATION: (15)...(15)
<223> OTHER INFORMATION: Xaa is Phe or Tyr

<400> SEQUENCE: 19

Gly Val Pro Ser Arg Phe Ser Gly Ser Arg Ser Glu Thr Gln Xaa Ser
1               5                   10                  15

Leu Thr Ile Ser Ser Leu Gln Pro Glu Asp Val Ala Thr Tyr Tyr Cys
            20                  25                  30

<210> SEQ ID NO 20
<211> LENGTH: 11
<212> TYPE: PRT
<213> ORGANISM: Mus musculus

<400> SEQUENCE: 20

Phe Gly Gln Gly Thr Lys Val Glu Ile Lys Arg
1               5                   10

<210> SEQ ID NO 21
<211> LENGTH: 32
<212> TYPE: PRT
<213> ORGANISM: Mus musculus
<220> FEATURE:
<221> NAME/KEY: VARIANT
<222> LOCATION: (15)...(15)
<223> OTHER INFORMATION: Xaa is Tyr or Phe

<400> SEQUENCE: 21

Gly Val Pro Ser Arg Phe Ser Gly Ser Gly Ser Gly Thr Asp Xaa Thr
1               5                   10                  15

Leu Thr Ile Ser Ser Leu Gln Pro Glu Asp Val Ala Thr Tyr Tyr Cys
            20                  25                  30

<210> SEQ ID NO 22
<211> LENGTH: 17
<212> TYPE: PRT
<213> ORGANISM: Mus musculus
<220> FEATURE:
<221> NAME/KEY: VARIANT
<222> LOCATION: (13)...(13)
<223> OTHER INFORMATION: Xaa is Gln or Pro
<220> FEATURE:
<221> NAME/KEY: VARIANT
<222> LOCATION: (14)...(14)
<223> OTHER INFORMATION: Xaa is Ser or Lys
<220> FEATURE:
<221> NAME/KEY: VARIANT
<222> LOCATION: (16)...(16)
<223> OTHER INFORMATION: Xaa is Gln or Lys -continued

<400> SEQUENCE: 22

Ala Ile Tyr Pro Gly Asp Gly Asp Thr Arg Tyr Ser Xaa Xaa Phe Xaa
1               5                   10                  15

Gly

<210> SEQ ID NO 23
<211> LENGTH: 17
<212> TYPE: PRT
<213> ORGANISM: Mus musculus

<400> SEQUENCE: 23

Ala Ile Tyr Pro Gly Asp Gly Asp Thr Arg Tyr Ser Gln Lys Phe Lys
1               5                   10                  15

Gly

<210> SEQ ID NO 24
<211> LENGTH: 164
<212> TYPE: PRT
<213> ORGANISM: Homo sapiens

<400> SEQUENCE: 24

Met Ala Ser His Ser Gly Pro Ser Thr Ser Val Leu Phe Leu Phe Cys
1               5                   10                  15

Cys Leu Gly Gly Trp Leu Ala Ser His Thr Leu Pro Val Arg Leu Leu
                20                  25                  30

Arg Pro Ser Asp Asp Val Gln Lys Ile Val Glu Glu Leu Gln Ser Leu
            35                  40                  45

Ser Lys Met Leu Leu Lys Asp Val Glu Glu Lys Gly Val Leu Val
50                  55                  60

Ser Gln Asn Tyr Thr Leu Pro Cys Leu Ser Pro Asp Ala Gln Pro Pro
65                  70                  75                  80

Asn Asn Ile His Ser Pro Ala Ile Arg Ala Tyr Leu Lys Thr Ile Arg
                85                  90                  95

Gln Leu Asp Asn Lys Ser Val Ile Asp Glu Ile Ile Glu His Leu Asp
            100                 105                 110

Lys Leu Ile Phe Gln Asp Ala Pro Glu Thr Asn Ile Ser Val Pro Thr
        115                 120                 125

Asp Thr His Glu Cys Lys Arg Phe Ile Leu Thr Ile Ser Gln Gln Phe
    130                 135                 140

Ser Glu Cys Met Asp Leu Ala Leu Lys Ser Leu Thr Ser Gly Ala Gln
145                 150                 155                 160

Gln Ala Thr Thr

<210> SEQ ID NO 25
<211> LENGTH: 122
<212> TYPE: PRT
<213> ORGANISM: Mus musculus

<400> SEQUENCE: 25

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Leu Thr Arg Tyr
                20                  25                  30

Trp Met Gln Trp Val Arg Gln Ala Pro Gly Gln Gly Leu Glu Trp Met
            35                  40                  45

Gly Ala Ile Tyr Pro Gly Asp Gly Asp Thr Arg Tyr Ser Gln Lys Phe
        50                  55                  60

```
Gln Gly Arg Val Thr Leu Thr Ala Asp Lys Ser Ile Ser Thr Ala Tyr
 65                  70                  75                  80

Met Glu Leu Ser Ser Leu Arg Ser Glu Asp Thr Ala Val Tyr Tyr Cys
                 85                  90                  95

Ala Phe Pro Asp Gly Tyr Tyr Ala Ala Pro Tyr Gly Met Asp Tyr Trp
            100                 105                 110

Gly Gln Gly Thr Leu Val Thr Val Ser Ser
        115                 120
```

<210> SEQ ID NO 26
<211> LENGTH: 108
<212> TYPE: PRT
<213> ORGANISM: Mus musculus

<400> SEQUENCE: 26

```
Asp Ile Gln Met Thr Gln Ser Pro Ser Ser Leu Ser Ala Ser Val Gly
  1               5                  10                  15

Asp Arg Val Thr Ile Thr Cys Arg Ala Ser Gly Asn Ile His Asn Tyr
             20                  25                  30

Leu Ala Trp Tyr Gln Gln Lys Pro Gly Lys Val Pro Lys Leu Leu Ile
         35                  40                  45

Tyr Asn Ala Lys Thr Leu Ala Asp Gly Val Pro Ser Arg Phe Ser Gly
 50                  55                  60

Ser Arg Ser Glu Thr Gln Tyr Ser Leu Thr Ile Ser Ser Leu Gln Pro
 65                  70                  75                  80

Glu Asp Val Ala Thr Tyr Tyr Cys Gln His Phe Trp Ser Thr Pro Trp
                 85                  90                  95

Thr Phe Gly Gln Gly Thr Lys Val Glu Ile Lys Arg
            100                 105
```

<210> SEQ ID NO 27
<211> LENGTH: 122
<212> TYPE: PRT
<213> ORGANISM: Mus musculus

<400> SEQUENCE: 27

```
Glu Val Gln Leu Val Gln Ser Gly Ala Glu Val Lys Lys Pro Gly Glu
  1               5                  10                  15

Ser Leu Lys Ile Ser Cys Lys Ala Ser Gly Tyr Thr Leu Thr Arg Tyr
             20                  25                  30

Trp Met Gln Trp Val Arg Gln Met Pro Gly Lys Gly Leu Glu Trp Met
         35                  40                  45

Gly Ala Ile Tyr Pro Gly Asp Gly Asp Thr Arg Tyr Ser Pro Ser Phe
 50                  55                  60

Gln Gly Gln Val Thr Leu Thr Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Ala Phe Pro Asp Gly Tyr Tyr Ala Ala Pro Tyr Gly Met Asp Tyr Trp
            100                 105                 110

Gly Gln Gly Thr Thr Val Thr Val Ser Ser
        115                 120
```

<210> SEQ ID NO 28
<211> LENGTH: 108
<212> TYPE: PRT
<213> ORGANISM: Mus musculus

<400> SEQUENCE: 28

Asp Ile Gln Met Thr Gln Ser Pro Ser Ser Leu Ser Ala Ser Val Gly
1               5                   10                  15

Asp Arg Val Thr Ile Thr Cys Arg Ala Ser Gly Asn Ile His Asn Tyr
            20                  25                  30

Leu Ala Trp Tyr Gln Gln Lys Pro Gly Lys Val Pro Lys Leu Leu Ile
        35                  40                  45

Tyr Asn Ala Lys Thr Leu Ala Asp Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln His Phe Trp Ser Thr Pro Trp
                85                  90                  95

Thr Phe Gly Gln Gly Thr Lys Val Glu Ile Lys Arg
            100                 105

<210> SEQ ID NO 29
<211> LENGTH: 122
<212> TYPE: PRT
<213> ORGANISM: Mus musculus

<400> SEQUENCE: 29

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Arg Tyr
            20                  25                  30

Trp Met Gln Trp Val Arg Gln Ala Pro Gly Gln Gly Leu Glu Trp Met
        35                  40                  45

Gly Ala Ile Tyr Pro Gly Asp Gly Asp Thr Arg Tyr Ser Gln Lys Phe
50                  55                  60

Gln Gly Arg Val Thr Met Thr Arg Asp Thr Ser Ile Ser Thr Val Tyr
65                  70                  75                  80

Met Glu Leu Ser Ser Leu Arg Ser Glu Asp Thr Ala Val Tyr Tyr Cys
                85                  90                  95

Ala Arg Pro Asp Gly Tyr Tyr Ala Ala Pro Tyr Gly Met Asp Tyr Trp
            100                 105                 110

Gly Gln Gly Thr Leu Val Thr Val Ser Ser
        115                 120

<210> SEQ ID NO 30
<211> LENGTH: 122
<212> TYPE: PRT
<213> ORGANISM: Mus musculus

<400> SEQUENCE: 30

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Leu Thr Arg Tyr
            20                  25                  30

Trp Met Gln Trp Val Arg Gln Ala Pro Gly Gln Gly Leu Glu Trp Met
        35                  40                  45

Gly Ala Ile Tyr Pro Gly Asp Gly Asp Thr Arg Tyr Ser Gln Lys Phe
50                  55                  60

Gln Gly Arg Val Thr Leu Thr Ala Asp Lys Ser Ile Ser Thr Ala Tyr
65                  70                  75                  80

```
Met Glu Leu Ser Ser Leu Arg Ser Glu Asp Thr Ala Val Tyr Tyr Cys
                85                  90                  95

Ala Arg Pro Asp Gly Tyr Tyr Ala Ala Pro Tyr Gly Met Asp Tyr Trp
            100                 105                 110

Gly Gln Gly Thr Leu Val Thr Val Ser Ser
        115                 120

<210> SEQ ID NO 31
<211> LENGTH: 122
<212> TYPE: PRT
<213> ORGANISM: Mus musculus

<400> SEQUENCE: 31

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Arg Tyr
            20                  25                  30

Trp Met Gln Trp Val Arg Gln Ala Pro Gly Gln Gly Leu Glu Trp Met
        35                  40                  45

Gly Ala Ile Tyr Pro Gly Asp Gly Asp Thr Arg Tyr Ser Gln Lys Phe
    50                  55                  60

Gln Gly Arg Val Thr Leu Thr Ala Asp Lys Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Phe Pro Asp Gly Tyr Tyr Ala Ala Pro Tyr Gly Met Asp Tyr Trp
            100                 105                 110

Gly Gln Gly Thr Leu Val Thr Val Ser Ser
        115                 120

<210> SEQ ID NO 32
<211> LENGTH: 108
<212> TYPE: PRT
<213> ORGANISM: Mus musculus

<400> SEQUENCE: 32

Asp Ile Gln Met Thr Gln Ser Pro Ser Ser Leu Ser Ala Ser Val Gly
1               5                   10                  15

Asp Arg Val Thr Ile Thr Cys Arg Ala Ser Gly Asn Ile His Asn Tyr
            20                  25                  30

Leu Ala Trp Tyr Gln Gln Lys Pro Gly Lys Val Pro Lys Leu Leu Ile
        35                  40                  45

Tyr Asn Ala Lys Thr Leu Ala Asp Gly Val Pro Ser Arg Phe Ser Gly
    50                  55                  60

Ser Arg Ser Glu Thr Gln Phe Ser Leu Thr Ile Ser Ser Leu Gln Pro
65                  70                  75                  80

Glu Asp Val Ala Thr Tyr Tyr Cys Gln His Phe Trp Ser Thr Pro Trp
                85                  90                  95

Thr Phe Gly Gln Gly Thr Lys Val Glu Ile Lys Arg
            100                 105

<210> SEQ ID NO 33
<211> LENGTH: 108
<212> TYPE: PRT
<213> ORGANISM: Mus musculus

<400> SEQUENCE: 33

Asp Ile Gln Met Thr Gln Ser Pro Ser Ser Leu Ser Ala Ser Val Gly
```

```
                 1               5                   10                  15
Asp Arg Val Thr Ile Thr Cys Arg Ala Ser Gly Asn Ile His Asn Tyr
                20                  25                  30

Leu Ala Trp Tyr Gln Gln Lys Pro Gly Lys Val Pro Lys Leu Leu Ile
        35                  40                  45

Tyr Asn Ala Lys Thr Leu Ala Asp Gly Val Pro Ser Arg Phe Ser Gly
    50                  55                  60

Ser Gly Ser Gly Thr Gln Tyr Ser Leu Thr Ile Ser Ser Leu Gln Pro
65                  70                  75                  80

Glu Asp Val Ala Thr Tyr Tyr Cys Gln His Phe Trp Ser Thr Pro Trp
                85                  90                  95

Thr Phe Gly Gln Gly Thr Lys Val Glu Ile Lys Arg
                100                 105
```

<210> SEQ ID NO 34
<211> LENGTH: 108
<212> TYPE: PRT
<213> ORGANISM: Mus musculus

<400> SEQUENCE: 34

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gly Asn Ile His Asn Tyr
                20                  25                  30

Leu Ala Trp Tyr Gln Gln Lys Pro Gly Lys Val Pro Lys Leu Leu Ile
        35                  40                  45

Tyr Asn Ala Lys Thr Leu Ala Asp Gly Val Pro Ser Arg Phe Ser Gly
    50                  55                  60

Ser Arg Ser Glu Thr Asp Tyr Thr Leu Thr Ile Ser Ser Leu Gln Pro
65                  70                  75                  80

Glu Asp Val Ala Thr Tyr Tyr Cys Gln His Phe Trp Ser Thr Pro Trp
                85                  90                  95

Thr Phe Gly Gln Gly Thr Lys Val Glu Ile Lys Arg
                100                 105
```

<210> SEQ ID NO 35
<211> LENGTH: 122
<212> TYPE: PRT
<213> ORGANISM: Mus musculus

<400> SEQUENCE: 35

```
Glu Val Gln Leu Val Gln Ser Gly Ala Glu Val Lys Lys Pro Gly Glu
1               5                   10                  15

Ser Leu Lys Ile Ser Cys Lys Ala Ser Gly Tyr Thr Leu Thr Arg Tyr
                20                  25                  30

Trp Met Gln Trp Val Arg Gln Met Pro Gly Lys Gly Leu Glu Trp Met
        35                  40                  45

Gly Ala Ile Tyr Pro Gly Asp Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Phe Pro Asp Gly Tyr Tyr Ala Ala Pro Tyr Gly Met Asp Tyr Trp
                100                 105                 110

Gly Gln Gly Thr Thr Val Thr Val Ser Ser
```

```
                    115                 120

<210> SEQ ID NO 36
<211> LENGTH: 122
<212> TYPE: PRT
<213> ORGANISM: Mus musculus

<400> SEQUENCE: 36

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Leu Thr Arg Tyr
                20                  25                  30

Trp Met Gln Trp Val Arg Gln Ala Pro Gly Gln Gly Leu Glu Trp Met
            35                  40                  45

Gly Ala Ile Tyr Pro Gly Asp Gly Asp Thr Arg Tyr Ser Gln Lys Phe
        50                  55                  60

Gln Gly Arg Val Thr Met Thr Arg Asp Thr Ser Ile Ser Thr Val Tyr
65                  70                  75                  80

Met Glu Leu Ser Ser Leu Arg Ser Glu Asp Thr Ala Val Tyr Tyr Cys
                85                  90                  95

Ala Phe Pro Asp Gly Tyr Tyr Ala Ala Pro Tyr Gly Met Asp Tyr Trp
                100                 105                 110

Gly Gln Gly Thr Leu Val Thr Val Ser Ser
            115                 120

<210> SEQ ID NO 37
<211> LENGTH: 108
<212> TYPE: PRT
<213> ORGANISM: Mus musculus

<400> SEQUENCE: 37

Asp Ile Gln Met Thr Gln Ser Pro Ser Ser Leu Ser Ala Ser Val Gly
1               5                   10                  15

Asp Arg Val Thr Ile Thr Cys Arg Ala Ser Gly Asn Ile His Asn Tyr
                20                  25                  30

Leu Ala Trp Tyr Gln Gln Lys Pro Gly Lys Val Pro Lys Leu Leu Ile
            35                  40                  45

Tyr Asn Ala Lys Thr Leu Ala Asp Gly Val Pro Ser Arg Phe Ser Gly
        50                  55                  60

Ser Gly Ser Gly Thr Asp Tyr Thr Leu Thr Ile Ser Ser Leu Gln Pro
65                  70                  75                  80

Glu Asp Val Ala Thr Tyr Tyr Cys Gln His Phe Trp Ser Thr Pro Trp
                85                  90                  95

Thr Phe Gly Gln Gly Thr Lys Val Glu Ile Lys Arg
                100                 105

<210> SEQ ID NO 38
<211> LENGTH: 122
<212> TYPE: PRT
<213> ORGANISM: Mus musculus

<400> SEQUENCE: 38

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Leu Thr Arg Tyr
                20                  25                  30

Trp Met Gln Trp Val Arg Gln Ala Pro Gly Gln Gly Leu Glu Trp Met
            35                  40                  45
```

Gly Ala Ile Tyr Pro Gly Asp Gly Asp Thr Arg Tyr Ser Gln Lys Phe
            50                  55                  60

Gln Gly Arg Val Thr Leu Thr Arg Asp Thr Ser Ile Ser Thr Val Tyr
65                  70                  75                  80

Met Glu Leu Ser Ser Leu Arg Ser Glu Asp Thr Ala Val Tyr Tyr Cys
                85                  90                  95

Ala Phe Pro Asp Gly Tyr Tyr Ala Ala Pro Tyr Gly Met Asp Tyr Trp
                100                 105                 110

Gly Gln Gly Thr Leu Val Thr Val Ser Ser
            115                 120

<210> SEQ ID NO 39
<211> LENGTH: 122
<212> TYPE: PRT
<213> ORGANISM: Mus musculus

<400> SEQUENCE: 39

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Leu Thr Arg Tyr
                20                  25                  30

Trp Met Gln Trp Val Arg Gln Ala Pro Gly Gln Gly Leu Glu Trp Met
            35                  40                  45

Gly Ala Ile Tyr Pro Gly Asp Gly Asp Thr Arg Tyr Ser Gln Lys Phe
        50                  55                  60

Gln Gly Arg Val Thr Met Thr Asp Thr Ser Ile Ser Thr Val Tyr
65                  70                  75                  80

Met Glu Leu Ser Ser Leu Arg Ser Glu Asp Thr Ala Val Tyr Tyr Cys
                85                  90                  95

Ala Phe Pro Asp Gly Tyr Tyr Ala Ala Pro Tyr Gly Met Asp Tyr Trp
                100                 105                 110

Gly Gln Gly Thr Leu Val Thr Val Ser Ser
            115                 120

<210> SEQ ID NO 40
<211> LENGTH: 122
<212> TYPE: PRT
<213> ORGANISM: Mus musculus

<400> SEQUENCE: 40

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Leu Thr Arg Tyr
                20                  25                  30

Trp Met Gln Trp Val Arg Gln Ala Pro Gly Gln Gly Leu Glu Trp Met
            35                  40                  45

Gly Ala Ile Tyr Pro Gly Asp Gly Asp Thr Arg Tyr Ser Gln Lys Phe
        50                  55                  60

Gln Gly Arg Val Thr Met Thr Arg Asp Lys Ser Ile Ser Thr Val Tyr
65                  70                  75                  80

Met Glu Leu Ser Ser Leu Arg Ser Glu Asp Thr Ala Val Tyr Tyr Cys
                85                  90                  95

Ala Phe Pro Asp Gly Tyr Tyr Ala Ala Pro Tyr Gly Met Asp Tyr Trp
                100                 105                 110

Gly Gln Gly Thr Leu Val Thr Val Ser Ser
            115                 120

<210> SEQ ID NO 41
<211> LENGTH: 122
<212> TYPE: PRT
<213> ORGANISM: Mus musculus

<400> SEQUENCE: 41

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Leu Thr Arg Tyr
            20                  25                  30

Trp Met Gln Trp Val Arg Gln Ala Pro Gly Gln Gly Leu Glu Trp Met
        35                  40                  45

Gly Ala Ile Tyr Pro Gly Asp Gly Asp Thr Arg Tyr Ser Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Phe Pro Asp Gly Tyr Tyr Ala Ala Pro Tyr Gly Met Asp Tyr Trp
            100                 105                 110

Gly Gln Gly Thr Leu Val Thr Val Ser Ser
        115                 120

<210> SEQ ID NO 42
<211> LENGTH: 122
<212> TYPE: PRT
<213> ORGANISM: Mus musculus

<400> SEQUENCE: 42

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Leu Thr Arg Tyr
            20                  25                  30

Trp Met Gln Trp Val Arg Gln Ala Pro Gly Gln Gly Leu Glu Trp Met
        35                  40                  45

Gly Ala Ile Tyr Pro Gly Asp Gly Asp Thr Arg Tyr Ser Gln Lys Phe
    50                  55                  60

Gln Gly Arg Val Thr Leu Thr Ala Asp Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Phe Pro Asp Gly Tyr Tyr Ala Ala Pro Tyr Gly Met Asp Tyr Trp
            100                 105                 110

Gly Gln Gly Thr Leu Val Thr Val Ser Ser
        115                 120

<210> SEQ ID NO 43
<211> LENGTH: 122
<212> TYPE: PRT
<213> ORGANISM: Mus musculus

<400> SEQUENCE: 43

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Leu Thr Arg Tyr
            20                  25                  30

Trp Met Gln Trp Val Arg Gln Ala Pro Gly Gln Gly Leu Glu Trp Met
             35                  40                  45

Gly Ala Ile Tyr Pro Gly Asp Gly Asp Thr Arg Tyr Ser Gln Lys Phe
         50                  55                  60

Gln Gly Arg Val Thr Met Thr Ala Asp Thr Ser Ile Ser Thr Ala Tyr
65                  70                  75                  80

Met Glu Leu Ser Ser Leu Arg Ser Glu Asp Thr Ala Val Tyr Tyr Cys
                 85                  90                  95

Ala Phe Pro Asp Gly Tyr Tyr Ala Ala Pro Tyr Gly Met Asp Tyr Trp
             100                 105                 110

Gly Gln Gly Thr Leu Val Thr Val Ser Ser
         115                 120

<210> SEQ ID NO 44
<211> LENGTH: 122
<212> TYPE: PRT
<213> ORGANISM: Mus musculus

<400> SEQUENCE: 44

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Leu Thr Arg Tyr
             20                  25                  30

Trp Met Gln Trp Val Arg Gln Ala Pro Gly Gln Gly Leu Glu Trp Met
             35                  40                  45

Gly Ala Ile Tyr Pro Gly Asp Gly Asp Thr Arg Tyr Ser Gln Lys Phe
         50                  55                  60

Gln Gly Arg Val Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                 85                  90                  95

Ala Phe Pro Asp Gly Tyr Tyr Ala Ala Pro Tyr Gly Met Asp Tyr Trp
             100                 105                 110

Gly Gln Gly Thr Leu Val Thr Val Ser Ser
         115                 120

<210> SEQ ID NO 45
<211> LENGTH: 122
<212> TYPE: PRT
<213> ORGANISM: Mus musculus

<400> SEQUENCE: 45

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Leu Thr Arg Tyr
             20                  25                  30

Trp Met Gln Trp Val Arg Gln Ala Pro Gly Gln Gly Leu Glu Trp Met
             35                  40                  45

Gly Ala Ile Tyr Pro Gly Asp Gly Asp Thr Arg Tyr Ser Gln Lys Phe
         50                  55                  60

Gln Gly Arg Val Thr Met Thr Arg Asp Lys Ser Thr Ser Thr Val Tyr
65                  70                  75                  80

Met Glu Leu Ser Ser Leu Arg Ser Glu Asp Thr Ala Val Tyr Tyr Cys
                 85                  90                  95

Ala Phe Pro Asp Gly Tyr Tyr Ala Ala Pro Tyr Gly Met Asp Tyr Trp
             100                 105                 110

```
Gly Gln Gly Thr Leu Val Thr Val Ser Ser
        115                 120
```

<210> SEQ ID NO 46
<211> LENGTH: 214
<212> TYPE: PRT
<213> ORGANISM: Mus musculus

<400> SEQUENCE: 46

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gly Asn Ile His Asn Tyr
            20                  25                  30

Leu Ala Trp Tyr Gln Gln Lys Pro Gly Lys Val Pro Lys Leu Leu Ile
        35                  40                  45

Tyr Asn Ala Lys Thr Leu Ala Asp Gly Val Pro Ser Arg Phe Ser Gly
    50                  55                  60

Ser Arg Ser Glu Thr Gln Tyr Ser Leu Thr Ile Ser Ser Leu Gln Pro
65                  70                  75                  80

Glu Asp Val Ala Thr Tyr Tyr Cys Gln His Phe Trp Ser Thr Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 47
<211> LENGTH: 449
<212> TYPE: PRT
<213> ORGANISM: Mus musculus

<400> SEQUENCE: 47

```
Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Leu Thr Arg Tyr
            20                  25                  30

Trp Met Gln Trp Val Arg Gln Ala Pro Gly Gln Gly Leu Glu Trp Met
        35                  40                  45

Gly Ala Ile Tyr Pro Gly Asp Gly Asp Thr Arg Tyr Ser Gln Lys Phe
    50                  55                  60

Gln Gly Arg Val Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95
```

Ala Phe Pro Asp Gly Tyr Tyr Ala Ala Pro Tyr Gly Met Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
        195                 200                 205

His Lys Pro Ser Asn Thr Lys Val Asp Lys Arg Val Glu Ser Lys Tyr
    210                 215                 220

Gly Pro Pro Cys Pro Pro Cys Pro Ala Pro Glu Phe Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
        275                 280                 285

Ala Lys Thr Lys Pro Arg Glu Glu Gln Phe Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Gln Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Glu Gly Asn Val Phe Ser Cys Ser Val Met His Glu
            420                 425                 430

Ala Leu His Asn His Tyr Thr Gln Lys Ser Leu Ser Leu Ser Leu Gly
        435                 440                 445

Lys

<210> SEQ ID NO 48
<211> LENGTH: 214
<212> TYPE: PRT
<213> ORGANISM: Mus musculus

<400> SEQUENCE: 48

Asp Ile Gln Met Thr Gln Ser Pro Ser Ser Leu Ser Ala Ser Val Gly
1               5                   10                  15

Asp Arg Val Thr Ile Thr Cys Arg Ala Ser Gly Asn Ile His Asn Tyr
            20                  25                  30

Leu Ala Trp Tyr Gln Gln Lys Pro Gly Lys Val Pro Lys Leu Leu Ile
        35                  40                  45

Tyr Asn Ala Lys Thr Leu Ala Asp Gly Val Pro Ser Arg Phe Ser Gly
50                      55                  60

Ser Gly Ser Gly Thr Asp Tyr Thr Leu Thr Ile Ser Ser Leu Gln Pro
65                  70                  75                  80

Glu Asp Val Ala Thr Tyr Tyr Cys Gln His Phe Trp Ser Thr Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 49
<211> LENGTH: 449
<212> TYPE: PRT
<213> ORGANISM: Mus musculus

<400> SEQUENCE: 49

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Leu Thr Arg Tyr
            20                  25                  30

Trp Met Gln Trp Val Arg Gln Ala Pro Gly Gln Gly Leu Glu Trp Met
        35                  40                  45

Gly Ala Ile Tyr Pro Gly Asp Gly Asp Thr Arg Tyr Ser Gln Lys Phe
    50                  55                  60

Gln Gly Arg Val Thr Met Thr Arg Asp Lys Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Phe Pro Asp Gly Tyr Tyr Ala Pro Tyr Gly Met Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
            195                 200                 205

His Lys Pro Ser Asn Thr Lys Val Asp Lys Arg Val Glu Ser Lys Tyr
            210                 215                 220

Gly Pro Pro Cys Pro Pro Cys Pro Ala Pro Glu Phe Leu Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
            275                 280                 285

Ala Lys Thr Lys Pro Arg Glu Glu Gln Phe Asn Ser Thr Tyr Arg Val
            290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
            325                 330                 335

Thr Ile Ser Lys Ala Lys Gly Gln Pro Arg Glu Pro Gln Val Tyr Thr
            340                 345                 350

Leu Pro Pro Ser Gln Glu Glu Met Thr Lys Asn Gln Val Ser Leu Thr
            355                 360                 365

Cys Leu Val Lys Gly Phe Tyr Pro Ser Asp Ile Ala Val Glu Trp Glu
            370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
            405                 410                 415

Ser Arg Trp Gln Glu Gly Asn Val Phe Ser Cys Ser Val Met His Glu
            420                 425                 430

Ala Leu His Asn His Tyr Thr Gln Lys Ser Leu Ser Leu Ser Leu Gly
            435                 440                 445

Lys

<210> SEQ ID NO 50
<211> LENGTH: 214
<212> TYPE: PRT
<213> ORGANISM: Mus musculus

<400> SEQUENCE: 50

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gly Asn Ile His Asn Tyr
            20                  25                  30

Leu Ala Trp Tyr Gln Gln Lys Pro Gly Lys Val Pro Lys Leu Leu Ile
            35                  40                  45

Tyr Asn Ala Lys Thr Leu Ala Asp Gly Val Pro Ser Arg Phe Ser Gly
            50                  55                  60

Ser Arg Ser Glu Thr Gln Tyr Ser Leu Thr Ile Ser Ser Leu Gln Pro
65                  70                  75                  80

Glu Asp Val Ala Thr Tyr Tyr Cys Gln His Phe Trp Ser Thr Pro Trp
            85                  90                  95

```
Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
            210

<210> SEQ ID NO 51
<211> LENGTH: 449
<212> TYPE: PRT
<213> ORGANISM: Mus musculus

<400> SEQUENCE: 51

Glu Val Gln Leu Val Gln Ser Gly Ala Glu Val Lys Lys Pro Gly Glu
1               5                   10                  15

Ser Leu Lys Ile Ser Cys Lys Ala Ser Gly Tyr Thr Leu Thr Arg Tyr
            20                  25                  30

Trp Met Gln Trp Val Arg Gln Met Pro Gly Lys Gly Leu Glu Trp Met
        35                  40                  45

Gly Ala Ile Tyr Pro Gly Asp Gly Asp Thr Arg Tyr Ser Pro Ser Phe
    50                  55                  60

Gln Gly Gln Val Thr Leu Thr Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Phe Pro Asp Gly Tyr Tyr Ala Ala Pro Tyr Gly Met Asp Tyr Trp
            100                 105                 110

Gly Gln Gly Thr Thr Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
            195                 200                 205

His Lys Pro Ser Asn Thr Lys Val Asp Lys Arg Val Glu Ser Lys Tyr
        210                 215                 220

Gly Pro Pro Cys Pro Pro Cys Pro Ala Pro Glu Phe Leu Gly Gly Pro
225                 230                 235                 240

Ser Val Phe Leu Phe Pro Pro Lys Pro Lys Asp Thr Leu Met Ile Ser
```

-continued

```
            245                 250                 255
Arg Thr Pro Glu Val Thr Cys Val Val Val Asp Val Ser Gln Glu Asp
            260                 265                 270
Pro Glu Val Gln Phe Asn Trp Tyr Val Asp Gly Val Glu Val His Asn
            275                 280             285
Ala Lys Thr Lys Pro Arg Glu Glu Gln Phe Asn Ser Thr Tyr Arg Val
        290             295                 300
Val Ser Val Leu Thr Val Leu His Gln Asp Trp Leu Asn Gly Lys Glu
305                 310                 315                 320
Tyr Lys Cys Lys Val Ser Asn Lys Gly Leu Pro Ser Ser Ile Glu Lys
                325                 330                 335
Thr Ile Ser Lys Ala Lys Gly Gln Pro Arg Glu Pro Gln Val Tyr Thr
            340                 345             350
Leu Pro Pro Ser Gln Glu Glu Met Thr Lys Asn Gln Val Ser Leu Thr
            355                 360             365
Cys Leu Val Lys Gly Phe Tyr Pro Ser Asp Ile Ala Val Glu Trp Glu
    370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Arg Leu Thr Val Asp Lys
                405                 410                 415
Ser Arg Trp Gln Glu Gly Asn Val Phe Ser Cys Ser Val Met His Glu
            420                 425             430
Ala Leu His Asn His Tyr Thr Gln Lys Ser Leu Ser Leu Ser Leu Gly
        435             440                 445
Lys
```